(12) United States Patent
Sastry et al.

(10) Patent No.: US 7,659,071 B2
(45) Date of Patent: Feb. 9, 2010

(54) METHODS AND COMPOSITIONS RELATING TO HPV-ASSOCIATED PRE-CANCEROUS AND CANCEROUS GROWTHS, INCLUDING CIN

(75) Inventors: Jagannadha K. Sastry, Katy, TX (US); Guillermo Tortolero-Luna, Houston, TX (US); Michele Follen, Houston, TX (US)

(73) Assignee: Board of Regents, the University of Texas System, Austin, TX (US)

( * ) Notice: Subject to any disclaimer, the term of this patent is extended or adjusted under 35 U.S.C. 154(b) by 0 days.

(21) Appl. No.: 12/172,002

(22) Filed: Jul. 11, 2008

(65) Prior Publication Data
US 2009/0053296 A1 Feb. 26, 2009

Related U.S. Application Data

(62) Division of application No. 10/484,063, filed as application No. PCT/US02/23198 on Jul. 19, 2002, now Pat. No. 7,410,758.

(60) Provisional application No. 60/306,809, filed on Jul. 20, 2001.

(51) Int. Cl.
*C12Q 1/68* (2006.01)
(52) U.S. Cl. .......................................... 435/6
(58) Field of Classification Search ...................... 435/6
See application file for complete search history.

(56) References Cited

U.S. PATENT DOCUMENTS

| | | | |
|---|---|---|---|
| 5,665,535 A | 9/1997 | Orth et al. | 435/5 |
| 5,876,922 A | 3/1999 | Orth et al. | 435/5 |
| 6,135,965 A | 10/2000 | Tumer et al. | 600/476 |
| 6,258,576 B1 | 7/2001 | Richards-Kortum et al. | 435/172 |

FOREIGN PATENT DOCUMENTS

| EP | 0 402 132 | 6/1990 |
|---|---|---|
| EP | 0 520 994 | 1/1995 |

OTHER PUBLICATIONS

Japanese Office Action, issued in Japanese Application No. 2003-514964, dated Nov. 7, 2008.
Seedorf et al., "Human Papillomavirus Type 18 DNA Sequence," *Virology*, 145:181-185, 1985.
Aichele et al., "Antiviral cytotoxic T cell response induced by in vivo priming with a free synthetic peptide," *J. Exp. Med.*, 171(5):1815-1820, 1990.
Borysiewicz et al., "A recombinant vaccina virus encoding human papillomavirus types 16 and 18, E6 and E7 proteins as immunotherapy for cervical cancer," *Lancet*, 347:1523-1527, 1996.
Casement et al., "Cross-reactive cytotoxic T lymphocytes induced by V3 loop synthetic peptides from different strains of human immunodeficiency virus type 1," *Virology*, 211(1):261-267, 1995.

Cason et al., "Detection of antibodies to a linear epitope on the major coat protein (L1) of human papillomavirus type-16 (HPV-16) in sera from patients with cervical intraepithelial neoplasia and children," *Int. J. Cancer*, 50:349-355, 1992.
Chen et al., "Induction of cytotoxic T lymphocytes specific for a syngeneic tumor expressing the E6 oncoprotein of human papillomavirus type 16," *J Immunol.*, 148(8):2617-2621, 1992.
Clavel et al., "Human papillovirus detection by the hybrid capture II assay: a reliable test to select women with normal cervical smears at risk for developing cervical lesions," *Diagn. Mol. Pathol.*, 9(3):145-150, 2000.
Clerici et al., "Cytokine production patterns in cervical intraepithelial neoplasia: association with human papillomavirus infection," *J. Natl. Cancer Inst.*, 89(3):245-250, 1997.
de Gruijil et al., "T cell proliferative responses against human papillomavirus type 16 E7 oncoprotein are most prominent in cervical intraepithelial neoplasia patients with a persistent viral infection ," *J Gen Virol.*, (Pt 9):2183-91. 1996.
Deres et al., "In vivo priming of virus-specific cytotoxic T lymphocytes with synthetic lipopeptide vaccine," *Nature*, 342(6249):561-564, 1989.
Dillner et al., "Mapping of linear epitopes of human papillomavirus type 16 the L1 and L2 open reading framed," *Int. J. Cancer*, 45:529-535, 1990.
Feltkamp et al., "Vaccination with cytotoxic T lymphocyte epitope-containing peptide protects against a tumor induced by human papillomavirus type 16-transformed cells," *Eur. J. Immunol.*, 23:2242-2249, 1993.
Fischer et al., "The association of human papillomavirus type 16 E6 and E7 antibodies with stage of cervical cancer," *Gynecologic Oncology*, 61, No. 0099, 73-78, 1996.
Hamsikova et al., "Presence of antibodies to seven human papillomavirus type 16-derived peptides in cervical cancer patients and healthy controls," *J. Infect. Dis.*, 170:1424-1431, 1994.
Jha et al., "Antibodies to human papillomavirus and to other genital infectious agents and invasive cervical cancer risk," *Lancet*, 341:1116-1118, 1993.
Kadish et al., "Lymphoproliferative responses to human papillomavirus (HPV) type 16 proteins E6 and E7: outcome of HPV infection and associated neoplasia," *J. Natl. Cancer Inst.*, 89:1285-1293, 1997.
Kast et al., "Human leukocyte antigen-A2.1 restricted candidate cytotoxic T lymphocyte epitopes of human papillomavirus type 16 E6 and E7 proteins identified by using the processing-defective human cell line T2," *J. Immunotherapy*, 14:115-120, 1993.

(Continued)

*Primary Examiner*—Ali R. Salimi
(74) *Attorney, Agent, or Firm*—Fulbright & Jaworski LLP

(57) ABSTRACT

The present invention concerns the use of E6 and/or E7 peptides from human papilloma virus (HPV) to evaluate a cell-mediated response in a patient infected with HPV to determine the prognosis for that patient with respect to the development or recurrence of pre-cancerous or cancerous growths, including cervical intraepithelial neoplasia (CIN).

27 Claims, 4 Drawing Sheets

OTHER PUBLICATIONS

Kast et al., "In vivo efficacy of virus-derived peptides and virus-specific cytotoxic T lymphocytes," *Immunol Lett.*, 30(2):229-232, 1991.

Lorenzato et al., "DNA image cytometry and human papillomavirus (HPV) detection help to select smears at high risk of high-grade cervical lesions," *J. Pathol.*, 194(2):171-176, 2001.

Müller et al., "Identification of seroreactive regions of the human papillomavirus type 16 proteins E4, E6, E7 and L1," *Journal of General Virology*, 71:2709-2717, 1990.

Munger et al., "The E6 and E7 genes of the human papillomavirus type 16 together are necessary and sufficient for transformation of primary human keratinocytes," *J. Virol.*, 63:4417-4421, 1989.

Nakagawa et al., "Cytotoxic T lymphocyte responses to E6 and E7 proteins of human papillomavirus type 16: relationship to cervical intraepithelial neoplasia," *J. Infect. Dis.*, 175:927-931, 1997.

Nakagawa et al., "T-cell proliferative responses to human papillomavirus type 16 peptides: relationship to cervical intraepithelial neoplasia," *Clin. Diag. Lab. Immunol.*, 3(2):205-210, 1996.

Nehete et al., "Cross-reactive T-cell proliferative responses to V3 peptides corresponding to different geographical HIV-1 isolates in HIV-seropositive individuals," *J. Clin. Immunol.*, 16(2):115-124, 1996.

Nindl et al., "Antibodies against linear and conformational epitopes of the human papillomavirus (HPV) type 16 E6 and E7 oncoproteins in sera of cervical cancer patients," *Archives of Virology*, 137:341-353, 1994.

Office Communication, mail date Feb. 5, 2007.

Office Communication, mail date Jun. 4, 2007.

Park et al., "Cell-mediated immunity in cervical intraepithelial neoplasia," *Asia-Oceania J. Obstet. Gynaecol.*, 18:171-175, 1992.

Poljak et al., "Comparative evaluation of first- and second-generation digene hybrid capture assays for detection of human papillomaviruses associated with high or intermediate risk for cervical cancer," *J. Clin. Microbiol.*, 37(3):796-797, 1999.

Ressing et al., "Human CTL epitopes encoded by human papillomavirus type 16 E6 and E7 identified through in vivo and in vitro immunogenicigy studies of HLA-A *0201-binding peptides," *J. Immunology*, 154:5934-5943, 1995.

Ressing et al., "Occasional memory cytotoxic T-cell responses of patients with human papillomavirus type 16-positive cervical lesions against a human leukocyte antigen-A *0201-restricted E7-encoded epitome," *Cancer Res.*, 56:582-588, 1996.

Rochlitz et al., "Mutations in the ras protooncogenes are rare events in renal cell cancer," *Eur. J. Cancer*, 28(2/3):333-336, 1992.

Sarkar et al., "Studies on in vivo induction of cytotoxic T lymphocyte responses by synthetic peptides from E6 and E7 oncoproteins of human papillomavirus type 16," *Viral Immunol.*, 8(3):165-174, 1995.

Sasagawa et al., "Identification of antibodies against human papillomavirus type 16 E6 and E7 proteins in sera of patients with cervical neoplasias," *Japanese Journal of Cancer Research*, 83:705-713, 1992.

Sastry et al., "Effects of influenza virus-specific cytotoxic T-lymphocyte responses induced induced by a synthetic nucleoprotein peptide on the survival of mice challenged with a lethal dose of virus," *Vaccine*, 12(14):1281-1287, 1994.

Sastry et al., "Rapid in vivo induction of HIV-specific CD8+ cytotoxic T lymphocytes by a 15-amino acid unmodified free peptide from the immunodominant V3-loop of GP120," *Virology*, 188:502-509, 1992.

Schiffman et al., "Accuracy and interlaboratory reliability of human papillomavirus DNA testing by hybrid capture," *J. Clin. Microbiology*, 33(3):545-550, 1995.

Seedorf et al., "Identification of early proteins of the human papilloma viruses type 16 (HPV 16) and type 18 (HPV 18) in cervical carcinoma cells," *EMBO J.*, 6(1):139-144, 1987.

Sehr et al., "A generic capture ELISA for recombinant proteins fuse dto glutathione S-transferase: validation for HPV serology," *Journal of Immunological Methods*, 253(1-2):153-162, 2001.

Sheperd et al., "T cell responses to the human papillomavirus type 16 E7 protein in mice of different haplotypes," *J. Gen. Virol.*, 73:1269-1274, 1992.

Stauss et al., "Induction of cytotoxic T lymphocytes with peptides in vitro: identification of candidate T-cell epitopes in human papilloma virus," *Proc. Natl. Acad. Sci.*, USA, 89:7871-7875, 1992.

Strang et al., "Human T cell responses to human papillomavirus type 16 L1 and E6 synthetic peptides: identification of T cell determinants, HLA-DR restriction and virus type specificity," *J. Gen. Virol.*, 71:423-431, 1990.

Tindle et al., "Identification of B epitopes in human papillomavirus type 16 E7 open binding frame protein," *J. of General Virology*, 71:1347-1354, 1990.

Tindel et al., "A 'public' t-helper epitope of the E7 transforming protein of human papillomavirus 16 provides cognate help for several E7 B-cell epitopes from cervical cancer-associated human papillomavirus genotypes," *Proc. Natl. Acad. Sci.*, USA, 88:5887-5891, 1991.

Townsend et al., "The epitopes of influenza nucleoprotein recognized by cytotoxic T lymphocytes can be defined with short synthetic peptides," *Cell*, 44:7949-7968, 1986.

Tsukui et al., "Interleukin 2 production in vitro by peripheral lymphocytes in response to human papillomavirus-derived peptides: correlation with cervical pathology," *Cancer Res.*, 56:3967-3974, 1996.

Unanue and Cerottini, "Antigen presentation," *FASEB J.*, 3:2496-2502, 1989.

von Knebel Doeberitz et al., "Correlation of modified human papilloma virus early gene expression with altered growth properties in C4-1 cervical carcinoma cells," *Cancer Res.*, 48:3780-3786, 1988.

Wettstein, In: H. Pfister (ed.), *Papillomaviruses and Human Cancer*, pp. 145, Florida: CRC Press, 1990.

Baay et al., "Humoral immune response against proteins E6 and E7 in cervical carcinoma patients positive for human papilloma virus type 16 during treatment and follow-up," *Eur. J. Clin. Microbiol. Infect. Dis.*, 18:126-132, 1999.

Bonagura et al., "Recurrent respiratory papilomatosis: Altered CD8+ T-cell subsets and TH1/TH2 cytokine imbalance," *Clin. Immunol.*, 93:302-311, 1999.

De Silva et al., "Cervical cancer vaccines: emerging concepts and developments," *J. Cellular Physiol.*, 186:169-182, 2001.

Sarkar et al., "Association of significant cellular immune responses to synthetic peptides from the E6 and E7 oncoproteins of HPV-16 with disease-free condition in HPV+ patients treated for cervical intraepithelial nesplasia," *J. Acquired Immune Deficiency Syndromes Human Retrovirology*, 17:A29, 1998.

Stellato et al., "Type 1 cytokine response and treatment outcome of genital HPV lesions," *Genitourinary Med.*, 73:387-390, 1997.

Viladiu et al., "Human papillomavirus DNA and antibodies to human papillomaviruses 16 E2, L2, and E7 peptides as predictors of survival in patients with squamous cell cervical cancer," *J. Clin. Oncology*, 15:610-619, 1997.

METHODS AND COMPOSITIONS RELATING TO HPV-ASSOCIATED PRE-CANCEROUS AND CANCEROUS GROWTHS, INCLUDING CIN

This application is a divisional of U.S. application Ser. No. 10/484,063, filed on Oct. 7, 2004, now issued as U.S. Pat. No. 7,410,758, which claims priority to PCT/US02/23198, filed on Jul. 19, 2002, which claims priority to U.S. Provisional Patent Application No. 60/306,809 filed on Jul. 20, 2001, all of which are hereby incorporated by reference in their entirety.

The U.S. government has certain rights in the present invention pursuant to grant numbers CA016672, CA065571, and CA077378 from the National Institutes of Health.

BACKGROUND OF THE INVENTION

1. Field of the Invention

The present invention relates generally to the fields of immunology, virology, and oncology. More particularly, it concerns diagnostic and therapeutic methods related to the development and recurrence of pre-cancerous and cancerous growths or lesions, including cervical intraepithelial neoplasia (CIN), caused by human papilloma virus (HPV).

2. Description of Related Art

Cervical cancer is the second most common malignancy in women worldwide, accounting for 15% of all cancers diagnosed in women (Parkin et al., 1993). In the United States, cervical cancer is one of the most common neoplasm of the female genital tract. Laboratory and epidemiological research has focused on the etiological role of some types of human papilloma virus (HPV) in the pathogenesis of cervical neoplasia (Brinton, 1992; Munoz et al., 1992). Overall, HPV DNA has been detected in more than 79% of specimens of women with definite cervical disease. The most prevalent HPV type is HPV 16, which is detected in high-grade squamous intraepithelial lesions and cancer (Lörincz et al., 1992). Results from epidemiological studies support an association between cervical neoplasia and HPV, which is markedly stronger with HPV type 16 (Morrison et al., 1991; Koutsky et al., 1992; and Munoz et al., 1992). Neoplasia is characterized by abnormal growth of cells, which often results in the invasion of normal tissues, e.g., primary tumors or the spread to distant organs, e.g., metastasis.

The E6 and E7 genes of HPV 16 are frequently co-expressed and are most abundant viral transcripts in biopsies from HPV 16 positive cervical carcinoma (Wettstein, 1990; Seedorf et al., 1987). There is a strong evidence that co-expression of both E6 and E7 open reading frames is necessary and sufficient for efficient malignant transformation of a variety of mammalian cells (Munger et al., 1989). Furthermore, continued expression of the E6 and E7 regions of the viral genome appears to be required to maintain the malignant phenotype (von Knebel Doeberitz et al., 1988).

While some HPV infected patients develop cervical neoplasia, others do not. Also there is a high rate of spontaneous regression observed indicating the role of host immune responses. The induction of a cytotoxic T-lymphocyte (CTL) response constitutes a significant defense mechanism against viral infections; occasionally, a virus-specific CTL response can render full protection without a concomitant antibody response (Sastry et al., 1992; Bevan, 1989; Lukacher, 1984). Based on reports in the literature describing a relation between increased prevalence of anti-HPV antibodies, in particular those directed against the E7 oncoprotein, with severity of the cervical disease (Cason et al., 1992; Hamsikova et al., 1994; Jha et al., 1993), it has been suggested that HPV-specific humoral response may not play a protective role against HPV-associated cervical neoplasia (Nakagawa et al., 1996). On the other hand, it has been reported that individuals with defects in CMI have an increased prevalence of HPV-associated cervical neoplasia, indicating that T cells participate in the control of HPV-associated neoplasia in humans (Nakagawa et al., 1996; Tsukui et al.; 1996; Feltkamp et al., 1993 and Clerici et al., 1997). Decreased IL-2 production and proliferative responses to mitogens such as PHA and concanavalin-A have been observed in patients with invasive cervical carcinoma (Park et al., 1992). A number of in vitro and in vivo strategies have been described to identify peptides from HPV-16 E6, E7, and L1 proteins that induce T-cell activity in mice and humans (Feltkamp et al., 1993; Strang et al., 1990; Tindel et al., 1991; Shepherd et al., 1992; Stauss et al., 1992; Kast et al., 1993). Typically, induction of virus-specific CTLs can be effected by infection with a virus or recombinant virus that expresses a viral gene product. The viral gene product is processed and presented as a peptide on the surface of infected cells in association with an MHC class I molecule for recognition by the CTL (Unanue, 1989).

Additionally, research efforts have concentrated on identifying and characterizing HIV peptides that elicit a viral-specific CTL response. Townsend et al. illustrated the concept of using T-cell epitopes in proteins as vaccine candidates when their group demonstrated the use of short synthetic peptides from influenza nucleoprotein as epitopes for CTL responses (Townsend et al., 1986). The inventors and others have reported using synthetic peptides to generate virus-specific CTLs in vivo (Kast et al., 1991; Aichele et al., 1990; Deres et al., 1989; Sastry et al., 1992; Sastry et al., 1994; Casement et al., 1995) against influenza, lymphocytic choriomeningitis, Sendai virus and HIV.

Over 90% of cervical carcinomas express human papillomavirus (HPV) E6 and E7 proteins. These unique antigens are ideal targets for the development of cytotoxic T-lymphocytes (CTL) for antitumor immunotherapy. Synthetic peptides have been identified corresponding with the E6 and E7 oncoproteins of HPV-16 that were effective in including HPV-specific CTL responses in vivo (Sarkar et al., 1995). Recently, Nakagawa et al. reported that systemic T-cell proliferative responses and CTL responses to HPV-16 peptides and proteins were detectable in many virgin as well as sexually active women without cervical lesions but not in those with active disease (Nakagawa et al., 1997). Similarly, Tsukui et al. reported that TH lymphocyte response, particularly IL-2 production, to HPV antigens was greater among cytologically normal women than in women with different degrees of progressive cervical neoplasia (Tsukui et al., 1996). Also, Clerici et al. observed that production of TH1 cytokines (IL-2 and IFN-γ) which potentially enhances CMI, to be defective in women with extensive HPV infection and that progression to CIN to be associated with a shift from TH1 to TH2 cytokine production (Clerici et al., 1997). Employing a long term in vitro stimulation protocol for determining the TH activity Kadish et al. reported that lymphoproliferative responses to specific HPV peptides were associated with HPV clearance and regression to CIN (Kadish et al., 1997). On the other hand, de Gruijil et al. reported that T-cell proliferative responses to HPV16 E7 peptides correlated with persistence of HPV infection, but antigen-specific IL-2 production was associated with both virus clearance as well as progression of cervical lesions (de Gruijil et al., 1996).

A common clinical management strategy for CIN patients includes excisional or ablative treatment. However, follow-up studies indicate that a significant number of patients experience recurrence. At present no clear understanding exists regarding the development of pre-cancerous or cancerous growths, their recurrence, or disease-free status in the patients who have undergone ablative or excisional treatment for CIN. Better and improved strategies for effective diagnostics of HPV-associated pre-cancerous or cancerous growths and lesions is needed.

SUMMARY OF THE INVENTION

The present invention is based on the observation that a cell-mediated immune (CMI) response by patients infected with human papilloma virus (HPV) against E6 and/or E7 peptides of HPV is correlated with their prognosis. A cell-mediated immune response is indicative of a reduced risk for the development of pre-cancerous or cancerous growths in the genitourinary tract, particularly the cervix, than the risk for a patient who does not exhibit a cell-mediated immune response; in other words, a patient who exhibits a positive cell-mediate immune response to particular E6 and/or E7 peptides has a good prognosis with respect to the development of HPV-associated pre-cancerous or cancerous growths. Alternatively, a patient who exhibits no or a low CMI response to an E6 or E7 proteinaceous compound of HPV has a greater risk of a bad prognosis with respect to physiological effects as a result of HPV infection. Thus, the present invention encompasses compositions and methods for identifying patients at risk for HPV-related hyperproliferative conditions, including warts, CIN, and malignant growths or other pre-cancerous or cancerous growths; the invention is particularly suited to evaluating patients for recurrence of a hyperproliferative condition. As used herein, the terms "growth" and "lesion" are used interchangeably. Also, the term "pre-cancerous or cancerous growth" refers to HPV-associated growths. In addition to pre-cancerous or cancerous growths or lesions on the cervix, such growths or lesions may occur throughout the urogenitary tract and they include perineal, vulvar and penile growths or lesions. Patients for whom the methods may be applied include any mammals capable of HPV infection; in some embodiments, the patient is specifically contemplated to be a human, either male or female.

In some embodiments the present invention encompasses methods for determining the possibility of the development or recurrence of a pre-cancerous or cancerous growth in a patient infected with human papilloma virus. In some cases, the patient has been treated for the growth. The methods involve employing the following steps: obtaining a sample from the patient; incubating the sample with at least one E6 or E7 peptide of HPV; and assaying the sample for a cell-mediated immune (CMI) response against the peptide. A cell-mediated immune response against an E6 or E7 peptide, or a combination thereof indicates a reduced risk of recurrence as compared to a person who does not exhibit such a response. A pre-cancerous growth frequently observed with the development of cervical cancer is cervical intraepithelial neoplasia or CIN. In some embodiments of the invention, the method of the invention is used with respect to patients who have or had CIN of any stage (CIN 1, CIN 2, or CIN 3 or squamous intraepithelial lesions (SIL), low grade-SIL (L-SIL) and high grade SIL (H-SIL)). Furthermore, in other embodiments, the methods may be implemented with patients who have or had more severe stages of hyperproliferative growth than CIN, such as a malignancy or cancerous growth. As used in this application, the term "recurrence" refers to the appearance of a pre-cancerous or cancerous growth, or a reappearance of the first growth, or evidence thereof, after a first pre-cancerous or cancerous growth was reduced, eliminated, or treated. As used herein, the term "incubating" refers to exposing or contacting the sample with a composition that includes a peptide.

The claimed methods have applicability to human papilloma virus infections. The human papilloma virus may be a high grade or high risk type, such as HPV 16, 18, 31, 45, 56, or 58. In some embodiments, the human papilloma virus is HPV 16. In other embodiments, the human papilloma virus is a intermediate risk type, such as HPV 33, 35, 37, 51, 52, 59, 66, or 68. In still further embodiments the HPV is a low risk or low grade type associated with warts, such as type 6, 11, 26, 40, 42, 43, 44, 53, 55, 62, or 66.

The sample will include cells that give rise to a cell-mediated immune response. In some embodiments, the sample is a blood sample or serum sample, while in other embodiments, the sample is obtained by lavage, smear, or swab of the area suspected of infection or known to be infected, such as in the vaginal, cervical, or penile area. Peripheral blood mononuclear cells (PBMC) can render a cell-mediated immune response and any sample containing such cells can also be employed in methods of the invention. In some embodiments, it is contemplated that cells from a sample are incubated in media after they have been obtained but before they are assayed. It is contemplated that the sample may be incubated up to 1, 2, 3, 4, 5, 6, 7, 8, 9, 10, 11, 12 or more hours and up to 1, 2, 3, 4, 5, 6, or 7 days, and up to 1, 2, 3, 4, or 5 or more weeks and up to 1, 2, 3, 4, 5, 6, 7, 8, 9, 10, 11, or 12 months in media prior to assaying. It is also contemplated that the cells may be incubated in media and/or stored under conditions of sub-zero degrees centrigrade prior to assaying. The cells themselves or the cell culture supernatant (media, not intact cells) may be used for subsequent assays for a cell-mediated immune response. In some embodiments, the cells are incubated between 2 and 8 hours—in some cases for 6 hours—in media prior to performing intracellular cytokine analysis by flow cytometry. In other embodiments, the cells are incubated in media between 2 days and 20 days—in some cases 15 days—in media prior to performing chromium release assays to determine cytotoxic T lymphocyte (CTL) activity.

Methods of the present invention involve determining whether a patient exhibits a cell-mediated immune response against HPV peptides. In several embodiments, the peptides are E6 or E7 peptides meaning they have an amino acid sequence that is at least 90% identical over its length to a contiguous amino acid sequence in an E6 or E7 polypeptide. Specifically contemplated is the use of a peptide comprising 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more contiguous amino acids of SEQ ID NO:19 (E6 from HPV 16) or SEQ ID NO:20 (E7 from HPV 16). It is contemplated that in some embodiments that peptides of only one sequence are tested—for example, an E6 peptide or in another example, an E7 peptide—while in other embodiments, multiple sequences may be tested. In one embodiment, an E6 and an E7 peptide are employed in methods of the invention. In other embodiments, at least two E6 peptides (referring to at least two different E6 sequences), at least two E7 peptides (referring to at least two different E7 sequences), or both may be implemented. It is contemplated that 1, 2, 3, 4, 5, 6, 7, 8, 9, 10, 12, 13, 14, 15 or more E6 or E7 peptides may be employed, as well as any combination of E6 or E7 peptides thereof. In still further embodiments the E6 peptide is K9L, E10I, C10R, Q15L, V10C, P9L, P10I, Q20P, R16R, or G10S, or a combination thereof. In specific embodiments, the following E6 peptides are employed individually or as a cocktail that includes one or more of the following peptides: K9L, E10I, C10R, Q15L, or V10C. While in other embodiments, an E7 peptide is T10Q, M9T, D9L, Q19D, R9F, R9V, L9V, G10C, or D20C, or a combination thereof. In certain embodiments, the following E7 peptides are employed individually or as a cocktail Q19D, R9F, R9V, L9V, G10C. Furthermore, a cocktail that includes at least one E6 peptide and one E7 peptide from the following is contemplated: K9L, E10I, C10R, Q15L, V10C, Q19D, R9F, R9V, L9V, or G10C. In some embodiments, it is specifically contemplated that one or more peptides in the cocktails described above be excluded. It is also specifically contemplated that compositions discussed with respect to diagnostic methods of the invention may also be applied to preventative or therapeutic methods of the invention.

Methods of the invention concern a cell-mediated immune (CMI) response against human papilloma virus. There are different ways of identifying and evaluating a cell-mediated immune response (distinguished from a serum or antibody-mediated immune response). In one embodiment of the invention, T cell proliferation is measured. T-cell proliferation may be assayed by measuring incorporation of tritiated thymidine. A proliferative response of equal to or greater than 2.0 using an SI scale to at least one E6 or E7 peptide is considered positive and is indicative a patient with a reduced risk of recurrence of a pre-cancerous or cancerous growth or lesion. A proliferative response of equal to or greater than 3.0 using an SI scale to at least one E6 or E7 peptide is indicative of a cell mediated response, and thus, identifies a patient with a improved prognosis with respect to the development of pre-cancerous or cancerous growths. Alternatively, a patient who has an SI of less than 2.0, including an SI of zero, would be considered to have a low or no cell-mediated immune response to the E6 or E7 peptide(s) and would be considered as having an increased risk for the development or recurrence of pre-cancerous or cancerous growths.

A cell mediated response can also be measured using non-radioactive means such as an MTT (3-(4,5-dimethylthiazol-2-yl)-2,5-diphenyl tetrazolium bromide) dye or reduction assay, which is a colorimetric assay for live cells (T cell proliferation) (daCosta et al., 1999), or the alamar Blue assay, another colorimetric assay that measures IL-2-responding cells (Gloeckner et al., 2001; Kwack et al., 2000).

In another embodiment of the invention, assaying for a cell-mediated immune response involves measuring TH1 or TH2 cytokine amounts. Even if a patient does not exhibit a CMI response by a T-cell proliferation assay, an increased risk of recurrence may be associated with the production of a TH2 cytokine, such as IL-10. A reduced risk of recurrence is observed with a patient who exhibits production of a TH1 cytokine such as IFN-γ and IL-2 in response to an E6 and/or E7 peptide. In some examples, the amount of a TH1 cytokine is measured, such as IL-2, interferon (IFN) γ, tumor necrosis factor (TNF) α, or TNF-β, IL-3, IL-12, IL-15, IL-16, IL-17, or IL-18. In a specific embodiment, the amount of IL-18 is measured. In additional examples, the amount of a TH2 cytokine is measured, such as IL-1, IL-3, IL-4, IL-5, IL-6, IL-7, IL-9, IL-10, IL-11, IL-13 or IL-14.

Measuring a CMI response may be accomplished by an immunoassay, such as ELISA or a radioimmunoassay, or by flow-cytometry. In embodiments of the invention, a sample may be assayed more than once either as duplicate samples or by different assays. In some embodiments, more than one sample is obtained from the patient. The multiple samples may be the same type, for example, multiple blood sample, or they may be different types, for example, a blood sample and a vaginal swab.

Patients for whom the methods of the invention have applicability include patients not yet diagnosed with HPV but suspected of having HPV, patients once infected with HPV but no longer showing signs of HPV infection, patients known to be infected with HPV, patients with a pre-cancerous or cancerous growth on or around the cervix or other genitourinary area who may or may not know she is infected with HPV, patients whose pre-cancerous or cancerous growth(s) have been treated successfully or unsuccessfully, and patients who have had at least one recurrence of a pre-cancerous or cancerous growth(s). A pre-cancerous or cancerous growth or lesion refers to a hyperproliferative cells whose growth is not controlled, and includes pre-neoplasias, such as CIN and neoplasias—benign and malignant—involving squamous epithelial cells and atypical squamous cells of uncertain significance (ASCUS). It is contemplated that a patient have more than one growth or lesion. Treatment for any growths may involve surgery—ablative or excisional—as well as conventional cancer therapy and treatment against HPV. Such treatments include chemotherapy, radiation therapy, hormonal therapy, immunotherapy, administration of foscarnet, Thiovir, thiovir analogs (BioKeys), podofilox, podophyllin, trichloracetic acid (TCA), or 5-fluorouracil (5-FU), intralesional or intransal interferon, Imiquimid cream. Ablative techniques include the use of liquid nitrogen, electrocautery or electrodissection, surgical excision, or laser technology. A successful treatment refers to treatment that completely removes any signs of a growth, while a partially successful treatment refers to a treatment that affects the growth by reducing its size or growth rate, or preventing its enlargement, or reducing the number of growths if there is more than one. Patients once infected with HPV may at later times not exhibits signs of an HPV infection. However, it is believed such patients may still experience recurrence of a pre-cancerous or cancerous growth, like patients who have signs of continued HPV infection.

In some methods of the invention, the patient is evaluated to determine whether he/she is infected with HPV. In further embodiments, a serotyping of HPV is also included or is part of the initial determination of infection. In still further embodiments, the patient is evaluated to determine whether she has a pre-cancerous or cancerous growth, and if it is cancerous, whether the growth is benign or malignant.

Methods of the invention include embodiments in which the sample is obtained from the patient at least one month after treatment for a pre-cancerous or cancerous growth. The patient may have undergone treatment for at least one pre-cancerous or cancerous growth, such as by some form of ablation.

The present invention also includes therapeutic methods that may be employed with the diagnostic methods of the invention. In some embodiments of the invention, a patient is identified as having an increased risk for the development of recurrence of pre-cancerous or cancerous growths. A course of action that was not previously considered prior to the patient being identified as having that increased risk may be undertaken. In some embodiments, a patient who would not otherwise be treated is administered preventative treatment against pre-cancerous or cancerous growths or examined more frequently, or both. Preventative treatments are treatments administered in the absence of physiological signs of pre-cancerous or cancerous growths; "therapeutic treatment" encompasses medical treatment of a physiological condition that the patient exhibits. These preventative treatments include the use of therapeutic treatments for both HPV infection and HPV-associated pre-cancerous and cancerous growths, as described above.

In some embodiments, a preventative method to protect against or reduce the risk of the development of pre-cancerous and cancerous growths involves immunotherapy with HPV E6 and E7 peptides disclosed herein. If a patient is identified as having a low or no cell-mediated immune response against a particular E6 or E7 peptide, or against a combination of such peptides, a peptide or peptides of E6 or E7 sequence may be administered to the patient to elicit a CMI response. Such peptides include any E6 or E7 peptide, specifically including all or part of the peptides of Table 3. Also, peptides from an E6 or E7 polypeptide, such as those discussed with respect to diagnostic methods of the invention, may be employed in preventative methods as well. It is contemplated that the patient may be administered a composition containing one or more peptide sequences, and in some embodiments, with an adjuvant, liposome-based compound, or both. In further embodiments, the patient is administered peptides more than one time.

In some embodiments, there is a method for preventing recurrence of a pre-cancerous or cancerous growth, such as CIN, in a patient infected with HPV and treated for the growth by identifying a patient at risk for recurrence of an HPV-associated growth using methods disclosed herein; and, treating the patient to prevent or treat any recurrence. Treatment options may involve surgery—ablative or excisional—as well as conventional cancer therapy and treatment against HPV, as described above. In some embodiments, the treatment is the immunotherapy treatment involving at least one E6 or E7 peptide from HPV described above.

Furthermore, the present invention also encompasses kits for determining the possibility of recurrence of a pre-cancerous or cancer growth in a patient once infected with HPV and treated for the growth comprising, in a suitable container means, at least one E6 or E7 peptide from HPV and an antibody that allows the detection of a cell-mediated immune response against the peptide. In some embodiments, the antibody is attached to a non-reacting structure on which a sample can be applied, such as a plate with wells. In further embodiments, the non-reacting structure has membrane, which can be affixed or attached to the structure. In some embodiments, the kit can be used in an Enzyme-Linked Immunospot (ELISPOT) Assay to detect, and in some embodiments, quantitate, cytokine secreting cells. In still further embodiments, the kit includes an antibody against a TH1 or TH2 cytokine disclosed herein. Other embodiments include a detection reagent to detect the included antibody. A detection reagent is any compound that allows the detection of another compound, including reagents that allow detection visually, such as by a colorimetric detection reagent.

The use of the word "a" or "an" when used in conjunction with the term "comprising" in the claims and/or the specification may mean "one," but it is also consistent with the meaning of "one or more," "at least one," and "one or more than one."

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1A:
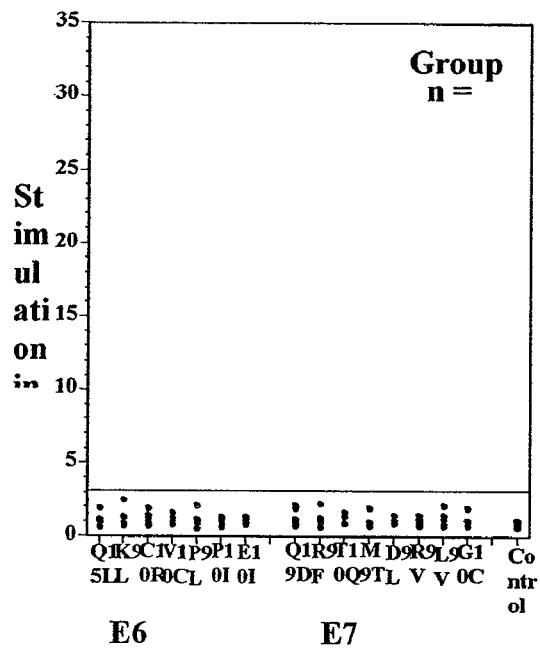
FIG. 1A-B. Proliferative responses to different E6 and E7 synthetic peptides by PBMC from women in four different study groups. Women in group 1 were normal ($CIN^{(-)}$/$HPV^{(-)}$, n=6), in group 2 were freshly diagnosed to be HPV-associated CIN ($CIN^{(+)}$/$HPV^{(+)}$, n=31), group 3 were disease-free post-treatment ($Recur^{(-)}$, n=22) and group 4 were with disease recurrence ($Recur^{(+)}$, n=10). PBMC from women in the four different groups were tested for proliferative responses to peptides from the E6 or E7 oncoproteins of HPV-16. A. The stimulation index (SI) values calculated as fold increase in $^3$[H]thymidine incorporation in peptide-treated samples over medium controls were shown for each patient for each of the peptides tested. B. A summary of positive responses to E6, E7, or both peptides by each group. Group numbers are indicated on the x-axis, while the percentage of positive responders in indicated on the y-axis.
Figure 1A:
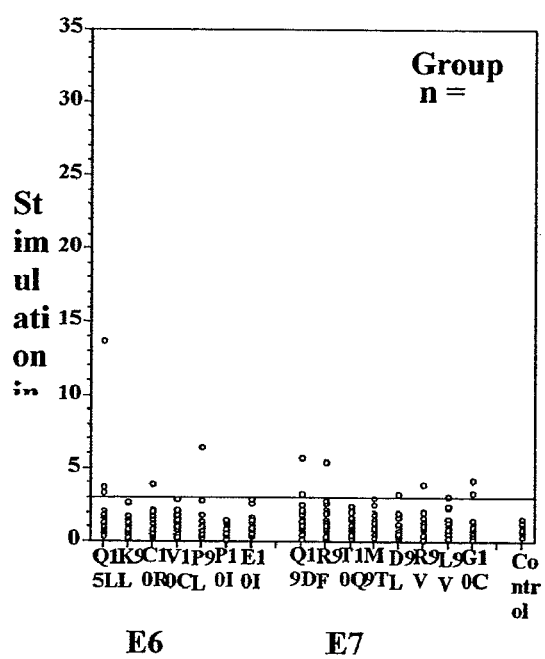
Figure 1A:
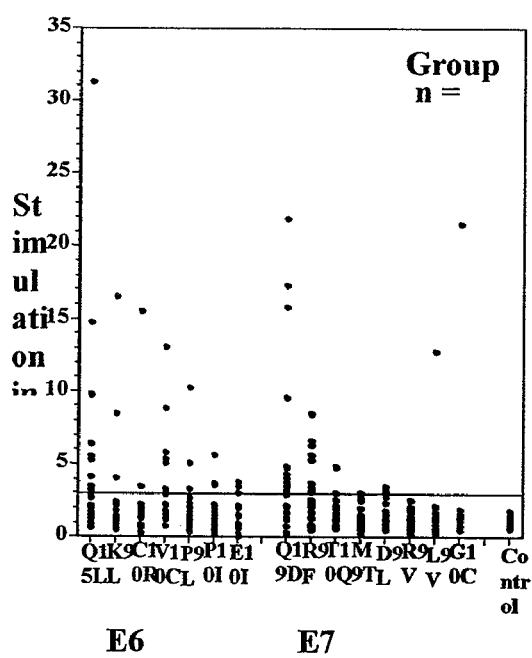
Figure 1A:
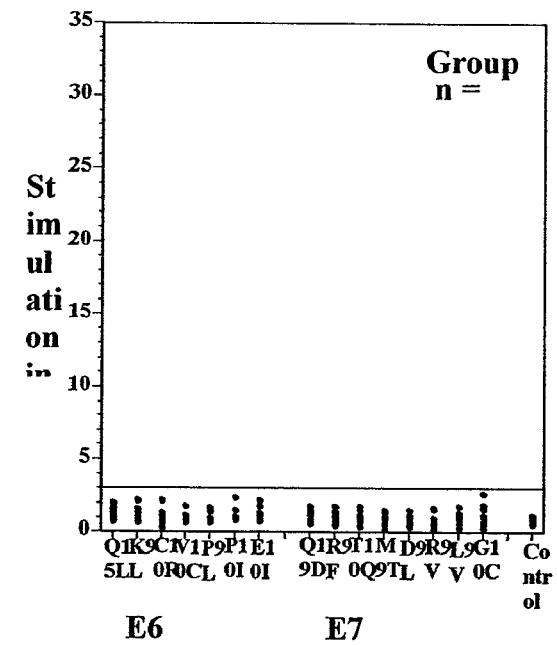
Figure 1:
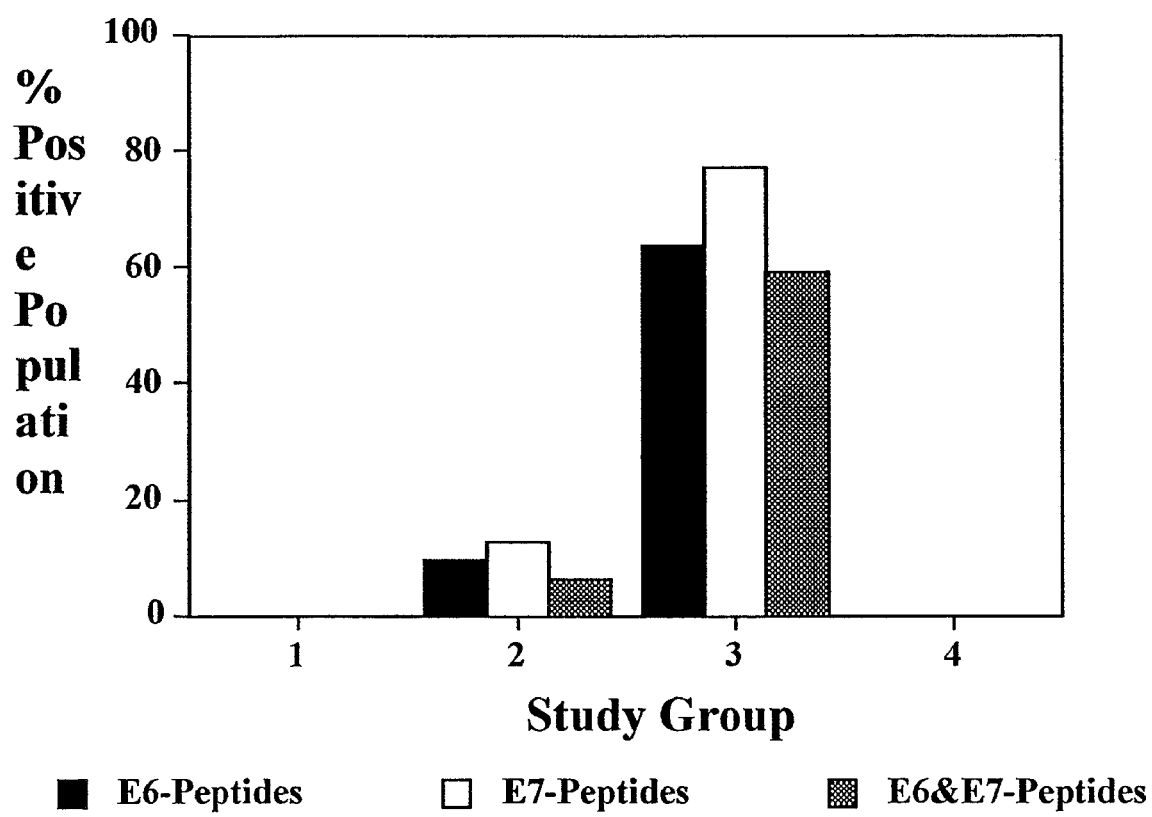

Human Papilloma Virus (HPV) infection is a major risk factor for cervical cancer, and there is an association between strong HPV-specific cell mediated immunity and less severe stages of CIN. A common clinical management strategy for CIN patients includes excisional or ablative treatment but, follow up studies indicate that a significant number of patients experience recurrence. At present no clear understanding exists regarding disease recurrence or disease free status in these patients. Prognostics and treatment or preventative therapies against CIN in both infected, uninfected and persons who undergo a recurrence of the disease are critical. Many treatment therapies have been tested and implemented but they have yet to eliminate the disease or prevent the recurrence of the disease. Significant number of patients experience recurrence of CIN but there are no means available to test the possibility and probability of recurrence.

The present invention provide a methods for determining the possibility of recurrence of CIN as a prognostic or biomarker in a patient infected by HPV and treated for CIN. The method involves the assay and analysis of a cell mediated immune response against peptides of HPV oncoproteins such as E6 and E7. The method also helps in identifying an HPV-infected patient at risk for recurrence of CIN. The present invention, further, makes use of targeted delivery systems, kits and immunotherapeutic measures to prevent the recurrence of CIN and to diagnose a patient with high risk of CIN.

I. HPV

Human papillomavirus (HPV) has been identified previously as an important cofactor in the development of stages of cervical neoplasia and cancer. Infection with HPV is however insufficient to cause cervical cancer. Not all women infected with HPV develop cervical cancer. Women are often treated for dysplastic cervical disease detected at the annual Pap Smear. Despite the existence of Pap smear screening, epidemiological investigations continue to implicate HPV as the single greatest risk factor for progression to cervical neoplasia and cancer. Cervical Intraepithelial Neoplasia (CIN) is a type of cervical cancer caused by Human Papilloma Virus (HPV). HPV is associated with development of cervical cancer, specifically HPV types 16, 18, 31, 45, 56 and 58 These comprise the High Grade Type/High Risk type of HPV. Intermediate grade/risk type include HPV 33, 35, 37, 51, 52, 59, 66, and 68. Other Low Grade Types/Low Risk Type associated with warts are types 6, 11, 26, 40, 42, 43, 44, 53, 54, 55, 62, and 66. These low grade types are not malignant in nature. The HPV genome is presented in an episomal (nonintegrated, circular) form in CIN, whereas the genome is often integrated into host DNA in invasive cervical carcinoma. The E6 and E7 oncoproteins, expressed by high-risk types of HPV, appear critical to the malignant transformation of cervical squamous epithelium, as a consequence of their ability to bind and then inactivate two important tumor suppressor genes, p53 and retinoblastoma gene (Rb). The inactivation of these tumor suppressor proteins appears to be a critical component of the oncogenic potential of HPV.

A. Diagnosis and Treatment of Cervical Cancer

Human Papillomavirus has been identified previously to be associated with the development of cervical carcinoma, a malignant condition which appears to be preceded by several stages of cervical intraepithelial neoplasia (CIN). Despite the existence of Pap smear screening, epidemiological investigations continue to implicate HPV as the single greatest risk factor for progression to CIN, many investigations continue to search for host and/or viral markers that will help identify women infected with HPV who are at risk for CIN. Equally important is the possibility of recurrence of CIN in patients who have been treated. Follow up studies in patients who have undergone excisional or ablative treatment indicate that a significant number of patients experience recurrence. Therefore, it is very important to be able to evaluate the possibility of recurrence of CIN. A prognosis of recurrence would allow a doctor to consider preventative options or therapy options.

Since the first reports linking HPV with cervical cancer appeared in the early 1980s (zur Hausen, 1994), it has become generally accepted that high-risk HPV types contribute to the initiation and progression of preinvasive intraepithelial lesions to carcinoma. Indeed, it has been noted that HPV infection culminates in a distinctive cytopathology in Pap smears, characterized by perinuclear clearing with associated nuclear atypia (Kurman et al, 1994). These HPV changes have been combined with mild dysplasia into the designation LSIL in the revised Bethesda terminology (Kurman and Solomon, 1994). The usefulness of HPV testing is complicated by the fact that there is a need to distinguish between low-risk (L-SIL) and high-risk (H-SIL) HPV types (only the latter pose a significant risk of association with dysplasia→carcinoma progression), and the actual risk of progression. In the former case, a new hybrid capture test for HPV distinguishes high-risk HPV types (Sherman et al., 1995; Poijak et al, 1999; Clavel et al., 2000). DNA image cytometry may be employed in addition to the methods of the invention to diagnose patients at risk for cervical lesions (Lorenzato et al., 2001).

1. Pap Smear

Over the last fifty years, Papanicolaou Smear ("Pap Smear") has become the cornerstone of efforts to reduce cervical cancer mortality. Pap Smear is effective because it identifies the earliest stages of cervical cancer. Current estimates are that 60-70 million Pap Smears are done in the U.S. each year. Pap Smear has thus become a norm in the detection of cervical cancer. In spite of its broad acceptance in the medical community, studies indicate that Pap Smear screenings will fail to detect from 50%-80% of low grade cancerous lesions, and even 15%-30% of high grade cancerous lesions.

The first step of any cytological diagnostic method is obtaining suitable Pap smear cells for review. In a conventional Pap smear test, a cytologist examines an exfoliative cell specimen, obtained by scraping some cells from the lining of the cervix, smearing the cells onto a slide and staining with Papanicolaou stain. The cytologist examines the stained smears for the presence of abnormal-looking cells that indicate the presence of a malignant condition. The term "malignant condition" refers to the presence of dysplasia including adenocarcinoma in situ (AIS), invasive carcinoma (CA), neoplastic, malignant or tumor cells or the like.

In the method of the invention an exfoliative cell specimen is obtained from a patient, who may or may not harbor a malignant condition. The specimen may be obtained by rotating a cervical sampling device, such as a swab, spatula, or cytobrush along a portion of cervix or vaginal mucosa to obtain a cell sample. A suitable specimen will contain endocervical cells with squamous and/or glandular cells.

The exfoliative cell specimen is generally smeared on the slide to provide a thin layer of the specimen on the surface of the slide. However, the manual observation of cellular abnormalities or the automated analysis of cytological material can be optimized by preparing "monolayers" of cells on the specimen slides. A "monolayer" is defined as substantially two-dimensional layer of uniformly distributed cellular material, predominantly made up of single cells and small clusters of cells.

When conducting Pap Smear screenings, a gynecologist collects exfoliated cells from the surface of the cervix and places them on slides that are sent to cytologists for further examination. Cytologists then review the cells placed on the slides and look for abnormal cells. If abnormal cells are found, the Pap Smear is considered to be positive. If no abnormal cells are found, the Pap Smear is considered to be negative. Pap Smear screening is generally recognized as a practical and economical procedure for the early detection of cervical cancer. In the present invention HPV positivity was determined by Virapap/Viratype assay (Technologies Inc., Gaithersburg, Md.).

2. Colposcopy

While the Pap Smear process is designed for initial screening, colposcopy and related procedures are generally used to confirm Pap Smear abnormalities and to grade cancerous and potential cancerous lesions. Since its introduction in 1925, colposcopy has acquired wide recognition as a follow-up clinical procedure for patients identified by Pap Smear screening as having possible cervical abnormalities. It is generally recognized that colposcopy is highly effective in evaluating patients with abnormal Pap Smears and has therefore become the standard of medical care in the Western world for this circumstance. It is estimated that approximately 4 million colposcopy examinations are currently performed in the U.S. each year.

3. Fluorescence Spectroscopy

Another method for detecting pre-cancerous and cancerous growths or lesions involves fluorescence spectroscopy, which has the capability to quickly, non-invasively and quantitatively probe the biochemical and morphological changes that occur as tissue becomes neoplastic. The altered biochemical and morphological state of the neoplastic tissue is reflected in the spectral characteristics of the measured fluorescence. U.S. Pat. Nos. 6,258,576 and 6,135,965 discuss diagnosis of cervical squamous intraepithelial (CIN) lesions and are specifically incorporated by reference.

4. Treatment of Precancerous and Cancerous Growth

A treatment is intended to effect an elimination, reduction or retardation of the growth. The cancerous growths can treated by excision or ablative procedures. In addition to the immunotherapy discussed in further detail below, the following treatments may be employed therapeutically or preventatively in methods of the invention.

i) Chemotherapy

Cancer therapies also include a variety of combination therapies with both chemical and radiation based treatments. Combination chemotherapies include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein transferase inhibitors, transplatinum, 5-fluorouracil, vincristin, vinblastin and methotrexate, or any analog or derivative variant of the foregoing.

ii) Radiotherapy

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic or diagnostic peptide or polynucleotide, or a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

iii) Genes

In yet another embodiment, the secondary treatment is a gene therapy in which a therapeutic polynucleotide is administered before, after, or at the same time as a chimeric polypeptide of the present invention. Delivery of a chimeric polypeptide in conjunction with a second vector encoding one of the following gene products will have a combined anti-hyperproliferative effect on target tissues. Alternatively, a single vector encoding both genes may be used. A variety of proteins are encompassed within the invention, including inducers of cell proliferation such as growth factor receptors, inhibitors of cellular proliferation such as tumor suppressors, and regulators of apoptosis.

iv) Ablative Procedures

A majority of persons with any cancer will generally undergo surgery of some type, which includes preventative, diagnostic or staging, curative and palliative surgery. Curative surgery is a pre-cancer or cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of pre-cancerous or cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

v) Other Agents

It is contemplated that other agents may be used in combination with the present invention to improve the therapeutic efficacy of treatment. These additional agents include immunomodulatory agents, agents that affect the upregulation of cell surface receptors and GAP junctions, cytostatic and differentiation agents, inhibitors of cell adhesion, or agents that increase the sensitivity of the hyperproliferative cells to apoptotic inducers. Immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines. It is further contemplated that the upregulation of cell surface receptors or their ligands such as Fas/Fas ligand, DR4 or DR5/TRAIL would potentiate the apoptotic inducing abilities of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyerproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

Hormonal therapy may also be used in conjunction with the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

v) Anti-viral Agents

A patient infected with HPV may be treated with anti-viral agents alone or in combination with anti-cancer therapies. An "anti-viral agent" refers to a composition that prevents or inhibits viral infection; prevents or inhibits the progression of a viral infection; reduces the infectivity of the virus; prevent, inhibits, or reduces the physiological symptoms of viral infection; prevents or reduces the incidence of viral activation; inhibits a cell that is a viral host; induces a host cell to undergo apoptosis; clears virus from all or part of the body; induces the virus to become inactive; or any combination of the above.

Agents used against HPV include administration of foscarnet, Thiovir, thiovir analogs (BioKeys), podofilox, podophyllin, trichloracetic acid (TCA), or 5-fluorouracil (5-FU), intralesional or intransal interferon, or Imiquimid cream. Other agents are disclosed in U.S. Pat. Nos. 6,245,568, 6,238,659, and 6,214,874.

II. Proteins and Peptides Selection, Synthesis and Use

In the present invention, peptides are employed in diagnostic and treatment methods. These peptides correspond to HPV 16 oncoproteins.

A. Proteinaceous Compositions

In certain embodiments, the present invention concerns novel compositions comprising at least one proteinaceous molecule as can be seen in peptides with SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15 SEQ ID NO: 16, SEQ ID NO: 17, SEQ ID NO: 18, SEQ ID NO: 19 and in the polypeptides of SEQ ID NO: 20 and SEQ ID NO: 21. As used herein, a "proteinaceous molecule," "proteinaceous composition," "proteinaceous compound," "proteinaceous chain" or "proteinaceous material" generally refers, but is not limited to, a protein of greater than about 200 amino acids or the full length endogenous sequence translated from a gene; a polypeptide of greater than about 100 amino acids; and/or a peptide of from about 3 to about 100 amino acids. All the "proteinaceous" terms described above may be used interchangeably herein.

In certain embodiments the size of the at least one proteinaceous molecule may comprise, but is not limited to, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1100, 1200, 1300, 1400, 1500, 1750, 2000, 2250, 2500 or greater amino molecule residues, and any range derivable therein. Peptides of the invention may comprise 4, 5, 6, 7, 8, 9, 10, 11, 12, 13, 14, 15, 16, 17, 18, 19 or up to 100 contiguous amino acids from SEQ ID NOS: 1-21, inclusive. SEQ ID NOS: 1 to 10 are peptides from the E6 polypeptide of HPV, while SEQ ID NOS: 11-19 are peptides from the E7 polypeptide of HPV. SEQ ID NOS: 20 and 21 are polypeptide sequences for HPV oncoproteins E6 and E7 respectively. The GenBank accession number for E6 in HPV 16 is AF327851 (SEQ ID NO:26), while the number for E7 in HPV 16 is U76404 (SEQ ID NO:27), which are both specifically incorporated by reference. Based on Table 3, it is understood that the peptides specifically contemplated as part of the invention include the following E6 peptides: K9L (aa 18-26 of SEQ ID NO:26), E10I (aa 23-34 of SEQ ID NO:26), C10R (aa 37-46 of SEQ ID NO:26), Q15L (aa 43-57 of SEQ ID NO:26), V10C (aa 49-58 of SEQ ID NO:26), P9L (aa 66-74 of SEQ ID NO:26), P10I (aa 102-111 of SEQ ID NO:26), Q20P (aa 97-116 of SEQ ID NO:26), R16R (aa 131-146 of SEQ ID NO:26), G10S (aa 141-150 of SEQ ID NO:26), or a combination thereof. Based on Table 3, it is further understood that the peptides specifically contemplated as part of the invention include the following E7 peptides: T10Q (aa 7-15 of SEQ ID NO:27), M9T (aa 12-20 of SEQ ID NO:27), D9L (aa 14-22 of SEQ ID NO:27), Q19D (aa 44-62 of SEQ ID NO:27), R9F (aa 49-57 of SEQ ID NO:27), R9V (aa 66-74 of SEQ ID NO:27), L9V (aa 82-90 of SEQ ID NO:27), G10C (aa 85-94 of SEQ ID NO:27), D20C (aa 75-94 of SEQ ID NO:27), or a combination thereof.

As used herein, an "amino molecule" refers to any amino acid, amino acid derivative or amino acid mimic as would be known to one of ordinary skill in the art. In certain embodiments, the residues of the proteinaceous molecule are sequential, without any non-amino molecule interrupting the sequence of amino molecule residues. In other embodiments, the sequence may comprise one or more non-amino molecule moieties. In particular embodiments, the sequence of residues of the proteinaceous molecule may be interrupted by one or more non-amino molecule moieties.

Accordingly, the term "proteinaceous composition" encompasses amino molecule sequences comprising at least one of the 20 common amino acids in naturally synthesized proteins, or at least one modified or unusual amino acid, including but not limited to those shown on Table 1 below.

TABLE 1

Modified and Unusual Amino Acids

| Abbr. | Amino Acid |
| --- | --- |
| Aad | 2-Aminoadipic acid |
| Baad | 3-Aminoadipic acid |
| Bala | β-alanine, β-Amino-propionic acid |
| Abu | 2-Aminobutyric acid |
| 4Abu | 4-Aminobutyric acid, piperidinic acid |
| Acp | 6-Aminocaproic acid |
| Ahe | 2-Aminoheptanoic acid |
| Aib | 2-Aminoisobutyric acid |
| Baib | 3-Aminoisobutyric acid |
| Apm | 2-Aminopimelic acid |
| Dbu | 2,4-Diaminobutyric acid |
| Des | Desmosine |
| Dpm | 2,2'-Diaminopimelic acid |
| Dpr | 2,3-Diaminopropionic acid |
| EtGly | N-Ethylglycine |
| EtAsn | N-Ethylasparagine |
| Hyl | Hydroxylysine |
| AHyl | allo-Hydroxylysine |
| 3Hyp | 3-Hydroxyproline |
| 4Hyp | 4-Hydroxyproline |
| Ide | Isodesmosine |
| AIle | allo-Isoleucine |
| MeGly | N-Methylglycine, sarcosine |
| MeIle | N-Methylisoleucine |
| MeLys | 6-N-Methyllysine |
| MeVal | N-Methylvaline |
| Nva | Norvaline |
| Nle | Norleucine |
| Orn | Ornithine |

In certain embodiments the proteinaceous composition comprises at least one protein, polypeptide or peptide. In further embodiments the proteinaceous composition comprises a biocompatible protein, polypeptide or peptide. As used herein, the term "biocompatible" refers to a substance which produces no significant untoward effects when applied to, or administered to, a given organism according to the methods and amounts described herein. Organisms include, but are not limited to, Such untoward or undesirable effects are those such as significant toxicity or adverse immunological reactions. In preferred embodiments, biocompatible protein, polypeptide or peptide containing compositions will generally be mammalian proteins or peptides or synthetic proteins or peptides each essentially free from toxins, pathogens and harmful immunogens.

Proteinaceous compositions may be made by any technique known to those of skill in the art, including the expression of proteins, polypeptides or peptides through standard molecular biological techniques, the isolation of proteinaceous compounds from natural sources, or the chemical synthesis of proteinaceous materials. The nucleotide and protein, polypeptide and peptide sequences for various genes have been previously disclosed, and may be found at computerized databases known to those of ordinary skill in the art. One such database is the National Center for Biotechnology Information's Genbank and GenPept databases (http://www.ncbi.nlm.nih.gov/). The coding regions for these known genes may be amplified and/or expressed using the techniques disclosed herein or as would be know to those of ordinary skill in the art. Alternatively, various commercial preparations of proteins, polypeptides and peptides are known to those of skill in the art.

In certain embodiments a proteinaceous compound may be purified. Generally, "purified" will refer to a specific or protein, polypeptide, or peptide composition that has been subjected to fractionation to remove various other proteins, polypeptides, or peptides, and which composition substantially retains its activity, as may be assessed, for example, by the protein assays, as would be known to one of ordinary skill in the art for the specific or desired protein, polypeptide or peptide.

It is contemplated that virtually any protein, polypeptide or peptide containing component may be used in the compositions and methods disclosed herein. However, it is preferred that the proteinaceous material is biocompatible. In certain embodiments, it is envisioned that the formation of a more viscous composition will be advantageous in that will allow the composition to be more precisely or easily applied to the tissue and to be maintained in contact with the tissue throughout the procedure. In such cases, the use of a peptide composition, or more preferably, a polypeptide or protein composition, is contemplated. Ranges of viscosity include, but are not limited to, about 40 to about 100 poise. In certain aspects, a viscosity of about 80 to about 100 poise is preferred.

B. Peptides Selection, Synthesis and Use

Peptide sequences corresponding to E6 and E7 oncoproteins of HPV 16 are selected on the basis of the amphipathic structures and information related to known T-cell epitopes described in literature.

The peptides of the invention can be synthesized in solution or on a solid support in accordance with conventional techniques. Various automatic synthesizers are commercially available and can be used in accordance with known protocols. Small synthetic peptide sequences, typically less than 100 residues in length, are conventionally prepared using stepwise solid-phase synthesis. Such solid phase synthesis makes use of an insoluble resin support for a growing oligomer. A sequence of subunits, destined to comprise a desired polymer, are reacted together in sequence on the support. A terminal amino acid is attached to the solid support in an initial reaction, either directly or through a keying agent. The terminal residue is reacted, in sequence, with a series of further residues such as amino acids or blocked amino acid moieties to yield a growing oligomer attached to the solid support through the terminal residue. At each stage in the synthetic scheme, unreacted reactant materials are washed out or otherwise removed from contact with the solid phase. The cycle is continued with a pre-selected sequence of residues until the desired polymer has been completely synthesized, but remains attached to the solid support. The polymer is then cleaved from the solid support and purified for use. The foregoing general synthetic scheme was developed by R. B. Merrifield for use in the preparation of certain peptides (Merrifield, 1986). These peptides can be synthesized either on a modified Vega 250 automatic peptide synthesizer (Vega Biochemicals, Tucson, Ariz.) or by the "bag method" as mentioned by Houghten (Houghten, 1985). Also see, for example, Stewart and Young, (1984); Tam et al., (1983); and Barany and Merrifield (1979), each incorporated herein by reference.

Short peptide sequences, or libraries of overlapping peptides, usually from about 6 up to about 35 to 50 amino acids, which correspond to the selected regions described herein, can be readily synthesized and then screened in screening assays designed to identify reactive peptides. Peptides with at least 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 50, 55, 60, 65, 70, 75, 80, 85, 90, 95 or up to about 100 contiguous amino acid residues of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19 and SEQ ID NO: 20, SEQ ID NO: 21 are contemplated by the present invention.

The compositions of the invention may include a peptide that has been modified to enhance its activity or to render it biologically protected. Biologically protected peptides have certain advantages over unprotected peptides when administered to human subjects and, as disclosed in U.S. Pat. No. 5,028,592, incorporated herein by reference, protected peptides often exhibit increased pharmacological activity.

Compositions for use in the present invention may also comprise peptides that include all L-amino acids, all D-amino acids, or a mixture thereof. The use of D-amino acids may confer additional resistance to proteases naturally found within the human body and are less immunogenic and can therefore be expected to have longer biological half lives.

III. Protein Purification

Peptides and proteins derived from HPV can be purified in many ways. Generally, "purified" will refer to a specific protein, polypeptide, or peptide composition that has been subjected to fractionation to remove various other proteins, polypeptides, or peptides, and which composition substantially retains its activity, as may be assessed, for example, by the protein assays, as described herein below, or as would be known to one of ordinary skill in the art for the desired protein, polypeptide or peptide.

Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present invention concern the purification, and in particular embodiments, the substantial purification, of an encoded protein or peptide, such as peptides derived from E6 and E7 oncoprotein. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition, that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (e.g., alter pH, ionic strength, and temperature.).

A particular type of affinity chromatography useful in the purification of carbohydrate containing compounds is lectin affinity chromatography. Lectins are a class of substances that bind to a variety of polysaccharides and glycoproteins. Lectins are usually coupled to agarose by cyanogen bromide. Conconavalin A coupled to Sepharose was the first material of this sort to be used and has been widely used in the isolation of polysaccharides and glycoproteins other lectins that have been include lentil lectin, wheat germ agglutinin which has been useful in the purification of N-acetyl glucosaminyl residues and *Helix pomatia* lectin. Lectins themselves are purified using affinity chromatography with carbohydrate ligands. Lactose has been used to purify lectins from castor bean and peanuts; maltose has been useful in extracting lectins from lentils and jack bean; N-acetyl-D galactosamine is used for purifying lectins from soybean; N-acetyl glucosaminyl binds to lectins from wheat germ; D-galactosamine has been used in obtaining lectins from clams and L-fucose will bind to lectins from lotus.

The matrix should be a substance that itself does not adsorb molecules to any significant extent and that has a broad range of chemical, physical and thermal stability. The ligand should be coupled in such a way as to not affect its binding properties. The ligand also should provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

IV. Nucleic Acids

A. Screening of DNA

In the present invention, screening of nucleic acids may be employed not only for screening a sample for infection but also, for detecting the possibility of recurrence of the disease. Screening procedures which rely on nucleic acid hybridization make it possible to isolate any gene sequence from any organism, provided the appropriate probe is available. Oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA done by the hybridization of the target DNA to that single probe in the mixture which is its complete complement (Wallace et al., 1981). The use of a probe or primer of between 13 and 100 nucleotides, preferably between 17 and 100 nucleotides in length, or in some aspects of the invention up to 1-2 kilobases or more in length, allows the formation of a duplex molecule that is both stable and selective. Molecules having complementary sequences over contiguous stretches greater than 20 bases in length are generally preferred, to increase stability and/or selectivity of the hybrid molecules obtained. One will generally prefer to design nucleic acid molecules for hybridization having one or more complementary sequences of 20 to 30 nucleotides, or even longer where desired. Such fragments may be readily prepared, for example, by directly synthesizing the fragment by chemical means or by introducing selected sequences into recombinant vectors for recombinant production.

Accordingly, the nucleotide sequences of the invention may be used for their ability to selectively form duplex molecules with complementary stretches of DNAs and/or RNAs or to provide primers for amplification of DNA or RNA from samples. Depending on the application envisioned, one would desire to employ varying conditions of hybridization to achieve varying degrees of selectivity of the probe or primers for the target sequence.

For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting specific mRNA transcripts. It is generally appreciated that conditions can be rendered more stringent by the addition of increasing amounts of formamide.

For certain applications, for example, site-directed mutagenesis, it is appreciated that lower stringency conditions are preferred. Under these conditions, hybridization may occur even though the sequences of the hybridizing strands are not perfectly complementary, but are mismatched at one or more positions. Conditions may be rendered less stringent by increasing salt concentration and/or decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Hybridization conditions can be readily manipulated depending on the desired results.

In other embodiments, hybridization may be achieved under conditions of, for example, 50 mM Tris-HCl (pH 8.3), 75 mM KCl, 3 mM $MgCl_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM $MgCl_2$, at temperatures ranging from approximately 40° C. to about 72° C.

In certain embodiments, it will be advantageous to employ nucleic acids of defined sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known that can be employed to provide a detection means that is visibly or spectrophotometrically detectable, to identify specific hybridization with complementary nucleic acid containing samples.

In general, it is envisioned that the probes or primers described herein will be useful as reagents in solution hybridization, as in PCR™, for detection of expression of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The conditions selected will depend on the particular circumstances (depending, for example, on the G+C content, type of target nucleic acid, source of nucleic acid, size of hybridization probe, etc.). Optimization of hybridization conditions for the particular application of interest is well known to those of skill in the art. After washing of the hybridized molecules to remove non-specifically bound probe molecules, hybridization is detected, and/or quantified, by determining the amount of bound label. Representative solid phase hybridization methods are disclosed in U.S. Pat. Nos. 5,843,663, 5,900,481 and 5,919,626. Other methods of hybridization that may be used in the practice of the present invention are disclosed in U.S. Pat. Nos. 5,849,481, 5,849,486 and 5,851,772. The relevant portions of these and other references identified in this section of the Specification are incorporated herein by reference.

B. Synthesis of DNA

The synthesis of DNA sequences is frequently the method of choice when the entire sequence of amino acid residues of the desired polypeptide product is known. When the entire sequence of amino acid residues of the desired polypeptides is not known, the direct synthesis of DNA sequences is not possible and the method of choice is the synthesis of cDNA sequences. Among the standard procedures for isolating cDNA sequences of interest is the formation of plasmid- or phage-carrying cDNA libraries which are derived from reverse transcription of mRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form.

1. Biochips

Methods of isolating arrays of biomolecules on various supports, referred to as biochips, have been developed and have been employed in DNA synthesis, sequencing, mutation studies, gene expression analysis and gene discovery. Biochips are useful in the present invention as it enables one to identify the markers for pathological states, in this case, HPV infection that may be of subsequent diagnostic value.

Use of a biochip involves the hybridization of a labeled molecule or pool of molecules to the targets immobilized on the biochip. The labeled molecules are normally cDNA copies of the mRNA content of a cell or tissue. In this instance the number of copies of each distinct type of cDNA reflects the number of copies of the corresponding. mRNA species in the initial isolate. In general terms, the intensity of hybridization to the target immobilized on the biochip is proportional to the concentration of the cDNA and thus measurement of hybridization intensity enables the relative amount of the mRNA in the initial isolate to be deduced. A relative amount of the same mRNA in two different mRNA isolated can be determined by comparing the intensities of hybridization to the same target spot between two samples. These measurements can be used to identify markers for particular cell types or pathological states that can be of subsequent diagnostic value. Alternatively, sharp increases in the abundance of particular mRNAs in a given disease state can indicate a possible target for drug attack, thereby providing novel therapeutic targets.

C. Nucleic Acid Amplification Reaction

Nucleic acid molecules can be detected using a variety of techniques, including amplification reactions. The present invention contemplates using these amplification reactions for detecting cell mediated immune response or to identify a patient who is infected with HPV and/or have a precancerous or cancerous growth. For example, a cell-mediated immune response can be detected by RT-PCR of a TH1 or TH2 cytokine disclosed herein.

1. Polymerase Chain Reaction (PCR™)

Nucleic acid used as a template for amplification is isolated from cells contained in the biological sample, according to standard methodologies (Sambrook, 1989). The nucleic acid may be genomic DNA or fractionated or whole cell RNA. Where RNA is used, it may be desired to convert the RNA to a cDNA.

Pairs of primers that selectively hybridize to nucleic acids corresponding to a $K_{ATP}$ channel protein or a mutant thereof are contacted with the isolated nucleic acid under conditions that permit selective hybridization. The term "primer," as defined herein, is meant to encompass any nucleic acid that is capable of priming the synthesis of a nascent nucleic acid in a template-dependent process. Typically, primers are oligonucleotides from ten to twenty base pairs in length, but longer sequences can be employed. Primers may be provided in double-stranded or single-stranded form, although the single-stranded form is preferred.

Once hybridized, the nucleic acid:primer complex is contacted with one or more enzymes that facilitate template-dependent nucleic acid synthesis. Multiple rounds of amplification, also referred to as "cycles," are conducted until a sufficient amount of amplification product is produced.

Next, the amplification product is detected. In certain applications, the detection may be performed by visual means. Alternatively, the detection may involve indirect identification of the product via chemiluminescence, radioactive scintigraphy of incorporated radiolabel or fluorescent label or even via a system using electrical or thermal impulse signals (Affymax technology).

A number of template dependent processes are available to amplify the marker sequences present in a given template sample. One of the best known amplification methods is the polymerase chain reaction (referred to as PCR™) which is described in detail in U.S. Pat. Nos. 4,683,195, 4,683,202 and 4,800,159, and each incorporated herein by reference in entirety.

Briefly, in PCR™, two primer sequences are prepared that are complementary to regions on opposite complementary strands of the marker sequence. An excess of deoxynucleoside triphosphates are added to a reaction mixture along with a DNA polymerase, e.g., Taq polymerase. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products and the process is repeated.

A reverse transcriptase PCR™ (RT-PCR™) amplification procedure may be performed in order to quantify the amount of mRNA amplified or to prepare cDNA from the desired mRNA. Methods of reverse transcribing RNA into cDNA are well known and described in Sambrook et al., 1989. Alternative methods for reverse transcription utilize thermostable, RNA-dependent DNA polymerases. These methods are described in WO 90/07641, filed Dec. 21, 1990, incorporated herein by reference. Polymerase chain reaction methodologies are well known in the art.

2. Other Nucleic Acid Amplification Reactions

Another method for amplification is the ligase chain reaction ("LCR"), disclosed in EPA No. 320 308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR™, bound ligated units dissociate from the target and then serve as "target sequences" for ligation of excess probe pairs. U.S. Pat. No. 4,883,750 describes a method similar to LCR for binding probe pairs to a target sequence.

Qbeta Replicase, described in PCT Application No. PCT/US87/00880, incorporated herein by reference, may also be used as still another amplification method in the present invention. In this method, a replicative sequence of RNA that has a region complementary to that of a target is added to a sample in the presence of an RNA polymerase. The polymerase will copy the replicative sequence that can then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention.

Strand Displacement Amplification (SDA) is another method of carrying out isothermal amplification of nucleic acids that involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases can be added as biotinylated derivatives for easy detection. A similar approach is used in SDA. Target specific sequences can also be detected using a cyclic probe reaction (CPR). In CPR, a probe having 3' and 5' sequences of non-specific DNA and a middle sequence of specific RNA is hybridized to DNA that is present in a sample. Upon hybridization, the reaction is treated with RNase H, and the products of the probe identified as distinctive products that are released after digestion. The original template is annealed to another cycling probe and the reaction is repeated.

Still another amplification methods described in GB Application No. 2 202 328, and in PCT Application No. PCT/US89/01025, each of which is incorporated herein by reference in its entirety, may be used in accordance with the present invention. In the former application, "modified" primers are used in a PCR™-like, template- and enzyme-dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS), including nucleic acid sequence based amplification (NASBA) and 3SR Gingeras et al., PCT Application WO 88/10315, incorporated herein by reference. In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by an RNA polymerase such as T7 or SP6. In an isothermal cyclic reaction, the RNA's are reverse transcribed into single stranded DNA, which is then converted to double stranded DNA, and then transcribed once again with an RNA polymerase such as T7 or SP6. The resulting products, whether truncated or complete, indicate target specific sequences.

Davey et al. (EPA No. 329 822, incorporated herein by reference in its entirety) disclose a nucleic acid amplification process involving cyclically synthesizing single-stranded RNA ("ssRNA"), ssDNA, and double-stranded DNA (dsDNA), which may be used in accordance with the present invention. The ssRNA is a template for a first primer oligonucleotide, which is elongated by reverse transcriptase (RNA-dependent DNA polymerase). The RNA is then removed from the resulting DNA:RNA duplex by the action of ribonuclease H (RNase H, an RNase specific for RNA in duplex with either DNA or RNA). The resultant ssDNA is a template for a second primer, which also includes the sequences of an RNA polymerase promoter (exemplified by T7 RNA polymerase) 5' to its homology to the template. This primer is then extended by DNA polymerase (exemplified by the large "Klenow" fragment of E. coli DNA polymerase I), resulting in a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Miller et al. (PCT Application WO 89/06700, incorporated herein by reference in its entirety) disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR" (Frohman, 1990, incorporated by reference).

Methods based on ligation of two (or more) oligonucleotides in the presence of nucleic acid having the sequence of the resulting "di-oligonucleotide", thereby amplifying the di-oligonucleotide, may also be used in the amplification step of the present invention.

D. Detection of Nucleic Acids

Following any amplification, it may be desirable to separate the amplification product from the template and/or the excess primer. The detection of nucleic acids may be useful in identifying a cell mediated immune response, a patient who is infected with HPV and/or a patient who has a precancerous or cancerous growth.

In one embodiment, amplification products are separated by agarose, agarose-acrylamide or polyacrylamide gel electrophoresis using standard methods (Sambrook et al., 1989). Separated amplification products may be cut out and eluted from the gel for further manipulation. Using low melting point agarose gels, the separated band may be removed by heating the gel, followed by extraction of the nucleic acid.

Separation of nucleic acids may also be effected by chromatographic techniques known in art. There are many kinds of chromatography which may be used in the practice of the present invention, including adsorption, partition, ion-exchange, hydroxylapatite, molecular sieve, reverse-phase, column, paper, thin-layer, and gas chromatography as well as HPLC.

In certain embodiments, the amplification products are visualized. A typical visualization method involves staining of a gel with ethidium bromide and visualization of bands under UV light. Alternatively, if the amplification products are integrally labeled with radio- or fluorometrically-labeled nucleotides, the separated amplification products can be exposed to x-ray film or visualized under the appropriate excitatory spectra.

In one embodiment, following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, or another binding partner carrying a detectable moiety.

In particular embodiments, detection is by Southern blotting and hybridization with a labeled probe. The techniques involved in Southern blotting are well known to those of skill in the art (see Sambrook et al., 1989). One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

HPV infection can also be detected by catalyzed signal amplified colorimetric DNA in situ hybridization (CSAC-ISH) (GenPoint system, DAKO) (Birner et al., 2001).

Other methods of nucleic acid detection that may be used in the practice of the instant invention are disclosed in U.S. Pat. Nos. 5,840,873, 5,843,640, 5,843,651, 5,846,708, 5,846,717, 5,846,726, 5,846,729, 5,849,487, 5,853,990, 5,853,992, 5,853,993, 5,856,092, 5,861,244, 5,863,732, 5,863,753, 5,866,331, 5,905,024, 5,910,407, 5,912,124, 5,912,145, 5,919,630, 5,925,517, 5,928,862, 5,928,869, 5,929,227, 5,932,413 and 5,935,791, each of which is incorporated herein by reference.

V. Cell Mediated Immunity (CMI):

Some methods of the claimed invention take advantage of T-cell responses by using them as a prognostic indicator of recurrence or as a preventative therapy against the development of CIN. More particularly, the methods assay for CMI responses to synthetic peptides from E6 and E7 oncoproteins of HPV 16. The E6 and E7 genes of HPV 16 are frequently co-expressed and are most abundant viral transcripts in biopsies from HPV 16 positive cervical carcinoma (Wettstein, 1990; Seedorf et al., 1987). There is a strong evidence that co-expression of both E6 and E7 open reading frames is necessary and sufficient for efficient malignant transformation of a variety of malignant transformation of a variety of mammalian cells (Munger et al., 1989). Furthermore, continued expression of the E6 and E7 regions of the viral genome appears to be required to maintain the malignant phenotype (von Knebel Doeberitz et al., 1988).

Most viral infections in immune competent mammals result in a cell-mediated immune response against the virus infected cells, the net effect being lysis of the cells. During viral infections, viral proteins are synthesized in the cell for inclusion into new viral particles. Some of those endogenous viral proteins also are degraded and transported into the class I antigen presentation pathway, where the foreign antigens associate with a class I MHC molecule. This peptide-MHC complex then is transported to the surface of the cells where the foreign peptide is presented, in the context of self MHC, to cytotoxic T cells (CTLs).

CTLs are antigen-specific effector cells. Lymphocyte surface marker studies can be used to assay for the presence of such T-cell surface markers using various procedures that are known to one of ordinary skill in the art, including the use of immunofluorescence and flow cytometry. Upon recognition of the antigen as foreign, the CTLs lyse the target cell either through molecular interactions that induce apoptosis, or through secretion of pore forming enzymes that create holes in the plasma membrane disrupting its integrity. Thus, the CTL-mediated immune response plays a significant role in the clearance of virally-infected cells.

The ability of CTL effector cells to lyse virus-infected target cells is regulated by genetic and antigenic restrictions. Target cells must carry a viral antigen that is the same or equivalent to that which originally induced the CTLs. The target cell and the induced CTL must also bear the same MHC class I molecule.

A. Peripheral Blood Mononuclear Cells (PBMCs)

Proliferative responses are obtained from PBMCs. There are a few methods by which one can isolate PBMCs.

Monocytes are separated from non-rosetting cells by adherence to glass or polyethylene tissue culture vessels with or without a collagen coating in RPMI 1640 with 20% fetal calf serum (FCS), determined to be free of endotoxin, by the limulus amebocyte lysis assay; alternatively, autologous serum, or 10% AB+ normal donor serum may be used as a serum source. Non-adherent cells are removed by gentle washing. Using these methods, adherent cells are usually >90% monocytes. If histological analysis suggests that there is significant contamination with T cells, B cells, or NK cells, these contaminating cells were removed by treatment with a cocktail of monoclonal antibodies, including anti-leu 5b, anti-leu 12 and anti-leu11b and baby rabbit complement (Rossen et al., 1985).

Monocytes are released after 1 hr or more adherence at 37° C. in a humidified 5% $CO_2$ atmosphere, for suspension culture in Teflon coated vessels (Crowe et al., 1987). In the case of cells plated on collagen coated surfaces, 1 mg/ml collagenase type 1 is added to the medium. Cells are released by incubation, for 15 min or more in calcium and magnesium free Dulbecco's phosphate buffered saline containing 5% FCS and EDTA. Incubations with EDTA are done on ice. A disposable cell scraper is used to help dislodge the cells. The dislodged cells are washed ×2 in calcium and magnesium free Dulbecco's PBS and cultured in RPMI 1640 and 10% AB+ human serum in Teflong; jars as described by Crowe et al. (1987).

Second strategy for isolating peripheral blood monocytes is Percoll density gradients to enrich the monocyte concentration in the non-rosetting population, according to Hester and Walker (1981). The monocyte-enriched population is treated with the monoclonal antibody cocktail, described above, and complement, to remove contaminating residual T cells, B cells and NK cells, as necessary. Monocytes are recovered by this method are cultured directly in Teflon coated vessels, without the 'activation' which necessarily occurs when monocytes become surface adherent. However, it is possible that the Percoll density gradient step, and/or the exposure antibodies and complement may also 'activate' these cells, possibly in a different manner.

A third approach to isolating peripheral blood monocytes is to take advantage of the retractile properties of monocytes to sort them on the basis of forward angle light scatter, using the high speed cell sorter function of the flow cytometer. This alternative has the potential to produce highly purified cells, which have not been influenced by contact with antibody or complement.

B. T-cell Responses

T-cell responses can be measured by a variety of protocols that are known to one of ordinary skill in the art. Some of these assays are described in fuller detail below.

1. $^3$[H]thymidine Incorporation Assay

The proliferative responses of PBMCs from different samples can be determined by the standard $^3$[H]thymidine incorporation assay as described in published articles (Nehete, 1996; Nehete, 1995). The significance of T-cell proliferative responses to the individual E6 and E7 peptides (in terms of stimulation index [SI]) can be calculated as the fold increase of $^3$[H]thymidine incorporation by cells exposed to the peptide over that by the control to which no peptide was added. An SI value of at least 2.0, including at least about 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0 or more, which are considered positive responses. Generally, an SI value is calculated by measuring the amount of radioactivity (cpm) in media from cells incubated with the peptide(s) and dividing by the amount of radioactivity in media from cells not incubated with peptide(s) (media alone).

2. Lysis Using $^{51}[Cr]$

Cell-mediated lympholysis (CML) can be used as an indication of T-cell response. Target cells can be labeled with radioactive chromium-51 ($^{51}[Cr]$) prior to exposure to effector cells. The amount of $^{51}[Cr]$ released into the media is proportional to the level of cell-mediated lysis.

3. γ-Interferon Production

Interferon gamma (γ-interferon), also called type II or immune interferon, is produced by T cells and NK cells. It is critical for the development of helper T cells. Because it is the primary macrophage-activating factor, it is a strong cytokine in cell-mediated immunity. γ-interferon increases the levels of MHC class I and MHC class II expression, which improves antigen presentation and other cognitive reactions. Furthermore, it amplifies the effects of TNF-α and raises expression levels of adhesion molecules on the surface of vascular endothelial cells, which leads to T cell adhesion and extravasation.

4. Tetramer Assay

Tetramer assays are well known to those of skill in the art. See Altman, 1996.

5. Cytokine Production

Cytokines are proteins that play important roles in the regulation of immune responses as well as in the differentiation pathways of different cell types. They have a critical function in T cell regulation and development, and these include γ-interferon, interleukin 1 (IL-1), IL-2, IL-4, IL-5, IL-6, IL-7, IL-10, IL-12, IL-13, IL-14, IL-15, lymphotoxin, MIF, TGF-β, TNF-α, and other chemotactic cytokines. The TH1 cytokines comprise IL-2, interferon (IFN) γ, tumor necrosis factor (TNF) α, or TNF-β, IL-3, IL-12, IL-15, IL-16, IL-17, or IL-18. TH2 cytokines include IL-1, IL-3, IL-4, IL-5, IL-6, IL-7, IL-9, IL-10, IL-11, IL-13, IL-14 or IL-18. Assays for cytokines are well known in the art of which some are disclosed herein 6. Cytokine Analysis Measurement of TH1 and TH2 cytokines can be done by ELISA, Radioimmunoassay (RIA) or Flow cytometry (FACS). The steps of various useful immunodetection methods have been described in the scientific literature, such as, e.g., Doolittle and Ben-Zeev, 1999; Gulbis and Galand, 1993; and De Jager et al., 1993, each incorporated herein by reference.

7. Immunoassays

In still further embodiments, the present invention concerns immunodetection methods for binding, purifying, removing, quantifying and/or otherwise generally detecting biological components protein(s), polypeptide(s) or peptide(s). In some embodiments immunoassays are used to detect a cell mediated immune response to HPV peptides. Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. The steps of various useful immunodetection methods have been described in the scientific literature, such as, e.g., Doolittle MH and Ben-Zeev O, 1999; Gulbis B and Galand P, 1993; and De Jager R et al., 1993, each incorporated herein by reference.

In general, the immunobinding methods include obtaining a sample suspected of containing protein, polypeptide and/or peptide, and contacting the sample with an antibody in accordance with the present invention, as the case may be, under conditions effective to allow the formation of immunocomplexes. For example, in the present invention, E6 and/or E7 peptides may be used to challenge the cells to elicit a T-cell response. The antibodies may be directed to cytokines produced as an outcome of the cell mediated response or to cytokine receptors on T-cells. Alternatively, an antibody against CD69 or CD45, or both, may be employed.

These methods include methods for purifying an protein, polypeptide and/or peptide from organelle, cell, tissue or organism's samples. In these instances, the antibody removes the protein, polypeptide and/or peptide component from a sample. The antibody will preferably be linked to a solid support, such as in the form of a column matrix, and the sample suspected of containing the protein, polypeptide and/or peptide antigenic component will be applied to the immobilized antibody. The unwanted components will be washed from the column, leaving the antigen immunocomplexed to the immobilized antibody to be eluted.

In terms of cytokine response detection, the biological sample analyzed may be any sample that is suspected of containing a cytokine, such as, for example, a tissue section or specimen, a homogenized tissue extract, a cell, an organelle, separated and/or purified forms of any of the above antigen-containing compositions, or even any biological fluid that comes into contact with the cell or tissue, including blood and/or serum, although tissue samples or extracts are preferred.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to, any antigens present. After this time, the sample-antibody composition, such as a tissue section, ELISA plate, dot blot or western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. U.S. patents concerning the use of such labels include U.S. Pat. Nos. 3,817,837; 3,850,752; 3,939,350; 3,996,345; 4,277, 437; 4,275,149 and 4,366,241, each incorporated herein by reference. Of course, one may find additional advantages through the use of a secondary binding ligand such as a second antibody and/or a biotin/avidin ligand binding arrangement, as is known in the art.

The antigen antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the antibody is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection designed by Charles Cantor uses two different antibodies. A first step biotinylated, monoclonal or polyclonal antibody is used to detect the target antigen(s), and a second step antibody is then used to detect the biotin attached to the complexed biotin. In that method the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. The method provides a useful means of identifying the population of women that are infected with HPV having cervical cancer or CIN.

Another means of determining whether a person infected by HPV has a precancerous growth or cancerous growth is by hybrid capture as shown in Birner et al. 2001 and Clavel et al., 2000, both incorporated by reference.

The immunodetection methods of the present invention have evident utility in the diagnosis and prognosis of conditions such as various diseases wherein a specific is expressed, such as a cancer specific gene product, etc. Here, a biological and/or clinical sample suspected of being infected with HPV that could lead to CIN is used. However, these embodiments also have applications to non-clinical samples, such as in the titering of antigen or antibody samples, for example in the selection of hybridomas.

a. ELISA

As detailed above, immunoassays, in their most simple and/or direct sense, are binding assays. Certain preferred immunoassays are the various types of enzyme linked immunosorbent assays (ELISAs) and/or radioimmunoassays (RIA) known in the art. Immunohistochemical detection using tissue sections is also particularly useful. However, it will be readily appreciated that detection is not limited to such techniques, and/or western blotting, dot blotting, FACS analyses, and/or the like may also be used.

In one exemplary ELISA, the antibodies directed to the product of cell mediated immune response (that comprises the antigen), in the present invention, are immobilized onto a selected surface exhibiting protein affinity, such as a well in a polystyrene microtiter plate. Then, a test composition suspected of containing the antigen, such as a clinical sample, is added to the wells. After binding and/or washing to remove non-specifically bound immune complexes, the bound antigen may be detected. Detection is generally achieved by the addition of another antibody that is linked to a detectable label. This type of ELISA is a simple "sandwich ELISA". Detection may also be achieved by the addition of a second antibody, followed by the addition of a third antibody that has binding affinity for the second antibody, with the third antibody being linked to a detectable label.

In another exemplary ELISA, the samples suspected of containing the antigen are immobilized onto the well surface and/or then contacted with the antibodies produced against the product of cell mediated immune response (that comprises the antigen). After binding and/or washing to remove non-specifically bound immune complexes, the bound antibodies are detected. Where the initial antibodies are linked to a detectable label, the immune complexes may be detected directly. Again, the immune complexes may be detected using a second antibody that has binding affinity for the first antibody, with the second antibody being linked to a detectable label.

Another ELISA in which the antigens are immobilized, involves the use of antibody competition in the detection. In this ELISA, labeled antibodies against an antigen are added to the wells, allowed to bind, and/or detected by means of their label. The amount of an antigen in an unknown sample is then determined by mixing the sample with the labeled antibodies against the antigen during incubation with coated wells. The presence of an antigen in the sample acts to reduce the amount of antibody against the antigen available for binding to the well and thus reduces the ultimate signal. This is also appropriate for detecting antibodies against an antigen in an unknown sample, where the unlabeled antibodies bind to the antigen-coated wells and also reduces the amount of antigen available to bind the labeled antibodies.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

b. Immunohistochemistry

The antibodies may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors, and/or is well known to those of skill in the art (Brown et al., 1990; Abbondanzo et al., 1990; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25-50 serial sections.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections.

c. Fluorescent Assorted Cell Spectroscopy:

Proteins may also be detected by flow cytometry as described in Fujishima et al, 1996. In the practice of the method, the cells are fixed and then incubated with a monoclonal antibody against the expressed protein to be detected. The bound antibodies are then contacted with labeled anti-IgG for example for detection. A typical label is FITC. The fluorescent intensity may then be measured by flow cytometer such as Ortho Cytron, Ortho diagnostics, or FACScan; Becton Dickinson.

FACS permits the separation of sub-populations of cells initially on the basis of their light scatter properties as they pass through a laser beam. The forward light scatter (FALS) is related to cell size and the right angle light scatter to cell density, cell contour and nucleo-cytoplasmic ratio. Since cells are tagged with fluorescent labeled antibody they can then be further characterized by fluorescence intensity and positive and negative windows set on the FACS to collect bright fluorescence and low fluorescence cells. Cells are sorted at a flow rate of about 3000 cells per second and collected in positive and negative cells.

d. Western Blots

The compositions of the present invention may find use in immunoblot or western blot analysis. The peptides may be used to challenge the cells to produce cytokines. The antibodies of the present invention may be used as high-affinity primary reagents for the identification of proteins immobilized onto a solid support matrix, such as nitrocellulose, nylon or combinations thereof. In conjunction with immunoprecipitation, followed by gel electrophoresis, these may be used as a single step reagent for use in detecting antigens against which secondary reagents used in the detection of the antigen cause an adverse background. This is especially useful when the antigens studied are immunoglobulins (precluding the use of immunoglobulins binding bacterial cell wall components), the antigens studied cross-react with the detecting agent, or they migrate at the same relative molecular weight as a cross-reacting signal.

Immunologically-based detection methods for use in conjunction with Western blotting include enzymatically-, radiolabel-, or fluorescently-tagged secondary antibodies against the protein moiety are considered to be of particular use in this regard.

VIII. Immunotherapy

Immunotherapy, as an approach to infection or cancer treatment, is based on the premise that tumor cells bear antigens provoking the production of specific antibodies and/or cytotoxic T lymphocytes (CTL).

A. Types of Immunotherapies:

Immunotherapies of cancer can broadly be classified as adoptive, passive and active, as described in the following sections.

1. Passive Immunotherapy

A number of different approaches for passive immunotherapy exist. They may be broadly categorized into the following: injection of antibodies alone; injection of antibodies coupled to toxins or chemotherapeutic agents; injection of antibodies coupled to radioactive isotopes; injection of anti-idiotype antibodies; and finally, purging of tumor cells in bone marrow.

Preferably, human monoclonal antibodies, are employed in passive immunotherapy, as they produce few or no side effects in the patient. However, their application is somewhat limited by their scarcity and have so far only been administered intralesionally. Human monoclonal antibodies to ganglioside antigens have been administered intralesionally to patients suffering from cutaneous recurrent melanoma (Irie & Morton, 1986). Regression was observed in six out of ten patients, following, daily or weekly, intralesional injections. In another study, moderate success was achieved from intralesional injections of two human monoclonal antibodies (Irie et al., 1989).

It may be favorable to administer more than one monoclonal antibody directed against two different antigens or even antibodies with multiple antigen specificity. Treatment protocols also may include administration of lymphokines or other immune enhancers as in Bajorin et al. (1988). The development of human monoclonal antibodies is described in further detail elsewhere in the specification.

2. Active Immunotherapy

In active immunotherapy, an antigenic peptide, polypeptide or protein, or an autologous or allogeneic tumor cell composition or "vaccine" is administered, generally with a distinct bacterial adjuvant (Ravindranath & Morton, 1991; Morton & Ravindranath, 1996; Morton et al., 1992; Mitchell et al., 1990; Mitchell et al., 1993). In melanoma immunotherapy, those patients who elicit high IgM response often survive better than those who elicit no or low IgM antibodies (Morton et al., 1992). IgM antibodies are often transient antibodies and the exception to the rule appears to be antiganglioside or anticarbohydrate antibodies.

3. Adoptive Immunotherapy

In adoptive immunotherapy, the patient's circulating lymphocytes, or tumor infiltrated lymphocytes, are isolated in vitro, activated by lymphokines such as IL-2 or transduced with genes for tumor necrosis, and readministered (Rosenberg et al., 1988; 1989). To achieve this, one would administer to an animal, or human patient, an immunologically effective amount of activated lymphocytes in combination with an adjuvant-incorporated antigenic peptide composition as described herein. The activated lymphocytes will most preferably be the patient's own cells that were earlier isolated and from a blood or tumor sample and activated (or "expanded") in vitro. This form of immunotherapy has produced several cases of regression of melanoma and renal carcinomas but the percentage of responders were few compared to those who did not respond.

B. Vaccination

The invention includes the use of immunotherapy using E6 and E7 peptides from HPV to induce or improve a cell-mediated immune response. This has particular significance for a patient who exhibits no or a low CMI response to E6 and/or E7 peptides from HPV. Peptides or polypeptides that comprises all or part of an amino acid sequence of SEQ ID NO:1 to 19 may be clinically very important as an effective vaccine for both the treatment and prevention of HPV-infection, including the prevention of HPV-associated pre-cancerous or cancerous growths, in inducing cell-mediated immune responses in patients.

Once produced, synthesized and/or purified, the peptides and polypeptides of the present invention may be prepared as a vaccine for administration to a patient. It also is contemplated that the peptides, polypeptides and vaccines of the invention may be combined with other vaccines or vaccine components, such as other additional antigens, to stimulate an immune response to the antigens. In this embodiment, preferred additional antigens are those implicated as being specific or preferentially expressed in cancers and hyperproliferative conditions. Additional antigens and vaccines that are contemplated for combination with the peptides, polypeptides and vaccines of the present invention included those described in U.S. Pat. Nos. 5,840,317 and 5,882,654, incorporated herein by reference.

One of ordinary skill in the art would be able to envision an array of potential therapeutic agents and delivery protocols for testing. For example, the potential anti-HPV and anti-tumor agents may be natural products or synthetic molecules of human design. Moreover, the model provides a vehicle for selection of effective agents from among a battery of known and novel compounds. The dosage and delivery mode of any particular potential therapeutic agent can be determined on the basis of well established guidelines for preparing pharmaceutically active compositions. The test compounds may be administered, for example, intravenously, intradermally, intramuscularly, topically, orally, or by any other pharmaceutically effective route. Using the animals produced by the method of the present invention, an investigator can now, for the first time, evaluate prophylactic and therapeutic agents against high risk human papillomavirus-induced disease, possibly including virus replication and transmission. These may include, among others, chemical-type pharmaceuticals, genetic therapies, antisense inhibitory strategies, or prophylactic or therapeutic vaccination. Many methods of evaluating the results of laboratory tests of proposed therapeutics are known.

Various adjuvants may be used to increase the immunological response, depending on the host species, including but not limited to, Freund's (complete and incomplete), mineral gels such as aluminum hydroxide, surface active substances such as lysolecithin, pluronic polyols, polyanions, peptides, oil emulsions, keyhold limpet hemocyanin, dinitrophenol, and potentially useful human adjuvants such as BCG (bacilli Calmetter-Guerin) and *Corynebacterium parvum*. In addition to use in immunotherapies of the invention, adjuvants may be used to enhance detection of a cell-mediated immune response in the context of the present invention.

C. Targeted Delivery Systems

To test for a virus-specific T cell response, in some embodiments of the claimed invention, HPV polypeptides or peptides can be delivered to target cells to express fragments of the viral protein on their surfaces for the purpose of eliciting a T-cell response. There are various methods of delivery including perfusion, transfection of an expression construct, viral vectors, and other means disclosed below.

1. Transfer by Perfusion

An embodiment of the claimed invention transfers peptides or a combination of peptides into cells via perfusion. Continuous perfusion of an expression construct or a viral construct also is contemplated. The amount of construct or peptide delivered in continuous perfusion can be determined by the amount of uptake that is desirable. The present invention discloses an example of perfusion whereby a cell culture with an initial concentration of $10^6$ cells/ml can first be labeled, washed, and then incubated with 100 μg of synthetic peptide for two hours.

2. Expression Vectors

The delivery of therapeutic peptides can be accomplished using expression vectors. In the present embodiment of the invention, HPV polypeptides and peptides are delivered to target cells through the use of expression constructs. Throughout this application, the term "expression construct" is meant to include any type of genetic construct containing a nucleic acid coding for an HPV polypeptide. A "viral vector" refers to an expression construct that is derived primarily from viral sequences. In order for the construct to effect expression, the polynucleotide encoding the HPV polynucleotide will be under the transcriptional control of a promoter. A "promoter" refers to a DNA sequence recognized by the synthetic machinery of the host cell, or by introduced synthetic machinery, that is required to initiate the specific transcription of a gene. The phrase "under transcriptional control" means that the promoter is in the correct location in relation to the polynucleotide to control RNA polymerase initiation and expression of the polynucleotide.

The term promoter will be used herein to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7-20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription.

The particular promoter that is employed to control the expression of an HPV polynucleotide is not believed to be critical, so long as it is capable of expressing the polynucleotide in the targeted cell. Thus, where a human cell is targeted, it is preferable to position the polynucleotide coding region adjacent to and under the control of a promoter that is capable of being expressed in a human cell. Generally speaking, such a promoter might include either a human or viral promoter. The use of other viral or mammalian cellular or bacterial phage promoters, which are well-known in the art, to achieve expression of polynucleotides is contemplated as well, provided that the levels of expression are sufficient to induce a T-cell response.

By employing a promoter with well-known properties, the level and pattern of expression of a polynucleotide following transfection can be optimized. For example, selection of a promoter that is active in specific cells, such as tyrosinase (melanoma), alpha-fetoprotein and albumin (liver tumors), CC10 (lung tumor) and prostate-specific antigen (prostate tumor) will permit tissue-specific expression of HPV polynucleotides. Further, selection of a promoter that is regulated in response to specific physiologic signals can permit inducible expression of the HPV polypeptide construct.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are frequently overlapping and contiguous, often seeming to have a very similar modular organization.

Additionally any promoter/enhancer combination (as per the Eukaryotic Promoter Data Base EPDB) could also be used to drive expression of an HPV polynucleotide construct. Use of a T3, T7 or SP6 cytoplasmic expression system is another possible embodiment. Eukaryotic cells can support cytoplasmic transcription from certain bacteriophage promoters if the appropriate bacteriophage polymerase is provided, either as part of the delivery complex or as an additional genetic expression vector.

In certain embodiments of the invention, the delivery of an expression vector in a cell may be identified in vitro or in vivo by including a marker in the expression vector. The marker would result in an identifiable change to the transfected cell permitting identification of expression. Usually, the inclusion of a drug selection marker aids in cloning and in the selection of transformants. Alternatively, enzymes such as herpes simplex virus thymidine kinase (tk) (eukaryotic) or chloramphenicol acetyltransferase (CAT) (prokaryotic) may be employed. Immunologic markers also can be employed. The selectable marker employed is not believed to be important, so long as it is capable of being expressed along with the polynucleotide encoding an HPV polypeptide. Further examples of selectable markers are well known to one of skill in the art.

One will typically include a polyadenylation signal to effect proper polyadenylation of the transcript. The nature of the polyadenylation signal is not believed to be crucial to the successful practice of the invention, and any such sequence may be employed. The inventor has employed the SV40 polyadenylation signal in that it was convenient and known to function well in the target cells employed. Also contemplated as an element of the expression construct is a terminator. These elements can serve to enhance message levels and to minimize read through from the construct into other sequences.

3. Viral Vectors

In some embodiments of the present invention, an expression construct comprises a virus or engineered construct derived from a viral genome. The ability of certain viruses to enter cells via receptor-mediated endocytosis and, in some cases, integrate into the host cell chromosomes, have made them attractive candidates for gene transfer in to mammalian cells. However, because it has been demonstrated that direct uptake of naked DNA, as well as receptor-mediated uptake of DNA complexes (discussed below), expression vectors need not be viral but, instead, may be any plasmid, cosmid, or phage construct that is capable of supporting expression of encoded genes in mammalian cells, such as pUC or Bluescript™ plasmid series.

a. Retroviruses

The retrovirus class is subdivided into three major groups: oncoviruses, such as murine leukemia virus; lentiviruses, and foamy viruses (spumaviruses). Retroviruses are single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants.

The retroviral genome contains three genes—gag, pol, and env—that encode capsid proteins, polymerase enzyme, and envelope components, respectively. A sequence found upstream from the gag gene, termed Ψ, functions as a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding an HPV polypeptide is inserted into the viral genome in the place of certain viral sequences to produce a virus that is replication-defective. Alternatively, a mutated HPV virus that is incapable of leading to HPV infection can be used. In order to produce virions, a packaging cell line containing the gag, pol and env genes but without the LTR and Ψ components is constructed (Mann, 1983). When a recombinant plasmid containing a human cDNA, together with the retroviral LTR and Ψ sequences, is introduced into this cell line (by calcium phosphate precipitation for example), the Ψ sequence allows the RNA transcript of the recombinant plasmid to be packaged into viral particles, which are then secreted into the culture media (Nicolas and Rubenstein, 1988; Mann, 1983). The media containing the recombinant retroviruses is then collected, optionally concentrated, and used for gene transfer. Retroviral vectors are able to infect a broad variety of cell types. However, integration and stable expression require the division of host cells (Paskind, 1975).

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux, 1989). Using antibodies against major histocompatibility complex class I and class II antigens, they demonstrated the infection of a variety of human cells that bore those surface antigens with an ecotropic virus in vitro (Roux, 1989).

b. Adenoviruses

Human adenoviruses are double-stranded DNA tumor viruses with genome sizes of approximate 36 kb (Tooze, 1981). As a model system for eukaryotic gene expression, adenoviruses have been widely studied and well characterized, which makes them an attractive system for development of adenovirus as a gene transfer system. This group of viruses is relatively simple to grow and manipulate, and exhibits a broad host range in vitro and in vivo. In lytically infected cells, adenoviruses are capable of shutting off host protein synthesis, directing cellular machineries to synthesize large quantities of viral proteins, and producing copious amounts of virus.

The E1 region of the genome includes E1A and E1B, which encode proteins responsible for transcription regulation of the viral genome, as well as a few cellular genes. E2 expression, including E2A and E2B, allows synthesis of viral replicative functions, e.g. DNA-binding protein, DNA polymerase, and a terminal protein that primes replication. E3 gene products prevent cytolysis by CTLs and tumor necrosis factor and appear to be important for viral propagation. Functions associated with the E4 proteins include DNA replication, late gene expression, and host cell shutoff. The late gene products include most of the virion capsid proteins, and these are expressed only after most of the processing of a single primary transcript from the major late promoter has occurred. The major late promoter (MLP) exhibits high efficiency during the late phase of the infection (Stratford-Perricaudet and Perricaudet, 1991).

As only a small portion of the viral genome appears to be required in cis (Tooze, 1981), adenovirus-derived vectors offer excellent potential for the substitution of large DNA fragments when used in connection with cell lines such as 293 cells. Ad5-transformed human embryonic kidney cell lines (Graham, 1977) have been developed to provide the essential viral proteins in trans. The characteristics of adenoviruses render them good candidates for use in targeting cells in vivo (Grunhaus and Horwitz, 1992).

Particular advantages of an adenovirus system for delivering foreign proteins to a cell include (i) the ability to substitute relatively large pieces of viral DNA by foreign DNA; (ii) the structural stability of recombinant adenoviruses; (iii) the safety of adenoviral administration to humans; and (iv) lack of any known association of adenoviral infection with cancer or malignancies; (v) the ability to obtain high titers of the recombinant virus; and (vi) the high infectivity of adenovirus.

In general, adenovirus gene transfer systems are based upon recombinant, engineered adenovirus that is rendered replication-incompetent by deletion of a portion of its genome, such as E1, and yet still retains its competency for infection. Sequences encoding relatively large foreign proteins can be expressed when additional deletions are made in the adenovirus genome. For example, adenoviruses deleted in both E1 and E3 regions are capable of carrying up to 10 kilobases of foreign DNA and can be grown to high titers in 293 cells (Stratford-Perricaudet and Perricaudet, 1991). Surprisingly persistent expression of transgenes following adenoviral infection has also been reported.

c. AAV Vectors

Adeno-associated virus (AAV) is an attractive vector system for use in the cell transduction of the present invention as it has a high frequency of integration and it can infect nondividing cells, thus making it useful for delivery of genes into mammalian cells, for example, in tissue culture (Muzyczka, 1992) or in vivo. AAV has a broad host range for infectivity (Lebkowski, 1988; McLaughlin, 1988; Laughlin, 1986; Tratschin, 1984). Details concerning the generation and use of rAAV vectors are described in U.S. Pat. Nos. 5,139,941 and 4,797,368, each incorporated herein by reference.

Studies demonstrating the use of AAV in gene delivery include LaFace et al. (1988); Zhou et al. (1993); Flotte et al. (1993); and Walsh et al. (1994). Recombinant AAV vectors have been used successfully for in vitro and in vivo transduction of marker genes (Kaplitt, 1994; Shelling and Smith, 1994; Yoder, 1994; Zhou, 1994; Samulski, 1989; Lebkowski, 1988; McLaughlin, 1988; Tratschin, 1985; Hermonat and Muzyczka, 1984) and genes involved in human diseases (Luo, 1994; Walsh, 1994; Wei, 1994; Flotte, 1992; Ohi, 1990). Recently, an AAV vector has been approved for phase I human trials for the treatment of cystic fibrosis.

AAV is a dependent parvovirus in that it requires coinfection with another virus (either adenovirus or a member of the herpes virus family) to undergo a productive infection in cultured cells (Muzyczka, 1992). In the absence of coinfection with helper virus, the wild type AAV genome integrates through its ends into human chromosome 19 where it resides in a latent state as a provirus (Samulski, 1991; Kotin, 1990). rAAV, however, is not restricted to chromosome 19 for integration unless the AAV Rep protein is also expressed (Shelling and Smith, 1994). When a cell carrying an AAV provirus is superinfected with a helper virus, the AAV genome is "rescued" from the chromosome or from a recombinant plasmid, and a normal productive infection is established (Muzyczka, 1992; Kotin, 1990; Samulski, 1989; McLaughlin, 1988).

Typically, recombinant AAV (rAAV) virus is made by cotransfecting a plasmid containing the gene of interest flanked by the two AAV terminal repeats (McLaughlin, 1988; Samulski, 1989; each incorporated herein by reference) and an expression plasmid containing the wild type AAV coding sequences without the terminal repeats, for example pIM45 (McCarty, 1991; incorporated herein by reference). The cells are also infected or transfected with adenovirus or plasmids carrying the adenovirus genes required for AAV helper function. rAAV virus stocks made in such fashion are contaminated with adenovirus which must be physically separated from the rAAV particles (for example, by cesium chloride density centrifugation). Alternatively, adenovirus vectors containing the AAV coding regions or cell lines containing the AAV coding regions and some or all of the adenovirus helper genes could be used (Clark, 1995; Yang, 1994). Cell lines carrying the rAAV DNA as an integrated provirus can also be used (Flotte, 1995).

d. Other Viral Vectors as Expression Constructs

Other viral vectors may be employed as expression constructs in the present invention. Vectors derived from viruses such as vaccinia virus (Coupar, 1988; Ridgeway, 1988; Baichwal and Sugden, 1986), and herpes viruses may also be employed. These viruses offer several attractive features for various mammalian cells (Horwich, 1990; Friedmann, 1989; Coupar, 1988; Ridgeway, 1988; Baichwal and Sugden, 1986).

With the recent recognition of defective hepatitis B viruses, new insight was gained into the structure-function relationship of different viral sequences. in vitro studies showed that the virus could retain the ability for helper-dependent packaging and reverse transcription despite the deletion of up to 80% of its genome (Horwich, 1990). This suggested that large portions of the genome could be replaced with foreign genetic material. The hepatotropism and persistence (integration) were particularly attractive properties for liver-directed gene transfer. Chang (1991) recently introduced the chloramphenicol acetyltransferase (CAT) gene into duck hepatitis B virus genome in the place of the polymerase, surface, and presurface coding sequences. It was cotransfected with wild-type virus into an avian hepatoma cell line. Culture media containing high titers of the recombinant virus were used to infect primary duckling hepatocytes. Stable CAT gene expression was detected for at least 24 days after transfection (Chang, 1991).

e. Non-viral Transfer Methods

Several non-viral methods for the transfer of expression vectors into cultured mammalian cells also are contemplated by the present invention. These include calcium phosphate precipitation (Graham and Van Der Eb, 1973; Chen and Okayama, 1987; Rippe, 1990) DEAE-dextran (Gopal, 1985), electroporation (Tur-Kaspa, 1986; Potter, 1984), direct microinjection (Harland and Weintraub, 1985), DNA-loaded liposomes (Nicolau and Sene, 1982; Fraley, 1979) and lipofectamine-DNA complexes, cell sonication (Fechheimer, 1987), gene bombardment using high velocity microprojectiles (Yang, 1990), polycations (Boussif, 1995), and receptor-mediated transfection (Wu and Wu, 1988; Wu and Wu, 1987). Some of these techniques may be successfully adapted for in vivo or ex vivo use.

D. Colloidal Dispersion Systems

Colloidal dispersion systems constitute targeted delivery vehicles. These dispersion systems include macromolecule complexes, nanocapsules complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2-4.0 µm can encapsulate a substantial percentage of an aqueous buffer containing large macromolecules. RNA, DNA and intact virions can be encapsulated within the aqueous interior and be delivered to cells in a biologically active form (Fraley, et al.). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high exigency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Manning, et al., *Biotechniques*, 6:682, 1988). The present embodiment of the invention propose that the synthetic peptides can be formulated as a liposome. The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14-18 carbon atoms, particularly from 16-18 carbon atoms, and is saturated. Illustrative phospholipids include egg phosphatidylcholine, dipalmitoylphosphatidylcholine and distearoylphosphatidylcholine.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

E. Pharmaceutical Compositions:

The present invention contemplates the use of the synthetic peptides in the form of a pharmaceutical compositions. In general a pharmaceutical composition will comprise an effective amount of one or more proteinaceous sequence, nucleic acid or antibody or additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that contains at least one proteinaceous sequence, nucleic acid or antibody or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The proteinaceous sequence, nucleic acid or antibody may comprise different types of carriers depending on whether it is to be administered in solid, liquid or aerosol form, and whether it need to be sterile for such routes of administration as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, rectally, topically, intratumorally, intramuscularly, intraperitoneally, subcutaneously, intravesicularlly, mucosally, intrapericardially, orally, topically, locally, using aerosol, injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The proteinaceous sequence, nucleic acid or antibody may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic: agents, such as, for example, sugars, sodium chloride or combinations thereof.

In other embodiments, one may use eye drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in preferred embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments the proteinaceous sequence, nucleic acid or antibody is prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain preferred embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Additional formulations which are suitable for other modes of administration include suppositories. Suppositories are solid dosage forms of various weights and shapes, usually medicated, for insertion into the rectum, vagina or urethra. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

Because peptides can be administered to a patient as an immunotherapy, lipids-based compositions are relevant to the invention. These are discussed in further detail below.

In certain embodiments, the present invention concerns a novel composition comprising one or more lipids associated with at least one peptide. A lipid is a substance that is characteristically insoluble in water and extractable with an organic solvent. Lipids include, for example, the substances comprising the fatty droplets that naturally occur in the cytoplasm as well as the class of compounds which are well known to those of skill in the art which contain long-chain aliphatic hydrocarbons and their derivatives, such as fatty acids, alcohols, amines, amino alcohols, and aldehydes. Of course, compounds other than those specifically described herein that are understood by one of skill in the art as lipids are also encompassed by the compositions and methods of the present invention.

A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof.

A. Lipid Types

A neutral fat may comprise a glycerol and a fatty acid. A typical glycerol is a three carbon alcohol. A fatty acid generally is a molecule comprising a carbon chain with an acidic moeity (e.g., carboxylic acid) at an end of the chain. The carbon chain may of a fatty acid may be of any length, however, it is preferred that the length of the carbon chain be of from about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, to about 30 or more carbon atoms, and any range derivable therein. However, a preferred range is from about 14 to about 24 carbon atoms in the chain portion of the fatty acid, with about 16 to about 18 carbon atoms being particularly preferred in certain embodiments. In certain embodiments the fatty acid carbon chain may comprise an odd number of carbon atoms, however, an even number of carbon atoms in the chain may be preferred in certain embodiments. A fatty acid comprising only single bonds in its carbon chain is called saturated, while a fatty acid comprising at least one double bond in its chain is called unsaturated.

Specific fatty acids include, but are not limited to, linoleic acid, oleic acid, palmitic acid, linolenic acid, stearic acid, lauric acid, myristic acid, arachidic acid, palmitoleic acid, arachidonic acid ricinoleic acid, tuberculosteric acid, lactobacillic acid. An acidic group of one or more fatty acids is covalently bonded to one or more hydroxyl groups of a glycerol. Thus, a monoglyceride comprises a glycerol and one fatty acid, a diglyceride comprises a glycerol and two fatty acids, and a triglyceride comprises a glycerol and three fatty acids.

A phospholipid generally comprises either glycerol or an sphingosine moiety, an ionic phosphate group to produce an amphipathic compound, and one or more fatty acids. Types of phospholipids include, for example, phophoglycerides, wherein a phosphate group is linked to the first carbon of glycerol of a diglyceride, and sphingophospholipids (e.g., sphingomyelin), wherein a phosphate group is esterified to a sphingosine amino alcohol. Another example of a sphingophospholipid is a sulfatide, which comprises an ionic sulfate group that makes the molecule amphipathic. A phopholipid may, of course, comprise further chemical groups, such as for example, an alcohol attached to the phosphate group. Examples of such alcohol groups include serine, ethanolamine, choline, glycerol and inositol. Thus, specific phosphoglycerides include a phosphatidyl serine, a phosphatidyl ethanolamine, a phosphatidyl choline, a phosphatidyl glycerol or a phosphotidyl inositol. Other phospholipids include a phosphatidic acid or a diacetyl phosphate. In one aspect, a phosphatidylcholine comprises a dioleoylphosphatidylcholine (a.k.a. cardiolipin), an egg phosphatidylcholine, a dipalmitoyl phosphalidycholine, a monomyristoyl phosphatidylcholine, a monopalmitoyl phosphatidylcholine, a monostearoyl phosphatidylcholine, a monooleoyl phosphatidylcholine, a dibutroyl phosphatidylcholine, a divaleroyl phosphatidylcholine, a dicaproyl phosphatidylcholine, a diheptanoyl phosphatidylcholine, a dicapryloyl phosphatidylcholine or a distearoyl phosphatidylcholine.

A glycolipid is related to a sphinogophospholipid, but comprises a carbohydrate group rather than a phosphate group attached to a primary hydroxyl group of the sphingosine. A type of glycolipid called a cerebroside comprises one sugar group (e.g., a glucose or galactose) attached to the primary hydroxyl group. Another example of a glycolipid is a ganglioside (e.g., a monosialoganglioside, a GM1), which comprises about 2, about 3, about 4, about 5, about 6, to about 7 or so sugar groups, that may be in a branched chain, attached to the primary hydroxyl group. In other embodiments, the glycolipid is a ceramide (e.g., lactosylceramide).

A steroid is a four-membered ring system derivative of a phenanthrene. Steroids often possess regulatory functions in cells, tissues and organisms, and include, for example, hormones and related compounds in the progestagen (e.g. progesterone), glucocoricoid (e.g., cortisol), mineralocorticoid (e.g., aldosterone), androgen (e.g., testosterone) and estrogen (e.g., estrone) families. Cholesterol is another example of a steroid, and generally serves structural rather than regulatory functions. Vitamin D is another example of a sterol, and is involved in calcium absorption from the intestine.

A terpene is a lipid comprising one or more five carbon isoprene groups. Terpenes have various biological functions, and include, for example, vitamin A, coenyzme Q and carotenoids (e.g., lycopene and β-carotene).

B. Charged and Neutral Lipid Compositions

In certain embodiments, a lipid component of a composition is uncharged or primarily uncharged. In one embodiment, a lipid component of a composition comprises one or more neutral lipids. In another aspect, a lipid component of a composition may be substantially free of anionic and cationic lipids, such as certain phospholipids (e.g., phosphatidyl choline) and cholesterol. In certain aspects, a lipid component of an uncharged or primarily uncharged lipid composition comprises about 95%, about 96%, about 97%, about 98%, about 99% or 100% lipids without a charge, substantially uncharged lipid(s), and/or a lipid mixture with equal numbers of positive and negative charges.

In other aspects, a lipid composition may be charged. For example, charged phospholipids may be used for preparing a lipid composition according to the present invention and can carry a net positive charge or a net negative charge. In a non-limiting example, diacetyl phosphate can be employed to confer a negative charge on the lipid composition, and stearylamine can be used to confer a positive charge on the lipid composition.

C. Making Lipids

Lipids can be obtained from natural sources, commercial sources or chemically synthesized, as would be known to one of ordinary skill in the art. For example, phospholipids can be from natural sources, such as egg or soybean phosphatidylcholine, brain phosphatidic acid, brain or plant phosphatidylinositol, heart cardiolipin and plant or bacterial phosphatidylethanolamine. In another example, lipids suitable for use according to the present invention can be obtained from commercial sources. For example, dimyristyl phosphatidylcholine ("DMPC") can be obtained from Sigma Chemical Co., dicetyl phosphate ("DCP") is obtained from K & K Laboratories (Plainview, N.Y.); cholesterol ("Chol") is obtained from Calbiochem-Behring; dimyristyl phosphatidylglycerol ("DMPG") and other lipids may be obtained from Avanti Polar Lipids, Inc. (Birmingham, Ala.). In certain embodiments, stock solutions of lipids in chloroform or chloroform/methanol can be stored at about −20° C. Preferably, chloroform is used as the only solvent since it is more readily evaporated than methanol.

D. Lipid Composition Structures

In a preferred embodiment of the invention, the peptide may be associated with a lipid. A peptide associated with a lipid may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure. A lipid or lipid/chimeric polypeptide associated composition of the present invention is not limited to any particular structure. For example, they may also simply be interspersed in a solution, possibly forming aggregates which are not uniform in either size or shape. In another example, they may be present in a bilayer structure, as micelles, or with a "collapsed" structure. In another non-limiting example, a lipofectamine (Gibco BRL)-chimeric polypeptide or Superfect (Qiagen)-chimeric polypeptide complex is also contemplated.

In certain embodiments, a lipid composition may comprise about 1%, about 2%, about 3%, about 4% about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 100%, or any range derivable therein, of a particular lipid, lipid type or non-lipid component such as a drug, protein, sugar, nucleic acids or other material disclosed herein or as would be known to one of skill in the art. In a non-limiting example, a lipid composition may comprise about 10% to about 20% neutral lipids, and about 33% to about 34% of a cerebroside, and about 1% cholesterol. In another non-limiting example, a liposome may comprise about 4% to about 12% terpenes, wherein about 1% of the micelle is specifically lycopene, leaving about 3% to about 11% of the liposome as comprising other terpenes; and about 10% to about 35% phosphatidyl choline, and about 1% of a drug. Thus, it is contemplated that lipid compositions of the present invention may comprise any of the lipids, lipid types or other components in any combination or percentage range.

1. Emulsions

A lipid may be comprised in an emulsion. A lipid emulsion is a substantially permanent heterogenous liquid mixture of two or more liquids that do not normally dissolve in each other, by mechanical agitation or by small amounts of additional substances known as emulsifiers. Methods for preparing lipid emulsions and adding additional components are well known in the art (e.g., Modern Pharmaceutics, 1990, incorporated herein by reference).

For example, one or more lipids are added to ethanol or chloroform or any other suitable organic solvent and agitated by hand or mechanical techniques. The solvent is then evaporated from the mixture leaving a dried glaze of lipid. The lipids are resuspended in aqueous media, such as phosphate buffered saline, resulting in an emulsion. To achieve a more homogeneous size distribution of the emulsified lipids, the mixture may be sonicated using conventional sonication techniques, further emulsified using microfluidization (using, for example, a Microfluidizer, Newton, Mass.), and/or extruded under high pressure (such as, for example, 600 psi) using an Extruder Device (Lipex Biomembranes, Vancouver, Canada).

2. Micelles

A lipid may be comprised in a micelle. A micelle is a cluster or aggregate of lipid compounds, generally in the form of a lipid monolayer, and may be prepared using any micelle producing protocol known to those of skill in the art (e.g., Canfield et al., 1990; El-Gorab et al, 1973; Shinoda et al., 1963; and Fendler et al., 1975, each incorporated herein by reference). For example, one or more lipids are typically made into a suspension in an organic solvent, the solvent is evaporated, the lipid is resuspended in an aqueous medium, sonicated and then centrifuged.

3. Liposomes

In particular embodiments, a lipid comprises a liposome. A "liposome" is a generic term encompassing a variety of single and multilamellar lipid vehicles formed by the generation of enclosed lipid bilayers or aggregates. Liposomes may be characterized as having vesicular structures with a bilayer membrane, generally comprising a phospholipid, and an inner medium that generally comprises an aqueous composition.

A multilamellar liposome has multiple lipid layers separated by aqueous medium. They form spontaneously when lipids comprising phospholipids are suspended in an excess of aqueous solution. The lipid components undergo self-rearrangement before the formation of closed structures and entrap water and dissolved solutes between the lipid bilayers (Ghosh and Bachhawat, 1991). Lipophilic molecules or molecules with lipophilic regions may also dissolve in or associate with the lipid bilayer.

In certain less preferred embodiments, phospholipids from natural sources, such as egg or soybean phosphatidylcholine, brain phosphatidic acid, brain or plant phosphatidylinositol, heart cardiolipin and plant or bacterial phosphatidylethanolamine are preferably not used as the primary phosphatide, i.e., constituting 50% or more of the total phosphatide composition or a liposome, because of the instability and leakiness of the resulting liposomes.

In particular embodiments, a lipid and/or chimeric polypeptide may be, for example, encapsulated in the aqueous interior of a liposome, interspersed within the lipid bilayer of a liposome, attached to a liposome via a linking molecule that is associated with both the liposome and the chimeric polypeptide, entrapped in a liposome, complexed with a liposome, etc.

a. Making Liposomes

A liposome used according to the present invention can be made by different methods, as would be known to one of ordinary skill in the art. Phospholipids can form a variety of structures other than liposomes when dispersed in water, depending on the molar ratio of lipid to water. At low ratios the liposome is the preferred structure.

For example, a phospholipid (Avanti Polar Lipids, Alabaster, Ala.), such as for example the neutral phospholipid dioleoylphosphatidylcholine (DOPC), is dissolved in tert-butanol. The lipid(s) is then mixed with the chimeric polypeptide, and/or other component(s). Tween 20 is added to the lipid mixture such that Tween 20 is about 5% of the composition's weight. Excess tert-butanol is added to this mixture such that the volume of tert-butanol is at least 95%. The mixture is vortexed, frozen in a dry ice/acetone bath and lyophilized overnight. The lyophilized preparation is stored at −20° C. and can be used up to three months. When required the lyophilized liposomes are reconstituted in 0.9% saline. The average diameter of the particles obtained using Tween 20 for encapsulating the chimeric polypeptide is about 0.7 to about 1.0 µm in diameter.

Alternatively, a liposome can be prepared by mixing lipids in a solvent in a container, e.g., a glass, pear-shaped flask. The container should have a volume ten-times greater than the volume of the expected suspension of liposomes. Using a rotary evaporator, the solvent is removed at approximately 40° C. under negative pressure. The solvent normally is removed within about 5 min. to 2 hours, depending on the desired volume of the liposomes. The composition can be dried further in a desiccator under vacuum. The dried lipids generally are discarded after about 1 week because of a tendency to deteriorate with time.

Dried lipids can be hydrated at approximately 25-50 mM phospholipid in sterile, pyrogen-free water by shaking until all the lipid film is resuspended. The aqueous liposomes can be then separated into aliquots, each placed in a vial, lyophilized and sealed under vacuum.

In other alternative methods, liposomes can be prepared in accordance with other known laboratory procedures (e.g., see Bangham et al., 1965; Gregoriadis, 1979; Deamer and Uster 1983, Szoka and Papahadjopoulos, 1978, each incorporated herein by reference in relevant part). These methods differ in their respective abilities to entrap aqueous material and their respective aqueous space-to-lipid ratios.

The dried lipids or lyophilized liposomes prepared as described above may be dehydrated and reconstituted in a solution of inhibitory peptide and diluted to an appropriate concentration with an suitable solvent, e.g., DPBS. The mixture is then vigorously shaken in a vortex mixer. Unencapsulated additional materials, such as agents including but not limited to hormones, drugs, nucleic acid constructs and the like, are removed by centrifugation at 29,000×g and the liposomal pellets washed. The washed liposomes are resuspended at an appropriate total phospholipid concentration, e.g., about 50-200 mM. The amount of additional material or active agent encapsulated can be determined in accordance with standard methods. After determination of the amount of additional material or active agent encapsulated in the liposome preparation, the liposomes may be diluted to appropriate concentrations and stored at 4° C. until use. A pharmaceutical composition comprising the liposomes will usually include a sterile, pharmaceutically acceptable carrier or diluent, such as water or saline solution.

The size of a liposome varies depending on the method of synthesis. Liposomes in the present invention can be a variety of sizes. In certain embodiments, the liposomes are small, e.g., less than about 100 nm, about 90 nm, about 80 nm, about 70 nm, about 60 nm, or less than about 50 nm in external diameter. In preparing such liposomes, any protocol described herein, or as would be known to one of ordinary skill in the art may be used. Additional non-limiting examples of preparing liposomes are described in U.S. Pat. Nos. 4,728,578, 4,728,575, 4,737,323, 4,533,254, 4,162,282, 4,310,505, and 4,921,706; International Applications PCT/US85/01161 and PCT/US89/05040; U.K. Patent Application GB 2193095 A; Mayer et al., 1986; Hope et al., 1985; Mayhew et al. 1987; Mayhew et al., 1984; Cheng et al., 1987; and Gregoriadis, 1984, each incorporated herein by reference).

A liposome suspended in an aqueous solution is generally in the shape of a spherical vesicle, having one or more concentric layers of lipid bilayer molecules. Each layer consists of a parallel array of molecules represented by the formula XY, wherein X is a hydrophilic moiety and Y is a hydrophobic moiety. In aqueous suspension, the concentric layers are arranged such that the hydrophilic moieties tend to remain in contact with an aqueous phase and the hydrophobic regions tend to self-associate. For example, when aqueous phases are present both within and without the liposome, the lipid molecules may form a bilayer, known as a lamella, of the arrangement XY-YX. Aggregates of lipids may form when the hydrophilic and hydrophobic parts of more than one lipid molecule become associated with each other. The size and shape of these aggregates will depend upon many different variables, such as the nature of the solvent and the presence of other compounds in the solution.

The production of lipid formulations often is accomplished by sonication or serial extrusion of liposomal mixtures after (I) reverse phase evaporation (II) dehydration-rehydration (II) detergent dialysis and (IV) thin film hydration. In one aspect, a contemplated method for preparing liposomes in certain embodiments is heating sonicating, and sequential extrusion of the lipids through filters or membranes of decreasing pore size, thereby resulting in the formation of small, stable liposome structures. This preparation produces liposomal/chimeric polypeptide or liposomes only of appropriate and uniform size, which are structurally stable and produce maximal activity. Such techniques are well-known to those of skill in the art (see, for example Martin, 1990).

Once manufactured, lipid structures can be used to encapsulate compounds that are toxic (e.g., chemotherapeutics) or labile (e.g., nucleic acids) when in circulation. The physical characteristics of liposomes depend on pH, ionic strength and/or the presence of divalent cations. Liposomes can show low permeability to ionic and/or polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and/or results in an increase in permeability to ions, sugars and/or drugs. Liposomal encapsulation has resulted in a lower toxicity and a longer serum half-life for such compounds (Gabizon et al., 1990).

Liposomes interact with cells to deliver agents via four different mechanisms: Endocytosis by phagocytic cells of the reticuloendothelial system such as macrophages and/or neutrophils; adsorption to the cell surface, either by nonspecific weak hydrophobic and/or electrostatic forces, and/or by specific interactions with cell-surface components; fusion with the plasma cell membrane by insertion of the lipid bilayer of the liposome into the plasma membrane, with simultaneous release of liposomal contents into the cytoplasm; and/or by transfer of liposomal lipids to cellular and/or subcellular membranes, and/or vice versa, without any association of the liposome contents. Varying the liposome formulation can alter which mechanism is operative, although more than one may operate at the same time.

Numerous disease treatments are using lipid based gene transfer strategies to enhance conventional or establish novel therapies, in particular therapies for treating hyperproliferative diseases. Advances in liposome formulations have improved the efficiency of gene transfer in vivo (Templeton et al., 1997) and it is contemplated that liposomes are prepared by these methods. Alternate methods of preparing lipid-based formulations for nucleic acid delivery are described (WO 99/18933).

In another liposome formulation, an amphipathic vehicle called a solvent dilution microcarrier (SDMC) enables integration of particular molecules into the bi-layer of the lipid vehicle (U.S. Pat. No. 5,879,703). The SDMCs can be used to deliver lipopolysaccharides, polypeptides, nucleic acids and the like. Of course, any other methods of liposome preparation can be used by the skilled artisan to obtain a desired liposome formulation in the present invention.

b. Targeting Ligands

The targeting ligand can be either anchored in the hydrophobic portion of the complex or attached to reactive terminal groups of the hydrophilic portion of the complex. The targeting ligand can be attached to the liposome via a linkage to a reactive group, e.g., on the distal end of the hydrophilic polymer. Preferred reactive groups include amino groups, carboxylic groups, hydrazide groups, and thiol groups. The coupling of the targeting ligand to the hydrophilic polymer can be performed by standard methods of organic chemistry that are known to those skilled in the art. In certain embodiments, the total concentration of the targeting ligand can be from about 0.01 to about 10% mol.

Targeting ligands are any ligand specific for a characteristic component of the targeted region. Preferred targeting ligands include proteins such as polyclonal or monoclonal antibodies, antibody fragments, or chimeric antibodies, enzymes, or hormones, or sugars such as mono-, oligo- and poly-saccharides (see, Heath et al., 1986) For example, disialoganglioside GD2 is a tumor antigen that has been identified neuroectodermal origin tumors, such as neuroblastoma, melanoma, small-cell lung carcenoma, glioma and certain sarcomas (Mujoo et al., 1986, Schulz et al., 1984). Liposomes containing anti-disialoganglioside GD2 monoclonal antibodies have been used to aid the targeting of the liposomes to cells expressing the tumor antigen (Montaldo et al., 1999; Pagan et al., 1999). In another non-limiting example, breast and gynecological cancer antigen specific antibodies are described in U.S. Pat. No. 5,939,277, incorporated herein by reference. In a further non-limiting example, prostate cancer specific antibodies are disclosed in U.S. Pat. No. 6,107,090, incorporated herein by reference. Thus, it is contemplated that the antibodies described herein or as would be known to one of ordinary skill in the art may be used to target specific tissues and cell types in combination with the compositions and methods of the present invention. In certain embodiments of the invention, contemplated targeting ligands interact with integrins, proteoglycans, glycoproteins, receptors or transporters. Suitable ligands include any that are specific for cells of the target organ, or for structures of the target organ exposed to the circulation as a result of local pathology, such as tumors.

In certain embodiments of the present invention, in order to enhance the transduction of cells, to increase transduction of target cells, or to limit transduction of undesired cells, antibody or cyclic peptide targeting moieties (ligands) are associated with the lipid complex. Such methods are known in the art. For example, liposomes have been described further that specifically target cells of the mammalian central nervous system (U.S. Pat. No. 5,786,214, incorporated herein by reference). The liposomes are composed essentially of N-glutarylphosphatidylethanolamine, cholesterol and oleic acid, wherein a monoclonal antibody specific for neuroglia is conjugated to the liposomes. It is contemplated that a monoclonal antibody or antibody fragment may be used to target delivery to specific cells, tissues, or organs in the animal, such as for example, brain, heart, lung, liver, etc.

Still further, a chimeric polypeptide may be delivered to a target cell via receptor-mediated delivery and/or targeting vehicles comprising a lipid or liposome. These take advantage of the selective uptake of macromolecules by receptor-mediated endocytosis that will be occurring in a target cell. In view of the cell type-specific distribution of various receptors, this delivery method adds another degree of specificity to the present invention.

Thus, in certain aspects of the present invention, a ligand will be chosen to correspond to a receptor specifically expressed on the target cell population. A cell-specific chimeric polypeptide delivery and/or targeting vehicle may comprise a specific binding ligand in combination with a liposome. The chimeric polypeptide to be delivered are housed within a liposome and the specific binding ligand is functionally incorporated into a liposome membrane. The liposome will thus specifically bind to the receptor(s) of a target cell and deliver the contents to a cell. Such systems have been shown to be functional using systems in which, for example, epidermal growth factor (EGF) is used in the receptor-mediated delivery of a nucleic acid to cells that exhibit upregulation of the EGF receptor.

In certain embodiments, a receptor-mediated delivery and/or targeting vehicles comprise a cell receptor-specific ligand and a peptide Others comprise a cell receptor-specific ligand to which peptide to be delivered has been operatively attached. For example, several ligands have been used for receptor-mediated gene transfer (Wu and Wu, 1987; Wagner et al., 1990; Perales et al., 1994; Myers, EPO 0273085), which establishes the operability of the technique. In another example, specific delivery in the context of another mammalian cell type has been described (Wu and Wu, 1993; incorporated herein by reference).

In still further embodiments, the specific binding ligand may comprise one or more lipids or glycoproteins that direct cell-specific binding. For example, lactosyl-ceramide, a galactose-terminal asialganglioside, have been incorporated into liposomes and observed an increase in the uptake of the insulin gene by hepatocytes (Nicolau et al., 1987). The asialoglycoprotein, asialofetuin, which contains terminal galactosyl residues, also has been demonstrated to target liposomes to the liver (Spanjer and Scherphof, 1983; Hara et al., 1996). The sugars mannosyl, fucosyl or N-acetyl glucosamine, when coupled to the backbone of a polypeptide, bind the high affinity manose receptor (U.S. Pat. No. 5,432,260, specifically incorporated herein by reference in its entirety). It is contemplated that the cell or tissue-specific transforming constructs of the present invention can be specifically delivered into a target cell or tissue in a similar manner.

In another example, lactosyl ceramide, and peptides that target the LDL receptor related proteins, such as apolipoprotein E3 ("Apo E") have been useful in targeting liposomes to the liver (Spanjer and Scherphof, 1983; WO 98/0748).

Folate and the folate receptor have also been described as useful for cellular targeting (U.S. Pat. No. 5,871,727). In this example, the vitamin folate is coupled to the complex. The folate receptor has high affinity for its ligand and is overexpressed on the surface of several malignant cell lines, including lung, breast and brain tumors. Anti-folate such as methotrexate may also be used as targeting ligands. Transferrin mediated delivery systems target a wide range of replicating cells that express the transferrin receptor (Gilliland et al., 1980).

c. Liposome/Nucleic Acid Combinations

In certain embodiments, a liposome/chimeric polypeptide may comprise a nucleic acid, such as, for example, an oligonucleotide, a polynucleotide or a nucleic acid construct (e.g., an expression vector). Where a bacterial promoter is employed in the DNA construct that is to be transfected into eukaryotic cells, it also will be desirable to include within the liposome an appropriate bacterial polymerase.

It is contemplated that when the liposome/chimeric polypeptide composition comprises a cell or tissue specific nucleic acid, this technique may have applicability in the present invention. In certain embodiments, lipid-based non-viral formulations provide an alternative to viral gene therapies. Although many cell culture studies have documented lipid-based non-viral gene transfer, systemic gene delivery via lipid-based formulations has been limited. A major limitation of non-viral lipid-based gene delivery is the toxicity of the cationic lipids that comprise the non-viral delivery vehicle. The in vivo toxicity of liposomes partially explains the discrepancy between in vitro and in vivo gene transfer results. Another factor contributing to this contradictory data is the difference in liposome stability in the presence and absence of serum proteins. The interaction between liposomes and serum proteins has a dramatic impact on the stability characteristics of liposomes (Yang and Huang, 1997). Cationic liposomes attract and bind negatively charged serum proteins. Liposomes coated by serum proteins are either dissolved or taken up by macrophages leading to their removal from circulation. Current in vivo liposomal delivery methods use aerosolization, subcutaneous, intradermal, intratumoral, or intracranial injection to avoid the toxicity and stability problems associated with cationic lipids in the circulation. The interaction of liposomes and plasma proteins is largely responsible for the disparity between the efficiency of in vitro (Felgner et al., 1987) and in vivo gene transfer (Zhu et al., 1993; Philip et al., 1993; Solodin et al., 1995; Liu et al., 1995; Thierry et al., 1995; Aksentijevich et al., 1996).

d. Lipid Administration

The actual dosage amount of a lipid composition (e.g., a liposome-chimeric polypeptide) administered to a patient can be determined by physical and physiological factors such as body weight, severity of condition, idiopathy of the patient and on the route of administration. With these considerations in mind, the dosage of a lipid composition for a particular subject and/or course of treatment can readily be determined.

The present invention can be administered intravenously, intradermally, intraarterially, intraperitoneally, intralesionally, intracranially, intraarticularly, intraprostaticaly, intrapleurally, intratracheally, intranasally, intravitreally, intravaginally, rectally, topically, intratumorally, intramuscularly, intraperitoneally, subcutaneously, intravesicularlly, mucosally, intrapericardially, orally, topically, locally and/or using aerosol, injection, infusion, continuous infusion, localized perfusion bathing target cells directly or via a catheter and/or lavage.

IX. Kits

Certain embodiments of the present invention concerns diagnostic or therapeutic kits. The peptides may be used in the form of a kit for determining the possibility of development or recurrence of a precancerous or cancerous growth in a patient with HPV. The kit may determine the stimulation of T-cell lymphocyte proliferation and/or an increase in T-helper 1 cytokine production. The components of the various kits may be stored in suitable container means. The container means will generally include at least one vial, test tube, flask, bottle, syringe or other container means, into which the peptide formulation is placed, preferably, suitably allocated. The kits may also comprise a second container means for containing a sterile, pharmaceutically acceptable buffer or other diluent. The kits of the present invention may also typically include a means for containing the vials in close confinement for commercial sale, such as, e.g., injection or blow-molded plastic containers into which the desired vials are retained.

The kit can contain reagents for detecting an interaction (detection reagent) between a sample and an antibody. The provided reagent can be radio-, fluorescently- or enzymatically-labeled. The kit can contain a known radiolabeled agent capable of binding or interacting with an antibody that allows a cell-mediated immune response to be detected and/or measured. In general, these methods will include first obtaining a sample suspected of containing such a protein, peptide or antibody, contacting the sample with an antibody or peptide in accordance with the present invention, as the case may be, under conditions effective to allow the formation of an immunocomplex, and then detecting the presence of the immunocomplex.

In some embodiments, one or more E6 and/or E7 peptides is includes in a suitable container. A sample can be contacted or incubated with the peptide(s) and then the sample can be assayed for a cell-mediated immune response against the peptide(s). Thus, in some embodiments, the kit contains a non-reacting structure. In some embodiments, the non-reacting structure may be plastic or some other synthetic material. The non-reacting structure can be a type of container to hold a sample, such as a container with a well. A container with multiple wells is also included as part of the invention. In some cases, the structure is lined with or has a membrane attached to it. It is contemplated that a well lined with a membrane can be incubated with an E6 or E7 peptide and then assayed using the same container for a cell-mediated immune response. This can be done by employing an antibody that can be used to detect a cell mediated immune response. Such antibodies include an antibody to a TH1 or TH2 cytokine, cytokine receptor, or any other receptor on a T cell that is indicative of a cell-mediated immune response. Detection reagents may also be included in the kit.

The reagent of the kit can be provided as a liquid solution, attached to a solid support or as a dried powder. Preferably, when the reagent is provided in a liquid solution, the liquid solution is an aqueous solution. Preferably, when the reagent provided is attached to a solid support, the solid support can be chromatograph media, a test plate having a plurality of wells, or a microscope slide. When the reagent provided is a dry powder, the powder can be reconstituted by the addition of a suitable solvent, that may be provided.

In general, the detection of immunocomplex formation is quite well known in the art and may be achieved through the application of numerous approaches. For example, the present invention contemplates the application of ELISA, RIA, immunoblot (e.g., dot blot), ELISPOT, indirect immunofluorescence techniques and the like. Generally, immunocomplex formation will be detected through the use of a label, such as a radiolabel or an enzyme tag (such as alkaline phosphatase, horseradish peroxidase, or the like). Of course, one may find additional advantages through the use of a secondary binding ligand such as a second antibody or a biotiniavidin ligand binding arrangement, as is known in the art.

For assaying purposes, it is proposed that virtually any sample suspected of comprising a cell capable of a cell-mediated immune response, as the case may be, may be employed. Samples may include cells, cell supernatants, cell suspensions, cell extracts, enzyme fractions, protein extracts, or other cell-free compositions suspected of containing a cell capable of a cell-mediated immune response. Generally speaking, kits in accordance with the present invention will include at least one E6 or E7 peptide and an antibody directed against a proteinaceous composition that is associated with a cell-mediated immune response, together with an immunodetection reagent and a means for containing the antibody, peptide, and reagent. The immunodetection reagent will typically comprise a label associated with the antibody or antigen, or associated with a secondary binding ligand. Exemplary ligands might include a secondary antibody directed against the first antibody or antigen or a biotin or avidin (or streptavidin) ligand having an associated label. Of course, as noted above, a number of exemplary labels are known in the art and all such labels may be employed in connection with the present invention.

The container will generally include a vial into which the antibody, antigen or detection reagent may be placed, and preferably suitably aliquotted. The kits of the present invention will also typically include a means for containing the antibody, antigen, and reagent containers in close confinement for commercial sale. Such containers may include injection or blow-molded plastic containers into which the desired vials are retained.

In one embodiment, a diagnostic kit comprises probes or primers for use with the nucleic acid detection methods. All the essential materials and reagents required for detecting peptide markers in a biological sample may be assembled together in a kit. This generally will comprise preselected primers for specific markers. Also included may be enzymes suitable for amplifying nucleic acids including various polymerases (RT, Taq, etc.), deoxynucleotides and buffers to provide the necessary reaction mixture for amplification.

Such kits generally will comprise, in suitable means, distinct containers for each individual reagent and enzyme as well as for each marker primer pair. Preferred pairs of primers for amplifying nucleic acids are selected to amplify the sequences specified in SEQ ID NO: 1-19 or a complement thereof.

In another embodiment, such kits will comprise hybridization probes specific for peptides corresponding to the sequences specified in SEQ ID NO: 1-19, or the complement thereof. Such kits generally will comprise, in suitable means, distinct containers for each individual reagent and enzyme as well as for each hybridization probe.

In other embodiments, the present invention concerns immunodetection kits for use with the immunodetection methods described above. As the peptides are generally proteins, polypeptides or peptides, the peptides will preferably be included in the kit. The immunodetection kits will thus comprise, in suitable container means, the peptide, and optionally, an immunodetection reagent.

The immunodetection reagents of the kit may take any one of a variety of forms, including those detectable labels that are associated with or linked to the given antibody. Detectable labels that are associated with or attached to a secondary binding ligand are also contemplated. Exemplary secondary ligands are those secondary antibodies that have binding affinity for the first antibody.

The kits may further comprise a suitably aliquoted composition of the wild-type or mutant protein, polypeptide or polypeptide, whether labeled or unlabeled, as may be used to prepare a standard curve for a detection assay. The kits may contain antibody-label conjugates either in fully conjugated form, in the form of intermediates, or as separate moieties to be conjugated by the user of the kit. The components of the kits may be packaged either in aqueous media or in lyophilized form.

Therapeutic kits of the present invention are kits comprising an peptide SEQ ID NO: 1-19. Such kits will generally contain, in suitable container means, a pharmaceutically acceptable formulation of a polypeptide, peptide, biological functional equivalent, immunological fragment, domain, inhibitor, antibody, gene, polynucleotide, nucleic acid, complement, or vector expressing any of the foregoing in a pharmaceutically acceptable formulation. The kit may have a single container means, or it may have distinct container means for each compound.

When the components of the kit are provided in one or more liquid solutions, the liquid solution is an aqueous solution, with a sterile aqueous solution being particularly preferred. The peptide compositions may also be formulated into a syringeable composition. In which case, the container means may itself be a syringe, pipette, or other such like apparatus, from which the formulation may be applied to an infected area of the body, injected into an animal, or even applied to and mixed with the other components of the kit.

However, the components of the kit may be provided as dried powder(s). When reagents or components are provided as a dry powder, the powder can be reconstituted by the addition of a suitable solvent. It is envisioned that the solvent may also be provided in another container means.

The container means of the kits will generally include at least one vial, test tube, flask, bottle, syringe or other container means, into which the antibody may be placed, and preferably, suitably aliquoted. Where, polypeptide or peptide, or a second or third binding ligand or additional component is provided, the kit will also generally contain a second, third or other additional container into which this ligand or component may be placed. The kits of the present invention will also typically include a means for containing the antibody, antigen, and any other reagent containers in close confinement for commercial sale. Such containers may include injection or blow-molded plastic containers into which the desired vials are retained.

Irrespective of the number or type of containers, the kits of the invention may also comprise, or be packaged with, an instrument for assisting with the injection/administration or placement of the ultimate peptide within the body of an animal. Such an instrument may be a syringe, pipette, forceps, or any such medically approved delivery vehicle.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Material and Methods

Patients

The present embodiment of the invention comprises a study population that was selected from patients seen at the colposcopy clinic of The University of Texas M. D. Anderson Cancer Center. Informed consent was obtained from the patients, and all procedures were performed according to an Institutional Review Board-approved protocol. The women were 17 years of age or older and not pregnant with no medical history of immune disorders. Four groups of women were identified for this study. Group 1 consisted of six women without cytological or histological diagnosis of CIN and with an HPV negative test ($CIN^{(-)}/HPV^{(-)}$). Group 2 included 31 women with a histological diagnosis of CIN and HPV positive test ($CIN^{(+)}/HPV^{(+)}$). Groups 3 and 4 were selected from women who had undergone ablative or excisional treatment for CIN at the colposcopy clinic at least 6 months before the study. The women in groups 3 and 4 were ($CIN^{(+)}/HPV^{(+)}$) before CIN treatment. However, at the time of enrollment, which was a minimum of 6 months after CIN treatment, the women were only assessed for disease status. Group 3 consisted of 22 women without evidence of recurrence of CIN ($Recur^{(-)}$), and group 4 included 10 with histological diagnosis of recurrent CIN ($Recur^{(+)}$). HPV positivity was determined using the Virapap/Viratype assay (Technologies Inc., Gaithersburg, Md.). In this protocol, the dot blot hybridization for HPV RNA is performed using exfoliated cervical epithelial cells obtained with cervical swabs. The assay method involves using a $^{32}P$-labeled DNA probe-set, which identifies HPV by type: 6/11, 16/18, and 31/33/35. Cells were isolated and processed according to the manufacturer's instructions. At the time of the study, this test was used as part of the standard care program at the colposcopy clinic. HPV positivity was further confirmed by PCR using DNA extracted from paraffin-embedded biopsy material as previously described (Ting et al., 1990; Schiffman et al., 1991). The consensus primers used for the PCR analysis were derived from the L1 open reading frame of the papillomaviruses (MY11, GCMCAGGGWCATAAYAATGG (SEQ ID NO: 23) and MY09, CGTCCMARRGGAWACTGATC (SEQ ID NO: 24); where M=A+C, R=A+G, W=A+T, Y=C+T). The HPV-16 positivity was confirmed using a specific oligonucleotide probe CATACACCTCCAGCACCTAA (SEQ ID NO: 25). The clinical characteristics, including HPV status, of the study subjects are listed in Table 2.

TABLE 2

Characteristics of the study subjects

| Characteristics | Total | Group 1 | Group 2 | Group 3 | Group 4 |
|---|---|---|---|---|---|
| No. of patients | 69 | 6 | 31 | 22 | 10 |
| Median age | 31 | 31 | 31 | 32 | 27 |
| Age range | 17-54 | 17-43 | 21-50 | 18-54 | 20-39 |
| Race | | | | | |
| White | 52 (75.4%) | 3 (50%) | 26 (83.9%) | 15 (68.2%) | 8 (80%) |
| Hispanic | 8 (12.6%) | 3 (50%) | 1 (3.2%) | 4 (18.2%) | 0 (0%) |
| African-American | 8 (12.6%) | 0 (0%) | 3 (9.7%) | 3 (13.6%) | 0 (0%) |
| Asian | 1 (1.4%) | 0 (0%) | 1 (3.2%) | 0 (0%) | 0 (0%) |
| HPV status | | | | | |
| Negative | 6 (8.7%) | 6 (100%) | 0 (0%) | 0 (0%) | 0 (0%) |
| Positive | 63 (91.3%) | 0 (0%) | 31 (100%) | 22 (100%) | 10 (100%) |
| HPV-16 | 57 (90.5%) | 0 (0%) | 31 (100%) | 17 (77.3%) | 9 (90%) |
| Other HPV Types | 6 (9.5%) | 0 (0%) | 0 (0%) | 5 (22.7%) | 1 (10%) |
| Initial Diagnosis* | | | | | |
| Negative | 6 (8.7%) | 6 (100%) | 0 (0%) | 0 (0%) | 0 (0%) |
| CIN1 | 4 (5.8%) | 0 (0%) | 0 (0%) | 4 (18.2%) | 0 (0%) |
| CIN 2 & 3 | 59 (85.5%) | 0 (0%) | 31 (100%) | 18 (81.8%) | 10 (100%) |

*Note:
For group 3 the diagnosis at the time of recruitment into study was negative for CIN, while that for group 4 was positive for CIN 2/3.

Peptides

Peptide sequences corresponding to the E6 and E7 oncoproteins of HPV-16 were selected on the basis of the amphipathic structures and information related to known T-cell epitopes described in the literature. Table 3 lists the peptides used in the present study. All peptides were made as reported earlier (Sarkar et al., 1995) using the Merrifield solid-phase method (Merrifield, 1963) either on a modified Vega 250 automatic peptide synthesizer (Vega Biochemicals, Tucson, Ariz.) or by the "bag" method as described by Houghten, 1985. In most of the experiments, the purity of the peptides used was approximately 70-80% and in some of the experiments, peptides exhibiting a purity >95% were used with identical results. In addition to the E6 and E7 peptides, we used a peptide from the c-mos protooncogene [aa 158-170, STRTPEDSNSLGT (SEQ ID NO 22)] as a negative control. Stock solutions of peptides were prepared in PBS (pH 7.0) and filter sterilized.

T-Cell Proliferation Assay

Heparinized blood was collected from the study participants by venipuncture. PBMCs were isolated by centrifugation on a Ficoll-Hypaque density gradient (Histopaque-1073; Sigma Chemical Co., St. Louis, Mo.). The proliferative responses of PBMC from different individuals after stimulation with PHA, c-mos peptide, or individual E6 and E7 peptides (Table 4) were determined using the [$^3$H]thymidine incorporation assay as previously described Nehete et al., 1996). Briefly, each sample was seeded in triplicate in 96-well microtiter plates and incubated for 7 days at 37° C. in a humidified 5% $CO_2$ atmosphere. During the final 16-18 h, 1 µCi of $^3$[H]thymidine (6.7 Ci/mmol; ICN Biomedicals, Inc., Costa Mesa, Calif.) was added. The cells were harvested onto filter strips to estimate $^3$[H]thymidine incorporation. The specific radioactivity of cells treated with various additions was calculated in each case by subtracting the counts per minute (cpm) values obtained with cells cultured in medium alone. Data from pilot experiments showed that at 5 µg/ml, each peptide yields consistent levels of proliferation. The significance of T-cell proliferative responses to the individual E6 and E7 peptides (in terms of stimulation index [SI]) was calculated as the fold increase of [$^3$H]thymidine incorporation by cells exposed to the peptide over that by the control to which no peptide was added. An SI value ≧3.0, which was considered a positive response, was used for all statistical analyses to determine the significance of proliferative responses and the association with disease-free or disease-recurrence status. In all the experiments, data from triplicate samples were comparable with a standard error of <10%. None of the women in the four study groups tested showed proliferative responses specific to the control c-mos peptide (SI<2.0).

TABLE 3

Amino acid sequences of the E6 and E7 peptides from HPV-16

| Peptide | Residues | Sequence |
|---|---|---|
| E6 peptides | | |
| K9L (SEQ ID NO: 1) | (aa 18-26) | KLPQLCTEL |
| E10I (SEQ ID NO: 2) | (aa 25-34) | ELQTTIHDII |
| C10R (SEQ ID NO: 3) | (aa 37-46) | CVYCKQQLLR |
| Q15L (SEQ ID NO: 4) | (aa 43-57) | QLLRREVYDFAFRDL |
| V10C (SEQ ID NO: 5) | (aa 49-58) | VYDFAFRDLC |
| P9L (SEQ ID NO: 6) | (aa 66-74) | PYAVCDKCL |
| P10I (SEQ ID NO: 7) | (aa 102-111) | PLCDLLIRCI |

TABLE 3-continued

Amino acid sequences of the E6 and E7 peptides from HPV-16

| Peptide | Residues | Sequence |
|---|---|---|
| Q20P (SEQ ID NO: 8) | (aa 97-116) | QQYNKPLCDLLIRCINCQKP |
| R16R (SEQ ID NO: 9) | (aa 131-146) | RWTGRCMSCCRSSRTR |
| G10S (SEQ ID NO: 10) | (aa 141-150) | GRCMSCCRSS |
| E7 peptides | | |
| T10Q (SEQ ID NO: 11) | (aa 7-15) | TLHEYMLELQ |
| M9T (SEQ ID NO: 12) | (aa 12-20) | MLDLQPETT |
| D9L (SEQ ID NO: 13) | (aa 14-22) | DLQPETTDL |
| Q19D (SEQ ID NO: 14) | (aa 44-62) | QAEPDRAHYNIVTFCCKCD |
| R9F (SEQ ID NO: 15) | (aa 49-57) | RAHYNIVTF |
| R9V (SEQ ID NO: 16) | (aa 66-74) | RLCVQSTHV |
| L9V (SEQ ID NO: 17) | (aa 82-90) | LLMGTLGIV |
| G10C (SEQ ID NO: 18) | (aa 85-94) | GTLGIVCPIC |
| D20C (SEQ ID NO: 19) | (aa 75-94) | DIRTLEDLLMGTLGIVCPIC | aa, amino acid

Cytokine Analysis

Cryopreserved PBMC were used for these assays. The PBMC ($1 \times 10^5$) were incubated with various HPV peptides in RPMI-1640 medium (containing 10% fetal calf serum) in triplicate wells of 96-well round-bottom plates for 48 h at 37° C. Supernatants (100 µl) were removed from each well after centrifugation and stored frozen at −70° C. in another 96-well plate. The plates were then thawed and the supernatants assayed for various cytokines (IFN-γ, IL-2, IL-4, IL-10, and IL-12) using the Cytoscreen immunoassay kits (Biosource International, Camarillo, Calif.) according to the manufacturer's instructions.

Statistical Analysis

Differences in the SI values between the patient groups were assessed by Pearson $X^2$ and Fisher's exact tests. For the purpose of the statistical analysis, significant proliferative response was defined as SI≧3.0. Statistical significance was set at p<0.05.

Example 2

A total of 69 women ranging in age from 17 to 54 years (median 31 years) were enrolled in the study. Of these 69 women, 52 were white, 8 each were African American and Hispanic, and one was Asian (Table 2). PBMC from these women were analyzed for proliferative response to the synthetic peptides corresponding with antigenic sequences of the E6 and E7 oncoproteins of HPV-16 (Table 3) (FIG. 1A).

Analyses of proliferative responses specific to various E6 and E7 peptides in each of the four different groups of patients revealed that the majority of patients in group 3 (Recur$^{(-)}$) exhibited positive responses (SI≧3.0) to all the seven E6 peptides and 7/8 E7 peptides tested (FIG. 1A). On the other hand, only 5/31 untreated patients in the group 2 (CIN$^{(+)}$/HPV$^{(+)}$) and none in the groups 1 (CIN$^{(-)}$/HPV$^{(-)}$) and 4 (Recur$^{(+)}$) showed responses to any of the peptides tested. This is summarized in FIG. 1B.

The relationship between proliferative response to E6 and/or E7 peptides and post-treatment disease status in women in groups 3 and 4 are presented in Table 4. Whereas none of the patients in group 4 (Recur$^{(-)}$) showed response to any E6 or E7 peptide tested, in group 3 64% of patients had significant proliferative responses to the E6 peptides (p=0.001), 82% to the E7 peptides (p<0.001), and 86% to at least one of the E6 or E7 peptides (p<0.001). There was no difference in proliferative response to a common mitogen like PHA (p=0.912, data not shown) between groups 3 and 4, suggesting that there is no impairment in the innate immune status of these patients. These results strongly suggest a relationship of proliferative responses to synthetic peptides from the E6 and E7 oncoproteins of HPV-16 and disease-free condition after CIN treatment.

Figure 2:
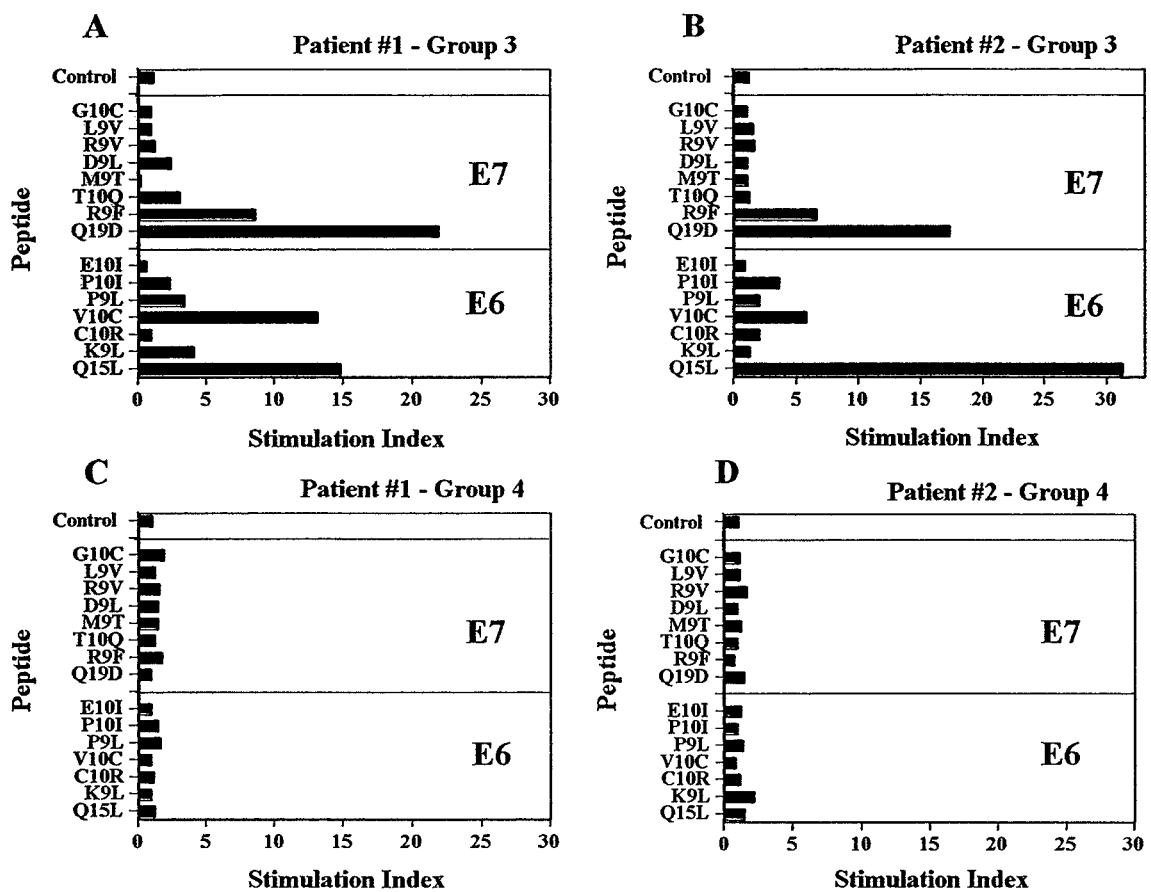
FIG. 2A-D. Proliferative responses of PBMC from patients in groups 3 ($Recur^{(-)}$) and 4 ($Recur^{(+)}$) to synthetic peptides from the E6 and E7 oncoproteins of HPV-16. PBMC from women in these groups were tested for proliferative responses to a control peptide (control), and 7 and 8 peptides each from the E6 and E7 oncoproteins, respectively, of HPV-16. Representative data showing SI values from two patients each from group 3 (panels A and B) and group 4 (panels C and D) are shown.

The inventors identified higher levels of proliferative responses to two peptides each from the E6 (Q15L and V10C) and E7 (Q19D and R9F). Representative proliferative responses, in terms of SI values, from 2 patients in groups 3 and 4 to 7 synthetic peptides from the E6 oncoprotein and 8 from E7 oncoprotein of HPV-16 are shown in FIG. 2. Comparison of proliferative responses to theses four peptides showed statistically significant differences between women in groups 3 and 4 (Table 5). Whereas no proliferative responses to these peptides were observed in group 4, in group 3 a total of 11 women exhibited responses to peptide Q15L (p=0.006), 10 to peptide V10C (p=0.006), 13 to peptide Q19D (p=0.002), and 10 to peptide R9F (p=0.013). As seen in Table 3, nine of the 10 amino acids in the E6 peptide V10C overlap with those of Q15L peptide. Similarly, the 9 amino acids of the E7 peptide R9F overlap with amino acids of the Q19D peptide. Proliferative responses specific to these four peptides together could account for all the responses (19/22 women) observed in group 3 (Recur$^{(-)}$). These results suggest that, with respect to HPV-specific cellular immune responses, the amino acid sequences for the Q15L and Q19D peptides within the HPV-16 oncoproteins E6 and E7, respectively, may be immunodominant regions.

Figure 3:
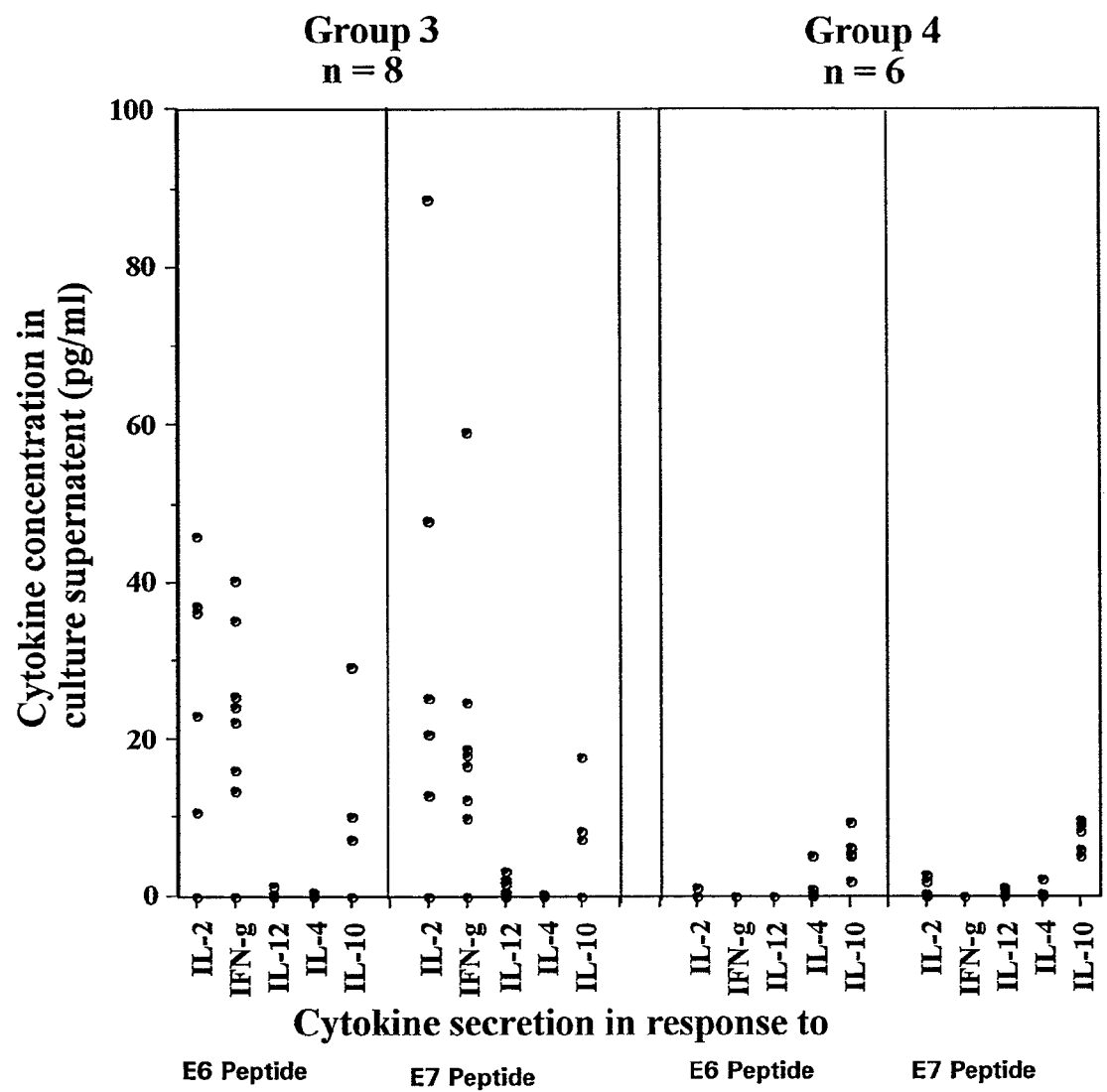
FIG. 3. Production of TH1 cytokines by PBMC from women in group 3 in response to stimulation with selected E6 and E7 peptides. PBMC from women in groups 3 ($Recur^{(-)}$) and 4 ($Recur^{(+)}$) were cultured in the presence of the E6 peptide Q15L and E7 peptide Q19D for two days and the supernatant fluid in each case was analyzed for the presence of various TH1 (IL-2, IFN-γ, IL-12) and TH2 (IL-4, IL-10) cytokines by ELISA. The amount of each cytokine produced, after adjusting to medium controls was shown for each of the patient tested from groups 3 and 4.

The inventors also tested, on a subsample of the study population, whether these peptides will also induce production of various TH1 and TH2 cytokines. Cryopreserved PBMC from 8 women in group 3 (Recur(−)), and 6 from group 4 (Recur(+)) were stimulated in vitro with peptides Q15L and Q19D. The amounts of various TH1 cytokines (IL-2, IL-12, and IFN-□), and TH2 cytokines (IL-4 and IL-10) in the culture supernatants, after adjusting to unstimulated cultures were shown in FIG. 3. PBMC from 7 of 8 (87.5%), and 5 of 8 (62.5%) women in group 3 (Recur(−)) showed production of IFN-□, and IL-2, respectively, in response to both Q15L and Q19D (Table 6). Additionally, IL-12 production was observed in response to Q15L in PBMC from 3 of 8 women in this group, whereas Q19D-mediated production of IL-12 was evident in 6 of 8 women. On the other hand, none of the PBMC from women in this group secreted IL-4 in response to stimulation with peptides Q15L or Q19D, and only 3 women showed IL-10 production in response to either of the peptides. In contrast to women in group 3 (Recur$^{(-)}$), women in group 4 (Recur$^{(+)}$) predominantly showed IL-10 production (5 of 6 with Q15L, and 6 of 6 with the Q19D). In 1 of the 6 women in this group, IL-4 production was observed when the PBMC were stimulated with either of the two peptides tested (Table 6). Overall, these results showed that patients in group 3 (Recur$^{(-)}$) predominantly exhibited TH1 cytokine production (IL-2, IFN-γ, and IL-12), whereas women in group 4 (Recur$^{(+)}$), despite not exhibiting specific proliferative responses directed against the HPV peptides, showed production of IL-10, a TH2 cytokine.

TABLE 4

Association between proliferative response to all synthetic peptides of HPV-16 oncoproteins E6 and/or E7 and disease status following CIN treatment

| Proliferative Response | Group 3 (Disease-free) | Group 4 (recurrence) | Significance |
|---|---|---|---|
| | E6 peptides | | |
| Yes[a] | 14 (64%) | 0 | |
| No[b] | 8 (36%) | 10 (100%) | p = 0.001 |
| | E7 peptides | | |
| Yes[a] | 18 (82%) | 0 | |
| No[b] | 4 (18%) | 10 (100%) | p < 0.001 |
| | Any E6 or E7 peptide | | |
| Yes[a] | 19 (86%) | 0 | |
| No[b] | 3 (14%) | 10 (100%) | p < 0.001 |

[a]SI ≧ 3.0
[b]SI < 3.0

TABLE 5

Association between proliferative response to specific synthetic peptides of HPV-16 oncoproteins E6 and/or E7 and disease status following CIN treatment

| Proliferative Response | | Group 3 (disease-free) (n = 22) | Group 4 (recurrence) (n = 10) | Significance |
|---|---|---|---|---|
| | | E6 peptides | | |
| Q15L | Yes[a] | 11 (50%) | 0 | |
| | No[b] | 11 (50%) | 10 (100%) | P = 0.006 |
| V10C | Yes[a] | 11 (50%) | 0 | |
| | No[b] | 11 (50%) | 10 (100%) | P = 0.006 |
| | | E7 peptides | | |
| Q19D | Yes[a] | 13 (59%) | 0 | |
| | No[b] | 9 (41%) | 10 (100%) | P = 0.002 |
| R9F | Yes[a] | 10 (46%) | 0 | |
| | No[b] | 12 (54%) | 10 (100% | P = 0.013 |

[a]SI ≧ 3.0
[b]SI < 3.0

TABLE 6

Cytokine production of PBMC from patients in groups 3 and 4 in response to stimulation with synthetic peptides from the E6 and E7 oncoproteins of HPV-16[a]

| Cytokine[b] | Group 3 (n = 8) | | Group 4 (n = 6) | |
|---|---|---|---|---|
| | Q15L[c] | Q19D[d] | Q15L | Q19D |
| IFN-γ | 7/8 | 7/8 | 0/6 | 0/6 |
| EL-2 | 5/8 | 5/8 | 0/6 | 0/6 |
| EL-12 | 3/8 | 6/8 | 0/6 | 1/6 |
| IL-4 | 0/8 | 0/8 | 1/6 | 1/6 |
| IL-10 | 3/8 | 3/8 | 5/6 | 6/6 |

[a]Number of patients positive/number tested.
[b]Positivity for cytokine production is based on values above the sensitivity of the test kit used for each cytokine in terms of pg/ml: IL-2 = 8.7, IFN-γ = 4.0, IL-12 = 1.0, IL-4 = 2.0, and IL-10 = 5.0.
[c]Q15L Peptide from the E6 oncoprotein of HPV-16.
[d]Q19D Peptide from the E7 oncoprotein of HPV-16.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,162,282
U.S. Pat. No. 4,275,149
U.S. Pat. No. 4,277,437
U.S. Pat. No. 4,310,505
U.S. Pat. No. 4,533,254
U.S. Pat. No. 4,683,195
U.S. Pat. No. 4,683,202
U.S. Pat. No. 4,728,575
U.S. Pat. No. 4,728,578
U.S. Pat. No. 4,737,323
U.S. Pat. No. 4,797,368
U.S. Pat. No. 4,800,159
U.S. Pat. No. 4,883,750
U.S. Pat. No. 4,921,706
U.S. Pat. No. 5,028,592
U.S. Pat. No. 5,139,941
U.S. Pat. No. 5,279,721
U.S. Pat. No. 5,432,260
U.S. Pat. No. 5,786,214
U.S. Pat. No. 5,840,317
U.S. Pat. No. 5,840,873
U.S. Pat. No. 5,843,640
U.S. Pat. No. 5,843,651
U.S. Pat. No. 5,843,663

U.S. Pat. No. 5,846,708
U.S. Pat. No. 5,846,717
U.S. Pat. No. 5,846,726
U.S. Pat. No. 5,846,729
U.S. Pat. No. 5,849,481
U.S. Pat. No. 5,849,486
U.S. Pat. No. 5,849,487
U.S. Pat. No. 5,851,772
U.S. Pat. No. 5,853,990
U.S. Pat. No. 5,853,992
U.S. Pat. No. 5,853,993
U.S. Pat. No. 5,856,092
U.S. Pat. No. 5,861,244
U.S. Pat. No. 5,863,732
U.S. Pat. No. 5,863,753
U.S. Pat. No. 5,866,331
U.S. Pat. No. 5,871,727
U.S. Pat. No. 5,879,703
U.S. Pat. No. 5,882,654
U.S. Pat. No. 5,900,481
U.S. Pat. No. 5,905,024
U.S. Pat. No. 5,910,407
U.S. Pat. No. 5,912,124
U.S. Pat. No. 5,912,145
U.S. Pat. No. 5,919,626
U.S. Pat. No. 5,919,630
U.S. Pat. No. 5,925,517
U.S. Pat. No. 5,928,862
U.S. Pat. No. 5,928,869
U.S. Pat. No. 5,929,227
U.S. Pat. No. 5,932,413
U.S. Pat. No. 5,935,791
U.S. Pat. No. 5,939,277
U.S. Pat. No. 6,107,090
U.S. Pat. No. 6,135,965
U.S. Pat. No. 6,214,874
U.S. Pat. No. 6,238,659
U.S. Pat. No. 6,245,568
U.S. Pat. No. 6,258,576
EPA No. 320,308
EPA No. 329,822
EPO 0273085
GB Application No. 2202328
GB Application No. 2193095 A
PCT Application No. PCT/US85/01161
PCT Application No. PCT/US87/00880
PCT Application No. PCT/US89/01025
PCT Application No. PCT/US89/05040;
PCT Application WO 88/10315
PCT Application WO 89/06700
WO 90/07641
WO 98/0748
WO 99/18933
Abbondanzo, et al., Am J Clin Pathol., 93(5):698-702, 1990.
Abe, et al., *Neurosci Res.*, 38(4):325-9, 2000.
Aichele, et al., *J Exp Med*, 171(5):1815-20, 1990.
Aksentijevich et al., *Hum Gene Ther.*, 7(9):1111-22, 1996.
Allred, et al., *Arch Surg.* 1990 January; 125(1): 107-13. Review.
Altman et al., *Science*, 274:94-96, 1996.
Baichwal et al., "Vectors for gene transfer derived from animal DNA viruses: Transient and stable expression of transferred genes," *In: Gene Transfer*, Kucherlapati, R., ed.,
Bajorin, et al., *J Clin Oncol.*, 6(5):786-92, 1988.
Bangham, et al., *J. Mol. Biol.*, 13:238-252, 1965.
Barany, et al., "Solid-Phase Peptide Synthesis," *In: The Peptides: Analysis, Synthesis, Biology*, Gross and Meinhofer, eds., Academic Press, New York, pp. 3-284, 1980.
Bevan, et al., *Nature*, 342(6249):478-9, 1989.
Birner, et al., *Mod. Pathol.*, 14(7):702-9, 2001.
Boussif et al., *Proc. Nat'l Acad. Sci. USA*, 92:7297-7301, 1995.
Brinton, et al., In: N. Munoz, F. X. Bosch, K. V. Shah, and A. Meheus (eds.), The Epidemiology of Cervical Cancer and Human Papillomavirus (IARC Scientific Publications, 119), pp. 3-23. Lyon: Oxford University Press, 1992.
Brown, et al., *Am J Vet Res.*, 51(9):1476-80, 1990.
Canfield et al., *Methods in Enzymology*, 189, 418-422, 1990.
Capaldi, et al., *Biochem. Biophys. Res. Comm.*, 74(2):425-433, 1977.
Casement, et al., *Virology*, 211(1):261-7, 1995
Cason, et al., *Int. J. Cancer*, 50: 349-355, 1992.
Chang et al., *Hepatology*, 14:134 A, 1991.
Chen, et al., *Mol. Cell. Biol.*, 7:2745-2752, 1987.
Cheng, et al., *Investigative Radiology*, vol. 22, pp. 47-55 (1987).
Clark et al., *Human Gene Therapy*, 6:1329-1341.1995
Clave, et al., *Diagn. Mol. Pathol.*, 9(3) 145-150, 2000.
Clerici, et al., *J. Natl. Cancer Inst.*, 89: 245-250, 1997.
Coffin, *In: Virology*, Fields et al., eds., Raven Press, New York, pp. 1437-1500, 1990.
Coupar et al., *Gene*, 68:1-10, 1988.
Crowe, et al., *AIDS Res Hum Retroviruses*, 3(2):135-45, 1987.
da Costa, et al., *Biocell*, 23(1): 65-72, 1999.
De Gruijil, et al., *J. Gen. Virol.* 77, 2183-2191, 1996.
De Jager, et al., *Semin Nucl Med.* 1993 April; 23(2):165-79. Review.
Deamer, et al., in Liposomes (M. Ostro, ed.), Marcel Dekker, Inc., New York (1983), pp. 27-52.
Deres, et al., *Nature.* 1989 Nov. 30; 342(6249):561-4.
Doolittle, et al., *Methods Mol. Biol.* 1999; 109:215-37. Review
el Gorab, et al., *Biochim Biophys Acta.*, 306(1):58-66, 1973.
Fechheimer et al., *Proc. Nat'l Acad. Sci. USA*, 84:8463-8467, 1987.
Felgner et al., *Proc Natl Acad Sci USA.*, 84(21):7413-7, 1987.
Feltkamp, et al., *Eur. J. Immunol.*, 23: 2242-2249, 1993.
Fendler et al., Catalysis in Micellar and Macromolecular Systems, Academic Press, New York, 1975.
Flotte et al., *Gene Therapy*, 2:29-37, 1995.
Flotte, et al., *Am. J. Respir. Cell Mol. Biol.*, 7:349-356, 1992.
Fraley et al., *Proc. Nat'l Acad. Sci. USA*, 76:3348-3352, 1979.
Fraley, et al., *Trends Biochem. Sci.*, 6:77, 1981
Friedmann, *Science*, 244:1275-1281, 1989.
Frohman, *PCR Protocols: A Guide To Methods and Applications*, Academic Press, New York, 1990.
Fujishima, et al., *Cytometry.*, 24(4):382-9, 1996.
Gabizon et al., *Cancer Res.*, 50(19):6371-8, 1990.
Ghosh, et al., In: Wu G. Wu C ed., Liver diseases, targeted diagnosis and therapy using specific receptors and ligands, New York: Marel Dekker, pp. 87-104, 1991.
Gilliland et al., *Cancer Res.*, 40(10):3564-9, 1980.
Gloeckner, et al., *J. Immunol. Methods*, 252(1-2):131-8, 2001.
Gopal, *Mol. Cell Biol.*, 5:1188-1190, 1985.
Graham et al., *J. Gen. Virol.*, 36:59-72, 1977.
Graham, et al., *Virology*, 52:456-467, 1973.
Gregoriadis, et al., *Biochem Biophys Res Commun.*, 89(4): 1287-1293, 1979.
Gregoriadis, G., ed., *Liposome Technology, vol. I, pp.* 30-35, 51-65 and 79-107, CRC Press Inc., Boca Raton, Fla., 1984.

Grunhaus, et al., *Seminar in Virology,* 3:237-252, 1992.
Gulbis, et al., *Hum Pathol.* 1993 December; 24(12):1271-85. Review.
Hamsikova, et al., *J. Infect. Dis.,* 170: 1424-1431, 1994
Hara et al., *Biochim Biophys Acta.,* 1278(1):51-8, 1996
Harland, et al., *J. Cell Biol.,* 101: 1094-1099, 1985.
Heath, et al., *Chem. Phys. Lipids,* 40:347, 1986.
Hermonat, et al., *Proc. Nat'l Acad. Sci. USA,* 81:6466-6470, 1984.
Hope et al., *Biochimica et Biophysica Acta,* 812: 55-65, 1985.
Horwich et al *J. Virol.,* 64:642-650, 1990.
Irie, et al., *Lancet,* 1(8641):786-7, 1989.
Irie, et al., *Proc Natl Acad Sci USA,* 83(22):8694-8, 1986.
Jha, et al., *Lancet,* 341: 1116-1118, 1993.
Kadish, et al., *J. Natl. Cancer. Inst.* 89:1285-1293, 1997.
Kaplitt et al., *Nature Genetics,* 8:148-154, 1994
Kast, et al., *Immunol Lett.,* 30(2):229-32, 1991.
Kast, et al., *J. Immunotherapy,* 14: 115-120, 1993.
Kotin et al., *Proc. Nat'l Acad. Sci. USA,* 87:2211-2215, 1990.
Koutsky, et al., *N Engl J Med.* 327(18):1272-8, 1992
Kurman, et al., *JAMA,* 271:1866-1869, 1994.
Kurman, et al., The Bethesda system for reporting cervical/vaginal cytologic diagnoses. Definitions, criteria and explanatory notes for terminology and specimen adequacy. New York: Springer-Verlag. pp, 30-43, 1994.
Kwack, et al., *Mol Cells,* 10(5):575-8, 2000.
LaFace et al, *Viology,* 162:483-486, 1988.
Laughlin et al., *J. Virol.,* 60:515-524, 1986.
Lebkowski, et al., *Mol. Cell. Biol.,* 8:3988-3996, 1988.
Liu et al., *Biochim Biophys Acta,* 1240(2):277-84, 1995.
Lorenzato et al., *J. Pathol.,* 194(2):171-6, 2001.
Lorincz, et al., *Obstet. Gynecol.,* 79: 328-337, 1992.
Lukacher, et al., *J Exp Med.,* 160(3):814-26, 1984.
Luo et al., *Blood,* 82:suppl. 1:303 A, 1994.
Manning, et al., *Biotechniques,* 6:682, 1988.
Martin et al., *Nature,* 345(6277):739-743, 1990.
Mayer et al., *Biochimica et Biophysica Acta,* vol. 858, pp. 161-168, 1986.
Mayhew et al., *Biochimica et Biophysica Acta,* vol. 775, pp. 169-174, 1984.
Mayhew et al., *Methods in Enzymology,* vol. 149, pp. 64-77, 1987.
McCarty et al., *J. Virol.,* 65:2936-2945, 1991.
McLaughlin et al., *J. Virol.,* 62:1963-1973, 1988.
Mitchell, et al., *Ann N Y Acad Sci.,* 690:153-66, 1993.
Mitchell, et al., *J Clin Oncol.,* 8(5):856-69, 1990.
Morrison, et al., *Int J Cancer.* 49(1):6-13, 1991
Morton, et al., *Ann Surg.,* 216(4):463-82, 1992.
Morton, et al., *CA Cancer J Clin.,* 46(4):225-44, 1996.
Munger, et al., *J. Virol.,* 63: 4417-4421, 1989.
Munoz, et al., *Int. J. Cancer,* 52: 743-749, 1992.
Muzyczka, N., *Curr. Top. Microbiol. Immunol.,* 158:97-129, 1992.
Nakagawa, et al., Clin. Diag. Lab. Immunol., 3: 205-210, 1996.
Nakagawa, et al., *J. Infect. Dis.,* 175: 927-931, 1997.
Nehete et al., *J. Clin. Immunol.,* 16:115-124, 1996.
Nehete, et al., *Cell Immunol.,* 160(2):217-23, 1995.
Nicolas, et al., *In: Vectors: A survey of molecular cloning vectors and their uses,* Rodriguez and Denhardt, eds., Butterworth, Stoneham, England, pp. 494-513, 1988.
Nicolau et al., *Biochim. Biophys. Acta,* 721:185-190, 1982.
Ohi et al., *Gene,* 89:279-282, 1990.
Park, et al., *Asia-Oceania J. Obstet. Gynaecol.,* 18: 171-175, 1992.
Parkin, et al., *Int. J. Cancer,* 84:827-841, 1999.
Paskind et al., *Virology,* 67:242-248, 1975.
Plenum Press, New York, pp. 117-148, 1986.
Poijak, et al., *J. Clin. Microbiol.* 37:796-797, 1999.
Potter et al., *Proc. Nat'l Acad. Sci. USA,* 81:7161-7165, 1984.
Ravindranath, et al., *Int Rev Immunol,* 7(4):303-29, 1991.
Ridgeway, *In: Vectors: A survey of molecular cloning vectors and their uses,* Rodriguez R. L., Denhardt D. T., eds., Butterworth, Stoneham, England, pp. 467-492, 1988.
Rippe et al., *Mol. Cell Biol.,* 10:689-695, 1990.
Rosenberg, et al., *N Engl J Med.,* 319(25):1676-80, 1988.
Rossen, et al., *J Immunol.,* 135(5):3289-97, 1985.
Roux et al., *Proc. Nat'l Acad. Sci. USA,* 86:9079-9083, 1989.
Sambrook, et al., *Molecular Cloning, A Laboratory Manual,* 2nd ed., Cold Spring Harbor Laboratory, Cold Spring, Harbor, N.Y., 1989.
Samulski et al., *EMBO J.,* 10:3941-3950, 1991.
Samulski et al., *J. Virol.,* 63:3822-3828, 1989.
Sarkar, et al., *Viral Immunol.,* 8: 165-174, 1995.
Sastry, et al., *Vaccine.,* 12(14):1281-7, 1994.
Sastry, et al., *Virology,* 188: 502-509, 1992.
Seedorf, et al., *EMBO J.,* 6: 139-144, 1987.
Shelling, et al., *Gene Therapy,* 1:165-169, 1994.
Shepherd, et al., *J. Gen. Virol.,* 73: 1269-1274, 1992.
Shinoda et al., Colloidal Surfactant, Academic Press, especially "The Formation of Micelles", Ch. 1, 1-96, 1963.
Solodin et al., *Biochemistry,* 34(41):13537-44, 1995.
Spanjer et al., *Biochim Biophys Acta,* 734(1):40-7, 1983.
Stauss, et al., *Proc. Natl. Acad. Sci. USA,* 89: 7871-7875, 1992.
Strang, et al., *J. Gen. Virol.,* 71: 423-431, 1990.
Stratford-Penicaudet, et al., *In: Human Gene Transfer,* O. Cohen-Haguenauer and M. Boiron, eds., John Libbey Eurotext, France, p. 51-61, 1991.
Szoka, et al., *Proc. Natl. Acad. Sci.,* 75:4194-4198, 1978.
Tam, et al., *J. Am. Chem. Soc.,* 105:6442, 1983.
Templeton et al., *Nat. Biotechnol.,* 15(7):647-52, 1997.
Thierry et al., *Proc Natl Acad Sci USA.,* 92(21):9742-6, 1995.
Tindle, et al., *Proc. Natl. Acad. Sci. USA,* 88: 5887-5891, 1991.
Tobery, et al., *J. Immunol. Methods,* 254(1-2)59-66, 2001.
Tooze, J., ed., *Molecular Biology of DNA Tumor Viruses,* 2nd ed., Cold Spring Harbor Laboratory, Cold Spring Harbor, N.Y., 1991.
Townsend, et al., *Cell,* 44:949-968, 1986.
Tratschin et al., *Mol. Cell. Biol.,* 4:2072-2081, 1984.
Tratschin et al., *Mol. Cell. Biol.,* 5:32581-3260, 1985.
Tsukui, et al., *Cancer Res.,* 56: 3967-3974, 1996.
Tur-Kaspa et al., *Mol. Cell. Biol.,* 6:716-718, 1986.
Unanue, et al., *FASEB J.,* 13:2496-502, 1989.
Von Knebel Doeberitz, et al., *Cancer Res.,* 48: 3780-3786, 1988.
Wagner et al., *Mol. Cell.* 40: 281-286, 1999.
Wallace, et al., *Nucl. Acid Res.,* 9:879, 1981
Walsh et al., *Proc. Nat'l Acad. Sci. USA,* 89:7257-7261, 1994.
Wei et al., *Gene Therapy,* 1:261-268, 1994.
Wettstein, et al., In: H. Pfister (ed.), Papillomaviruses and Human Cancer, pp. 145. Florida: CRC Press, 1990.
Wu, et al., *Biochemistry,* 27:887-892, 1988.
Wu, et al., *J. Biol. Chem.,* 262:4429-4432, 1987.
Yang et al., *J. Virol.,* 68:4847-4856, 1994.
Yoder et al., *Blood,* 82:suppl. 1:347 A, 1994.
Zhou et al., *Exp. Hematol.* (NY), 21:928-933, 1993.
Zhou et al., *J. Exp. Med,* 179:1867-1875, 1994.
Zhu et al., *Chin J Biotechnol,* 9(4):257-61, 1993.
Zur Hausen, et al., *Curr. Topics Microbiol. Immunol.,* 186: 131-156, 1994.

The invention claimed is:

1. A method for reducing the risk of recurrence of a pre-cancerous or cancerous growth in a patient infected with HPV who has been treated for the growth comprising
administering to a patient at risk for recurrence of HPV-associated pre-cancerous or cancerous growth an effective amount of at least one E6 or E7 HPV peptide, wherein a cell-mediated immune response to at least one E6 or E7 peptide is induced in the patient and the cell-mediated immune response to such at least one peptide is indicative of a reduced risk of recurrence.

2. The method of claim 1, wherein the patient is administered an effective amount of an E6 HPV peptide.

3. The method of claim 2, wherein the E6 peptide is K9L (SEQ ID NO:1), E10I (SEQ ID NO:2), C10R (SEQ ID NO:3), Q15L (SEQ ID NO:4), V10C (SEQ ID NO:5), P9L (SEQ ID NO:6), P10I (SEQ ID NO:7), Q20P (SEQ ID NO:8), R16R (SEQ ID NO:9), or G10S (SEQ ID NO:10).

4. The method of claim 2, wherein the patient is administered a combination of E6 HPV peptides selected from the group consisting of K9L (SEQ ID NO: 1), E10I (SEQ ID NO:2), C10R (SEQ ID NO:3), Q15L (SEQ ID NO:4), and V10C (SEQ ID NO:5).

5. The method of claim 1, wherein the patient is administered an effective amount of an E7 HPV peptide.

6. The method of claim 5, wherein the E7 HPV peptide is T10Q (SEQ ID NO:11), M9T (SEQ ID NO:12), D9L (SEQ ID NO:13), Q19D (SEQ ID NO:14), R9F (SEQ ID NO:15 ), R9V (SEQ ID NO:16), L9V (SEQ ID NO:17), G10C (SEQ ID NO:18), or D20C (SEQ ID NO:19).

7. The method of claim 5, wherein the patient is administered a combination of E7 HPV peptides selected from the group consisting of T10Q (SEQ ID NO:11), M9T (SEQ ID NO:12), D9L (SEQ ID NO:13), Q19D (SEQ ID NO:14), R9F (SEQ ID NO:15), R9V (SEQ ID NO:16), L9V (SEQ ID NO:17), G10C (SEQ ID NO:18), and D20C (SEQ ID NO:19).

8. The method of claim 1, wherein the patient is administered at least one E6 HPV peptide and at least one E7 HPV peptide.

9. The method of claim 1, wherein the patient has a history of a pre-cancerous growth.

10. The method of claim 9, wherein the pre-cancerous growth is cervical intraepithelial neoplasia (CIN).

11. The method of claim 1, wherein the patient has a history of a cancerous growth.

12. The method of claim 11, wherein the patient has a history of cervical cancer.

13. The method of claim 1, wherein the patient has undergone ablative treatment of a pre-cancerous or cancerous growth in the genitourinary tract.

14. The method of claim 13, wherein the ablative treatment is selected from the group consisting of chemotherapy, radiotherapy, hormonal therapy, gene therapy, surgery, gene therapy, and immunotherapy.

15. The method of claim 1, wherein the at least one E6 or E7 HPV peptides are comprised in a pharmaceutical composition.

16. The method of claim 15, wherein the pharmaceutical composition further comprises an adjuvant.

17. The method of claim 15, wherein the pharmaceutical composition further comprises a lipid.

18. The method of claim 17, wherein the lipid is a phosphatidylglycerol, a phosphatidylcholine, a phosphatidylserine, a phosphatidylethanolamine, a sphingolipid, a cerebroside, or a ganglioside.

19. The method of claim 18, wherein the lipid is a phosphatidylglycerol.

20. The method of claim 19, wherein the phosphatidylglycerol is diacylphosphatidyglycerol.

21. The method of claim 1, wherein identifying a patient at risk for recurrence of HPV-associated pre-cancerous or cancerous growth comprises performing a Pap Smear test.

22. The method of claim 1, wherein identifying a patient at risk for recurrence of HPV-associated pre-cancerous or cancerous growth comprises performing colposcopy on the subject.

23. The method of claim 1, wherein administering to the patient an effective amount of at least one E6 or E7 HPV peptide comprises administering to the patient an expression construct comprising a nucleic acid sequence coding for at least one E6 or E7 HPV peptide wherein the nucleic acid sequence is under the transcriptional control of a promoter.

24. The method of claim 23, wherein the expression construct is comprised in a viral vector.

25. The method of claim 24, wherein the viral vector is a retroviral vector, an adenoviral vector, an adeno-associated viral vector, a vaccinia virus vector, or a herpes virus vector.

26. The method of claim 23, wherein the expression construct is comprised in a liposome.

27. The method of claim 1, wherein the at least one E6 or E7 HPV peptide is administered intravenously, intradermally, intraarterially, intraperitoneally, intralesionally, intravaginally, rectally, topically, intratumorally, intramuscularly, subcutaneously, mucosally, orally, or topically.

* * * * *

UNITED STATES PATENT AND TRADEMARK OFFICE
CERTIFICATE OF CORRECTION

PATENT NO. : 7,659,071 B2
APPLICATION NO. : 12/172002
DATED : February 9, 2010
INVENTOR(S) : Jagannadha K. Sastry et al.

It is certified that error appears in the above-identified patent and that said Letters Patent is hereby corrected as shown below:

In column 1, lines 13-15, delete
"The U.S. government has certain rights in the present invention pursuant to grant numbers CA016672, CA065571, and CA077378 from the National Institutes of Health." and insert
--This invention was made with government support under grant numbers CA016672, CA065571, and CA077378 from the National Institutes of Health. The government has certain rights in the invention.--.

Signed and Sealed this

Twenty-seventh Day of April, 2010

David J. Kappos
*Director of the United States Patent and Trademark Office*

SEQUENCE LISTING

<160> NUMBER OF SEQ ID NOS: 27

<210> SEQ ID NO 1
<211> LENGTH: 9
<212> TYPE: PRT
<213> ORGANISM: Human papillomavirus

<400> SEQUENCE: 1

Lys Leu Pro Gln Leu Cys Thr Glu Leu
 1               5

<210> SEQ ID NO 2
<211> LENGTH: 10
<212> TYPE: PRT
<213> ORGANISM: Human papillomavirus

<400> SEQUENCE: 2

Glu Leu Gln Thr Thr Ile His Asp Ile Ile
 1               5                  10

<210> SEQ ID NO 3
<211> LENGTH: 10
<212> TYPE: PRT
<213> ORGANISM: Human papillomavirus

<400> SEQUENCE: 3

Cys Val Tyr Cys Lys Gln Gln Leu Leu Arg
 1               5                  10

<210> SEQ ID NO 4
<211> LENGTH: 15
<212> TYPE: PRT
<213> ORGANISM: Human papillomavirus

<400> SEQUENCE: 4

Gln Leu Leu Arg Arg Glu Val Tyr Asp Phe Ala Phe Arg Asp Leu
 1               5                  10                  15

<210> SEQ ID NO 5
<211> LENGTH: 10
<212> TYPE: PRT
<213> ORGANISM: Human papillomavirus

<400> SEQUENCE: 5

Val Tyr Asp Phe Ala Phe Arg Asp Leu Cys
 1               5                  10

<210> SEQ ID NO 6
<211> LENGTH: 9
<212> TYPE: PRT
<213> ORGANISM: Human papillomavirus

<400> SEQUENCE: 6

Pro Tyr Ala Val Cys Asp Lys Cys Leu
 1               5

<210> SEQ ID NO 7
<211> LENGTH: 10
<212> TYPE: PRT
<213> ORGANISM: Human papillomavirus

<400> SEQUENCE: 7

Pro Leu Cys Asp Leu Leu Ile Arg Cys Ile

```
                1               5                   10
```

<210> SEQ ID NO 8
<211> LENGTH: 20
<212> TYPE: PRT
<213> ORGANISM: Human papillomavirus

<400> SEQUENCE: 8

```
Gln Gln Tyr Asn Lys Pro Leu Cys Asp Leu Leu Ile Arg Cys Ile Asn
 1               5                   10                  15

Cys Gln Lys Pro
            20
```

<210> SEQ ID NO 9
<211> LENGTH: 16
<212> TYPE: PRT
<213> ORGANISM: Human papillomavirus

<400> SEQUENCE: 9

```
Arg Trp Thr Gly Arg Cys Met Ser Cys Cys Arg Ser Ser Arg Thr Arg
 1               5                   10                  15
```

<210> SEQ ID NO 10
<211> LENGTH: 10
<212> TYPE: PRT
<213> ORGANISM: Human papillomavirus

<400> SEQUENCE: 10

```
Gly Arg Cys Met Ser Cys Cys Arg Ser Ser
 1               5                   10
```

<210> SEQ ID NO 11
<211> LENGTH: 10
<212> TYPE: PRT
<213> ORGANISM: Human papillomavirus

<400> SEQUENCE: 11

```
Thr Leu His Glu Tyr Met Leu Glu Leu Gln
 1               5                   10
```

<210> SEQ ID NO 12
<211> LENGTH: 9
<212> TYPE: PRT
<213> ORGANISM: Human papillomavirus

<400> SEQUENCE: 12

```
Met Leu Asp Leu Gln Pro Glu Thr Thr
 1               5
```

<210> SEQ ID NO 13
<211> LENGTH: 9
<212> TYPE: PRT
<213> ORGANISM: Human papillomavirus

<400> SEQUENCE: 13

```
Asp Leu Gln Pro Glu Thr Thr Asp Leu
 1               5
```

<210> SEQ ID NO 14
<211> LENGTH: 19
<212> TYPE: PRT
<213> ORGANISM: Human papillomavirus

<400> SEQUENCE: 14

```
Gln Ala Glu Pro Asp Arg Ala His Tyr Asn Ile Val Thr Phe Cys Cys
 1               5                  10                  15

Lys Cys Asp

<210> SEQ ID NO 15
<211> LENGTH: 9
<212> TYPE: PRT
<213> ORGANISM: Human papillomavirus

<400> SEQUENCE: 15

Arg Ala His Tyr Asn Ile Val Thr Phe
 1               5

<210> SEQ ID NO 16
<211> LENGTH: 9
<212> TYPE: PRT
<213> ORGANISM: Human papillomavirus

<400> SEQUENCE: 16

Arg Leu Cys Val Gln Ser Thr His Val
 1               5

<210> SEQ ID NO 17
<211> LENGTH: 9
<212> TYPE: PRT
<213> ORGANISM: Human papillomavirus

<400> SEQUENCE: 17

Leu Leu Met Gly Thr Leu Gly Ile Val
 1               5

<210> SEQ ID NO 18
<211> LENGTH: 10
<212> TYPE: PRT
<213> ORGANISM: Human papillomavirus

<400> SEQUENCE: 18

Gly Thr Leu Gly Ile Val Cys Pro Ile Cys
 1               5                  10

<210> SEQ ID NO 19
<211> LENGTH: 20
<212> TYPE: PRT
<213> ORGANISM: Human papillomavirus

<400> SEQUENCE: 19

Asp Ile Arg Thr Leu Glu Asp Leu Leu Met Gly Thr Leu Gly Ile Val
 1               5                  10                  15

Cys Pro Ile Cys
                20

<210> SEQ ID NO 20
<211> LENGTH: 151
<212> TYPE: PRT
<213> ORGANISM: Human papillomavirus

<400> SEQUENCE: 20

Met Phe Gln Asp Pro Gln Glu Arg Pro Arg Lys Leu Pro Gln Leu Cys
 1               5                  10                  15

Thr Glu Leu Gln Thr Thr Ile His Asp Ile Ile Leu Glu Cys Val Tyr
                20                  25                  30

Cys Lys Gln Gln Leu Leu Arg Arg Glu Val Tyr Asp Phe Ala Phe Arg
                35                  40                  45
```

```
Asp Leu Cys Ile Val Tyr Arg Asp Gly Asn Pro Tyr Ala Val Cys Asp
     50                  55                  60

Lys Cys Leu Lys Phe Tyr Ser Lys Ile Ser Glu Tyr Arg His Tyr Cys
 65                  70                  75                  80

Tyr Ser Val Tyr Gly Thr Thr Leu Glu Gln Gln Tyr Asn Lys Pro Leu
                 85                  90                  95

Cys Asp Leu Leu Ile Arg Cys Ile Asn Cys Gln Lys Pro Leu Cys Pro
                100                 105                 110

Glu Glu Lys Gln Arg His Leu Asp Lys Lys Gln Arg Phe His Asn Ile
            115                 120                 125

Arg Gly Arg Trp Thr Gly Arg Cys Met Ser Cys Cys Arg Ser Ser Arg
130                 135                 140

Thr Arg Arg Glu Thr Gln Leu
145                 150

<210> SEQ ID NO 21
<211> LENGTH: 590
<212> TYPE: PRT
<213> ORGANISM: Human papillomavirus

<400> SEQUENCE: 21

Met Ser Leu Pro Gly Gly Arg Gly Thr Val Lys Ile Glu Thr Arg Glu
  1               5                  10                  15

Arg Ile Trp Val Arg Arg Val Asn Gly Glu Thr Gly Val Tyr Asp Thr
                 20                  25                  30

Arg Ala Gly Ser Phe Glu Thr Val Ser Cys Gln Glu Phe Glu Ala Ala
             35                  40                  45

Ala Asp Thr Val Pro Ser Val Pro Val Phe Cys Asp Arg Cys Phe Gly
     50                  55                  60

Thr Ser Leu Tyr Glu Val Pro Leu Thr Gly Phe Gly Thr Phe Val Val
 65                  70                  75                  80

Gly Thr Cys Cys Ile Phe Ser Pro Gly Asp Pro Val Asp Asp Pro Ser
                 85                  90                  95

Ile Pro Ala His Met Arg Lys Tyr Gln Gln Pro Ile Glu Ala His Gln
                100                 105                 110

Thr Met Val Gln Val Ala Pro Gly Thr Leu Lys Tyr Ser His Gln Ile
            115                 120                 125

Pro Met Gly Lys Val Leu Gly Tyr Trp His Val His Met Glu Asp Arg
130                 135                 140

Val Tyr Leu Asn Met Ile Gly Gly Ile Asp Glu Ser Glu Asp Thr Gly
145                 150                 155                 160

Lys Arg Cys Val Glu Thr Phe Thr Glu Ala Asp Ile Pro Cys Ala Leu
                165                 170                 175

Ser Leu Gly Thr Leu Asp Val Gly Leu Asn Glu Val Ile Leu Glu Cys
                180                 185                 190

Ser Val Val Ile Pro Ala Arg Arg Gly Cys His Ala Lys Leu Phe
            195                 200                 205

Thr Arg Asp Thr Val Ser Asp Gly Leu Glu Lys Phe Cys Phe Gln Ser
210                 215                 220

His Ala Thr Leu Pro Pro Thr Leu Leu Ala Ser Phe Gly Ser Thr Ser
225                 230                 235                 240

Glu Ser Pro Glu Arg Lys Thr Phe Tyr Glu Ala His Val Asp Ala Leu
                245                 250                 255

Asn Asn Tyr Ile Lys Leu Leu Arg Thr Ile Tyr Ser His Lys Gly Glu
```

-continued

```
                260                 265                 270
Thr Glu Ile Glu Gln Tyr Leu Ile Glu Gly Ser Lys Leu Tyr Ser Glu
            275                 280                 285
Leu Ile Gly Glu Pro Ser Arg Val Leu Asp Ala Thr Met Lys Ala Ala
        290                 295                 300
Gln Ile Ala Glu Pro Gln Thr His Thr Gly Gly Ala Asp Arg Gln Arg
305                 310                 315                 320
Pro Gln Arg Pro Asp Gly Ile Pro Tyr Ser Val Pro Arg Asp Phe Pro
                325                 330                 335
Met Thr Gly Tyr Pro Phe Ala Pro Gln Phe Cys Gly Asp Pro Gly Leu
            340                 345                 350
Val Ser His Tyr Asn Pro Phe Val Pro Pro Gln Ser Phe Gly Gln Gly
        355                 360                 365
Tyr Gly Pro Glu Arg Val Gly Gly Tyr Pro Gln Pro Pro Asn Pro
    370                 375                 380
Tyr Val Leu Pro Ile Ser Tyr Gly Gln Gln Pro Tyr Pro Gly His Pro
385                 390                 395                 400
Gln Pro His Gly His His Gln Gln Arg Ser Gly Gly Asp Leu Lys
                405                 410                 415
Ala Glu Leu Ile Glu Thr Leu Gly Leu Ala Pro Lys Thr Asn Ala Val
            420                 425                 430
Gln Glu Ser Leu Lys Ser Phe Ile Ser Glu Ile Leu Glu Ser Glu Leu
        435                 440                 445
Lys Asn Cys Gly Ile Lys Arg Ala Ala Gly Asn Ile Glu Arg Asn Cys
    450                 455                 460
Asp Val Asp Glu Glu Pro Pro Arg Thr Lys Arg Ala Arg Pro Glu Pro
465                 470                 475                 480
Lys Thr Ala Val Glu Ala Ile Val Arg Ala Pro Tyr Gly Asp Phe Asp
                485                 490                 495
Ser Thr Ala Leu Thr Thr Lys Ile Gly Gln Val Ser Asp Thr Val Glu
            500                 505                 510
Lys Leu Asn Lys Val Ile Glu Thr Leu Leu Thr Gln Ser Ser Ala Gln
        515                 520                 525
Pro Ala Pro Leu Ser Thr Pro Ala Gln Ala Pro Val Gln Pro Ser
    530                 535                 540
Leu Pro Gln Pro Val Pro Glu Pro Leu Ala Pro Gln Glu Pro Pro Pro
545                 550                 555                 560
Pro Gly Thr Ser Ala Pro Thr Leu Glu Ala Ser Leu Pro Gln Gln Lys
                565                 570                 575
Pro Val Val Ser Lys Gly Ala Phe Glu Thr Leu Met Asn Leu
            580                 585                 590
```

<210> SEQ ID NO 22
<211> LENGTH: 13
<212> TYPE: PRT
<213> ORGANISM: Murine

<400> SEQUENCE: 22

Ser Thr Arg Thr Pro Glu Asp Ser Asn Ser Leu Gly Thr
 1               5                  10

<210> SEQ ID NO 23
<211> LENGTH: 20
<212> TYPE: DNA
<213> ORGANISM: Human papillomavirus
<220> FEATURE:

```
<221> NAME/KEY: modified_base
<222> LOCATION: (3)
<223> OTHER INFORMATION: M = A, C, or R
<220> FEATURE:
<221> NAME/KEY: modified_base
<222> LOCATION: (9)
<223> OTHER INFORMATION: W = A and T
<220> FEATURE:
<221> NAME/KEY: modified_base
<222> LOCATION: (15)
<223> OTHER INFORMATION: Y = C and T

<400> SEQUENCE: 23
gcmcagggwc ataayaatgg                                                 20

<210> SEQ ID NO 24
<211> LENGTH: 20
<212> TYPE: DNA
<213> ORGANISM: Human papillomavirus
<220> FEATURE:
<221> NAME/KEY: modified_base
<222> LOCATION: (6)
<223> OTHER INFORMATION: M = A, C, or R
<220> FEATURE:
<221> NAME/KEY: modified_base
<222> LOCATION: (8)..(9)
<223> OTHER INFORMATION: R = A and G
<220> FEATURE:
<221> NAME/KEY: modified_base
<222> LOCATION: (13)
<223> OTHER INFORMATION: W = A and T

<400> SEQUENCE: 24
cgtccmarrg gawactgatc                                                 20

<210> SEQ ID NO 25
<211> LENGTH: 20
<212> TYPE: DNA
<213> ORGANISM: Human papillomavirus

<400> SEQUENCE: 25
catacacctc cagcacctaa                                                 20

<210> SEQ ID NO 26
<211> LENGTH: 98
<212> TYPE: PRT
<213> ORGANISM: Human papillomavirus type 16

<400> SEQUENCE: 26

Met His Gly Asp Thr Pro Thr Leu His Glu Tyr Met Leu Asp Leu Gln
 1               5                  10                  15

Pro Glu Thr Thr Asp Leu Tyr Cys Tyr Glu Gln Leu Ser Asp Ser Ser
                20                  25                  30

Glu Glu Glu Asp Glu Ile Asp Gly Pro Ala Gly Gln Ala Glu Pro Asp
            35                  40                  45

Arg Ala His Tyr Asn Ile Val Thr Phe Cys Cys Lys Cys Asp Ser Thr
        50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro

<210> SEQ ID NO 27
<211> LENGTH: 151
```

-continued

```
<212> TYPE: PRT
<213> ORGANISM: Human papillomavirus type 16

<400> SEQUENCE: 27

Met Phe Gln Asp Pro Gln Glu Arg Pro Arg Lys Leu Pro Gln Leu Cys
  1               5                  10                  15

Thr Glu Leu Gln Thr Thr Ile His Asp Ile Ile Leu Glu Cys Val Tyr
             20                  25                  30

Cys Lys Gln Gln Leu Leu Arg Arg Glu Val Tyr Asp Phe Ala Phe Arg
         35                  40                  45

Asp Leu Cys Ile Val Tyr Arg Asp Gly Asn Pro Tyr Ala Val Cys Asp
     50                  55                  60

Lys Cys Leu Lys Phe Tyr Ser Lys Ile Ser Glu Tyr Arg His Tyr Cys
 65                  70                  75                  80

Tyr Ser Val Tyr Gly Thr Thr Leu Glu Gln Gln Tyr Asn Lys Pro Leu
                 85                  90                  95

Cys Asp Leu Leu Ile Arg Cys Ile Asn Cys Gln Lys Pro Leu Cys Pro
             100                 105                 110

Glu Glu Lys Gln Arg His Leu Asp Lys Lys Gln Arg Phe His Asn Ile
         115                 120                 125

Arg Gly Arg Trp Thr Gly Arg Cys Met Ser Cys Cys Arg Ser Ser Arg
     130                 135                 140

Thr Arg Arg Glu Thr Gln Leu
145                 150
```